US011950872B2

(12) United States Patent
Castillo et al.

(10) Patent No.: US 11,950,872 B2
(45) Date of Patent: Apr. 9, 2024

(54) DYNAMIC PULLEY SYSTEM

(71) Applicant: Auris Health, Inc., Redwood City, CA (US)

(72) Inventors: Andre J. Castillo, Redwood City, CA (US); Akira Bryan Ueda, San Fransisco, CA (US)

(73) Assignee: Auris Health, Inc., Redwood City, CA (US)

( * ) Notice: Subject to any disclaimer, the term of this patent is extended or adjusted under 35 U.S.C. 154(b) by 386 days.

(21) Appl. No.: 17/130,496

(22) Filed: Dec. 22, 2020

(65) Prior Publication Data

US 2021/0196415 A1  Jul. 1, 2021

Related U.S. Application Data

(60) Provisional application No. 62/956,001, filed on Dec. 31, 2019.

(51) Int. Cl.
*A61B 34/00* (2016.01)
*A61B 34/20* (2016.01)
*A61B 34/30* (2016.01)
*B25J 18/04* (2006.01)

(52) U.S. Cl.
CPC ...... *A61B 34/71* (2016.02); *A61B 2034/2051* (2016.02); *A61B 2034/301* (2016.02); *B25J 18/04* (2013.01); *Y10T 74/19819* (2015.01)

(58) Field of Classification Search
CPC ... F16H 55/46; F16H 9/10; F16H 9/00; F16H 55/36; F16H 2007/0863; F16H 2007/0868; F16H 2007/0865; F16H 7/08; B25J 9/0078; A61B 2034/715; A61B 34/71

See application file for complete search history.

(56) References Cited

U.S. PATENT DOCUMENTS

| 2,556,601 A | 6/1951 | Schofield |
| 2,566,183 A | 8/1951 | Forss |
| 2,623,175 A | 12/1952 | Finke |
| 2,730,699 A | 1/1956 | Gratian |

(Continued)

FOREIGN PATENT DOCUMENTS

| CN | 1846181 | 10/2006 |
| CN | 1857877 | 11/2006 |

(Continued)

OTHER PUBLICATIONS

International Preliminary Report on Patentability and Written Opinion for Appl. No. PCT/IB2020/062353, dated Jul. 5, 2022, 7 pages.

(Continued)

*Primary Examiner* — Gregory Robert Weber
(74) *Attorney, Agent, or Firm* — Chang & Hale LLP

(57) ABSTRACT

Certain aspects relate to systems and techniques for robotic medical instrument system. The medical system can include an elongated shaft configured for insertion into a patient. The system can also include a pull wire extending along the elongated shaft. The pull wire can be actuatable to articulate the elongated shaft. The medical system can include a dynamic pulley coupled to the pull wire, the dynamic pulley configured to collapse during rotation in a first direction and to expand during rotation in a second direction opposite the first direction.

21 Claims, 29 Drawing Sheets

(56) References Cited

U.S. PATENT DOCUMENTS

| | | |
|---|---|---|
| 2,884,808 A | 5/1959 | Mueller |
| 3,294,183 A | 12/1966 | Riley et al. |
| 3,472,083 A | 10/1969 | Schnepel |
| 3,513,724 A | 5/1970 | Box |
| 3,572,325 A | 3/1971 | Bazell et al. |
| 3,595,074 A | 7/1971 | Johnson |
| 3,734,207 A | 5/1973 | Fishbein |
| 3,739,923 A | 6/1973 | Totsuka |
| 3,763,860 A | 10/1973 | Clarke |
| 3,784,031 A | 1/1974 | Nitu |
| 3,790,002 A | 2/1974 | Guilbaud et al. |
| 3,913,565 A | 10/1975 | Kawahara |
| 3,921,536 A | 11/1975 | Savage |
| 3,926,386 A | 12/1975 | Stahmann |
| 4,040,413 A | 8/1977 | Ohshiro |
| 4,141,245 A | 2/1979 | Brandstetter |
| 4,198,960 A | 4/1980 | Utsugi |
| 4,241,884 A | 12/1980 | Lynch |
| 4,243,034 A | 1/1981 | Brandt |
| 4,294,234 A | 10/1981 | Matsuo |
| 4,351,493 A | 9/1982 | Sonnek |
| 4,357,843 A | 11/1982 | Peck et al. |
| 4,384,493 A | 5/1983 | Grunbaum |
| 4,392,485 A | 7/1983 | Hiltebrandt |
| 4,470,407 A | 9/1984 | Hussein |
| 4,483,326 A | 11/1984 | Yamaka et al. |
| 4,507,026 A | 3/1985 | Lund |
| 4,530,471 A | 7/1985 | Inoue |
| 4,532,935 A | 8/1985 | Wang et al. |
| 4,555,960 A | 12/1985 | King |
| 4,607,619 A | 8/1986 | Seike et al. |
| 4,608,034 A * | 8/1986 | Reswick .................. F16H 9/10 474/49 |
| 4,685,458 A | 8/1987 | Leckrone |
| 4,688,555 A | 8/1987 | Wardle |
| 4,690,175 A | 9/1987 | Ouchi et al. |
| 4,706,656 A | 11/1987 | Kubota |
| 4,741,326 A | 5/1988 | Sidall et al. |
| 4,745,908 A | 5/1988 | Wardle |
| 4,747,405 A | 5/1988 | Leckrone |
| 4,748,969 A | 6/1988 | Wardle |
| 4,750,475 A | 6/1988 | Yoshihashi |
| 4,771,766 A | 9/1988 | Aoshiro |
| 4,784,150 A | 11/1988 | Voorhies et al. |
| 4,846,791 A | 7/1989 | Hattler et al. |
| 4,854,301 A | 8/1989 | Nakajima |
| 4,857,058 A | 8/1989 | Payton |
| 4,869,238 A | 9/1989 | Opie et al. |
| 4,898,574 A | 2/1990 | Uchiyama et al. |
| 4,906,496 A | 3/1990 | Hosono et al. |
| 4,907,168 A | 3/1990 | Boggs |
| 4,945,790 A | 8/1990 | Golden |
| 4,967,732 A | 11/1990 | Inoue |
| 4,983,165 A | 1/1991 | Loiterman |
| 5,029,574 A | 7/1991 | Shimamura et al. |
| 5,050,585 A | 9/1991 | Takahashi |
| 5,083,549 A | 1/1992 | Cho et al. |
| 5,085,659 A | 2/1992 | Rydell |
| 5,106,387 A | 4/1992 | Kittrell et al. |
| 5,108,800 A | 4/1992 | Koo |
| 5,125,909 A | 6/1992 | Heimberger |
| 5,150,452 A | 9/1992 | Pollack et al. |
| 5,168,864 A | 12/1992 | Shockey |
| 5,196,023 A | 3/1993 | Martin |
| 5,207,128 A | 5/1993 | Albright |
| 5,217,002 A | 6/1993 | Katsurada |
| 5,217,465 A | 6/1993 | Steppe |
| 5,234,428 A | 8/1993 | Kaufman |
| 5,251,611 A | 10/1993 | Zehel et al. |
| 5,256,150 A | 10/1993 | Quiachon et al. |
| 5,257,617 A | 11/1993 | Takahashi |
| 5,261,391 A | 11/1993 | Inoue |
| 5,277,085 A | 1/1994 | Tanimura et al. |
| 5,287,861 A | 2/1994 | Wilk |
| 5,308,323 A | 5/1994 | Sogawa et al. |
| 5,313,934 A | 5/1994 | Wiita et al. |
| 5,318,589 A | 6/1994 | Lichtman |
| 5,325,848 A | 7/1994 | Adams et al. |
| 5,342,381 A | 8/1994 | Tidemand |
| 5,344,395 A | 9/1994 | Whalen et al. |
| 5,350,101 A | 9/1994 | Godlewski |
| 5,353,783 A | 10/1994 | Nakao et al. |
| 5,370,609 A | 12/1994 | Drasler et al. |
| 5,372,124 A | 12/1994 | Takayama et al. |
| 5,386,818 A | 2/1995 | Schneebaum |
| 5,411,016 A | 5/1995 | Kume |
| 5,426,687 A | 6/1995 | Goodall et al. |
| 5,431,649 A | 7/1995 | Mulier et al. |
| 5,441,485 A | 8/1995 | Peters |
| 5,448,988 A | 9/1995 | Watanabe |
| 5,449,356 A | 9/1995 | Walbrink |
| 5,450,843 A | 9/1995 | Moll et al. |
| 5,472,426 A | 12/1995 | Bonati et al. |
| 5,478,330 A | 12/1995 | Imran et al. |
| 5,482,029 A | 1/1996 | Sekiguchi |
| 5,489,270 A | 2/1996 | van Erp |
| 5,496,267 A | 3/1996 | Drasler |
| 5,501,667 A | 3/1996 | Verduin, Jr. |
| 5,507,725 A | 4/1996 | Savage et al. |
| 5,520,684 A | 5/1996 | Imran |
| 5,524,180 A | 6/1996 | Wang et al. |
| 5,533,985 A | 7/1996 | Wang |
| 5,545,170 A | 8/1996 | Hart |
| 5,559,294 A | 9/1996 | Holum et al. |
| 5,562,239 A | 10/1996 | Boiarski et al. |
| 5,562,648 A | 10/1996 | Peterson |
| 5,562,678 A | 10/1996 | Booker |
| 5,572,999 A | 11/1996 | Funda et al. |
| 5,573,535 A | 11/1996 | Viklund |
| 5,580,200 A | 12/1996 | Fullerton |
| 5,613,973 A | 3/1997 | Jackson et al. |
| 5,645,083 A | 7/1997 | Essig et al. |
| 5,658,311 A | 8/1997 | Baden |
| 5,681,296 A | 10/1997 | Ishida |
| 5,695,500 A | 12/1997 | Taylor et al. |
| 5,697,949 A | 12/1997 | Giurtino et al. |
| 5,704,534 A | 1/1998 | Huitema et al. |
| 5,709,661 A | 1/1998 | Van Egmond |
| 5,710,870 A | 1/1998 | Ohm |
| 5,716,325 A | 2/1998 | Bonutti |
| 5,720,775 A | 2/1998 | Lamard |
| 5,737,500 A | 4/1998 | Seraji et al. |
| 5,741,429 A | 4/1998 | Donadio, III |
| 5,749,889 A | 5/1998 | Bacich et al. |
| 5,767,840 A | 6/1998 | Selker |
| 5,779,623 A | 7/1998 | Bonnell |
| 5,788,667 A | 8/1998 | Stoller |
| 5,792,135 A | 8/1998 | Madhani et al. |
| 5,792,165 A | 8/1998 | Klieman |
| 5,797,900 A | 8/1998 | Madhani |
| 5,798,627 A | 8/1998 | Gilliland |
| 5,810,770 A | 9/1998 | Chin et al. |
| 5,842,390 A | 12/1998 | Bouligny |
| 5,855,583 A | 1/1999 | Wang et al. |
| 5,873,817 A | 2/1999 | Kokish et al. |
| 5,876,325 A | 3/1999 | Mizuno et al. |
| 5,882,347 A | 3/1999 | Mouris-Laan |
| 5,888,191 A | 3/1999 | Akiba |
| 5,893,869 A | 4/1999 | Barnhart |
| 5,897,491 A | 4/1999 | Kastenbauer et al. |
| 5,910,129 A | 6/1999 | Koblish et al. |
| 5,921,968 A | 7/1999 | Lampropoulos et al. |
| 5,924,175 A | 7/1999 | Lippitt |
| 5,938,586 A | 8/1999 | Wilk |
| 5,938,587 A | 8/1999 | Taylor et al. |
| 5,943,056 A | 8/1999 | Sato |
| 5,967,934 A | 10/1999 | Ishida et al. |
| 5,989,230 A | 11/1999 | Frassica |
| 6,012,494 A | 1/2000 | Balazs |
| 6,071,281 A | 6/2000 | Burnside et al. |
| 6,077,219 A | 6/2000 | Viebach |
| 6,084,371 A | 7/2000 | Kress et al. |
| 6,093,157 A | 7/2000 | Chandrasekaran |
| 6,110,171 A | 8/2000 | Rydell |

(56) References Cited

U.S. PATENT DOCUMENTS

| | | | |
|---|---|---|---|
| 6,120,476 A | 9/2000 | Fung et al. | |
| 6,120,498 A | 9/2000 | Jani et al. | |
| 6,143,013 A | 11/2000 | Samson et al. | |
| 6,154,000 A | 11/2000 | Rastegar et al. | |
| 6,156,030 A | 12/2000 | Neev | |
| 6,157,853 A | 12/2000 | Blume et al. | |
| 6,171,234 B1 | 1/2001 | White et al. | |
| 6,174,280 B1 | 1/2001 | Oneda | |
| 6,174,318 B1 | 1/2001 | Bates et al. | |
| 6,185,478 B1 | 2/2001 | Koakutsu et al. | |
| 6,197,015 B1 | 3/2001 | Wilson | |
| 6,198,974 B1 | 3/2001 | Webster, Jr. | |
| 6,206,903 B1 | 3/2001 | Ramans | |
| 6,234,958 B1 | 5/2001 | Snoke et al. | |
| 6,236,906 B1 | 5/2001 | Muller | |
| 6,183,435 B1 | 6/2001 | Bumbalough et al. | |
| 6,272,371 B1 | 8/2001 | Shlomo | |
| 6,289,579 B1 | 9/2001 | Viza et al. | |
| 6,315,715 B1 | 11/2001 | Taylor et al. | |
| 6,322,557 B1 | 11/2001 | Nikolaevich | |
| 6,375,635 B1 | 4/2002 | Moutafis | |
| 6,394,998 B1 | 5/2002 | Wallace et al. | |
| 6,401,572 B1 | 6/2002 | Provost | |
| 6,404,497 B1 | 6/2002 | Backman | |
| 6,405,078 B1 | 6/2002 | Moaddeb et al. | |
| 6,436,107 B1 | 8/2002 | Wang et al. | |
| 6,440,061 B1 | 8/2002 | Wenner et al. | |
| 6,464,632 B1 | 10/2002 | Taylor | |
| 6,485,411 B1 | 11/2002 | Konstorum | |
| 6,487,940 B2 | 12/2002 | Hart et al. | |
| 6,491,626 B1 | 12/2002 | Stone et al. | |
| 6,491,701 B2 | 12/2002 | Tierney et al. | |
| 6,508,823 B1 | 1/2003 | Gonon | |
| 6,522,906 B1 | 2/2003 | Salisbury et al. | |
| 6,537,205 B1 | 3/2003 | Smith | |
| 6,554,793 B1 | 4/2003 | Pauker et al. | |
| 6,577,891 B1 | 6/2003 | Jaross et al. | |
| 6,653,374 B1 | 11/2003 | Jang et al. | |
| 6,676,668 B2 | 1/2004 | Mercereau et al. | |
| 6,685,698 B2 | 2/2004 | Morley et al. | |
| 6,695,818 B2 | 2/2004 | Wollschlager | |
| 6,706,050 B1 | 3/2004 | Giannadakis | |
| 6,716,178 B1 | 4/2004 | Kilpatrick et al. | |
| 6,726,675 B1 | 4/2004 | Beyar | |
| 6,746,422 B1 | 6/2004 | Noriega | |
| 6,749,560 B1 | 6/2004 | Konstorum | |
| 6,786,896 B1 | 9/2004 | Madhani et al. | |
| 6,790,173 B2 | 9/2004 | Saadat | |
| 6,827,710 B1 | 12/2004 | Mooney et al. | |
| 6,827,712 B2 | 12/2004 | Tovey et al. | |
| 6,837,846 B2 | 1/2005 | Jaffe | |
| 6,879,287 B2 | 4/2005 | Popov | |
| 6,908,428 B2 | 6/2005 | Aizenfeld | |
| 6,921,362 B2 | 7/2005 | Ouchi | |
| 6,958,035 B2 | 10/2005 | Friedman et al. | |
| 7,008,401 B2 | 3/2006 | Thompson et al. | |
| 7,044,936 B2 | 5/2006 | Harding | |
| 7,130,700 B2 | 10/2006 | Gardeski et al. | |
| 7,172,580 B2 | 2/2007 | Hruska et al. | |
| 7,248,944 B2 | 7/2007 | Green | |
| 7,276,044 B2 | 10/2007 | Ferry et al. | |
| 7,282,055 B2 | 10/2007 | Tsuruta | |
| 7,559,934 B2 | 7/2009 | Teague et al. | |
| 7,594,903 B2 | 9/2009 | Webler et al. | |
| 7,615,042 B2 | 11/2009 | Beyar et al. | |
| 7,635,342 B2 | 12/2009 | Ferry et al. | |
| 7,645,230 B2 | 1/2010 | Mikkaichi | |
| 7,645,231 B2 | 1/2010 | Akiba | |
| 7,736,356 B2 | 6/2010 | Cooper et al. | |
| 7,766,856 B2 | 8/2010 | Ferry et al. | |
| 7,781,724 B2 | 8/2010 | Childers et al. | |
| 7,789,827 B2 | 9/2010 | Landry | |
| 7,882,841 B2 | 2/2011 | Aljuri | |
| 7,930,065 B2 | 4/2011 | Larkin et al. | |
| 7,938,809 B2 | 5/2011 | Lampropoulos et al. | |
| 7,963,911 B2 | 6/2011 | Turliuc | |
| 7,972,298 B2 | 7/2011 | Wallace et al. | |
| 7,974,674 B2 | 7/2011 | Hauck et al. | |
| 7,987,046 B1 | 7/2011 | Peterman | |
| 7,998,020 B2 | 8/2011 | Kidd et al. | |
| 8,002,713 B2 | 8/2011 | Heske | |
| 8,004,229 B2 | 8/2011 | Nowlin et al. | |
| 8,038,598 B2 | 10/2011 | Khachi | |
| 8,046,049 B2 | 10/2011 | Govari et al. | |
| 8,052,636 B2 | 11/2011 | Moll et al. | |
| 8,092,397 B2 | 1/2012 | Wallace et al. | |
| 8,157,308 B2 | 4/2012 | Pedersen | |
| 8,182,415 B2 | 5/2012 | Larkin et al. | |
| 8,187,173 B2 | 5/2012 | Miyoshi | |
| 8,246,536 B2 | 8/2012 | Ochi | |
| 8,257,303 B2 | 9/2012 | Moll et al. | |
| 8,277,417 B2 | 10/2012 | Fedinec et al. | |
| 8,291,791 B2 | 10/2012 | Light et al. | |
| 8,414,505 B1 | 4/2013 | Weitzner | |
| 8,425,465 B2 | 4/2013 | Nagano | |
| 8,444,637 B2 | 5/2013 | Podmore et al. | |
| 8,460,236 B2 | 6/2013 | Roelle et al. | |
| 8,480,595 B2 | 7/2013 | Speeg | |
| 8,498,691 B2 | 7/2013 | Moll et al. | |
| 8,515,215 B2 | 8/2013 | Younge et al. | |
| 8,523,762 B2 | 9/2013 | Miyamoto et al. | |
| 8,540,748 B2 | 9/2013 | Murphy et al. | |
| 8,541,970 B2 | 9/2013 | Nowlin | |
| 8,652,030 B2 | 2/2014 | Matsuura et al. | |
| 8,671,817 B1 | 3/2014 | Bogusky | |
| 8,686,747 B2 | 4/2014 | Berner | |
| 8,720,448 B2 | 5/2014 | Reis et al. | |
| 8,746,252 B2 | 6/2014 | McGrogan et al. | |
| 8,749,190 B2 | 6/2014 | Nowlin et al. | |
| 8,758,231 B2 | 6/2014 | Bunch et al. | |
| 8,786,241 B2 | 7/2014 | Nowlin et al. | |
| 8,820,603 B2 | 9/2014 | Shelton et al. | |
| 8,821,480 B2 | 9/2014 | Burbank | |
| 8,827,947 B2 | 9/2014 | Bosman et al. | |
| 8,870,815 B2 | 10/2014 | Bhat et al. | |
| 8,882,660 B2 | 11/2014 | Phee et al. | |
| 8,945,163 B2 | 2/2015 | Voegele et al. | |
| 8,956,280 B2 | 2/2015 | Eversull et al. | |
| 8,961,533 B2 | 2/2015 | Stahler et al. | |
| 8,968,333 B2 | 3/2015 | Yu et al. | |
| 8,992,542 B2 | 3/2015 | Hagag et al. | |
| 9,173,713 B2 | 11/2015 | Hart et al. | |
| 9,179,979 B2 | 11/2015 | Jinno | |
| 9,186,046 B2 | 11/2015 | Ramamurthy et al. | |
| 9,204,933 B2 | 12/2015 | Reis et al. | |
| 9,259,280 B2 | 2/2016 | Au | |
| 9,259,281 B2 | 2/2016 | Griffiths et al. | |
| 9,259,282 B2 | 2/2016 | Azizian | |
| 9,296,104 B2 | 3/2016 | Swarup et al. | |
| 9,314,953 B2 | 4/2016 | Lauer | |
| 9,326,822 B2 | 5/2016 | Lewis et al. | |
| 9,345,456 B2 | 5/2016 | Tsonton et al. | |
| 9,345,544 B2 | 5/2016 | Hourtash et al. | |
| 9,375,284 B2 | 6/2016 | Hourtash | |
| 9,408,669 B2 | 8/2016 | Kokish et al. | |
| 9,415,510 B2 | 8/2016 | Hourtash et al. | |
| 9,427,551 B2 | 8/2016 | Leeflang et al. | |
| 9,446,177 B2 | 9/2016 | Millman et al. | |
| 9,452,018 B2 | 9/2016 | Yu | |
| 9,457,168 B2 | 10/2016 | Moll et al. | |
| 9,460,536 B2 | 10/2016 | Hasegawa et al. | |
| 9,462,931 B2 * | 10/2016 | Greig | A61B 1/0057 |
| 9,480,534 B2 | 11/2016 | Bowling | |
| 9,498,601 B2 | 11/2016 | Tanner et al. | |
| 9,504,604 B2 | 11/2016 | Alvarez | |
| 9,510,911 B2 | 12/2016 | Hourtash | |
| 9,517,106 B2 | 12/2016 | Hourtash et al. | |
| 9,561,083 B2 | 2/2017 | Yu et al. | |
| 9,566,125 B2 | 2/2017 | Bowling | |
| 9,591,990 B2 | 3/2017 | Chen et al. | |
| 9,592,042 B2 | 3/2017 | Titus | |
| 9,597,152 B2 | 3/2017 | Schaeffer | |
| 9,622,827 B2 | 4/2017 | Yu et al. | |
| 9,636,184 B2 | 5/2017 | Lee et al. | |

(56) References Cited

U.S. PATENT DOCUMENTS

| | | |
|---|---|---|
| 9,636,483 B2 | 5/2017 | Hart et al. |
| 9,668,814 B2 | 6/2017 | Kokish |
| 9,675,422 B2 | 6/2017 | Hourtash et al. |
| 9,687,310 B2 | 6/2017 | Nowlin et al. |
| 9,713,509 B2 | 7/2017 | Schuh et al. |
| 9,726,476 B2 | 8/2017 | Ramamurthy et al. |
| 9,727,963 B2 | 8/2017 | Mintz et al. |
| 9,730,757 B2 | 8/2017 | Brudniok |
| 9,737,371 B2 | 8/2017 | Romo et al. |
| 9,737,373 B2 | 8/2017 | Schuh |
| 9,744,335 B2 * | 8/2017 | Jiang ............ A61M 25/0147 |
| 9,763,741 B2 | 9/2017 | Alvarez et al. |
| 9,788,910 B2 | 10/2017 | Schuh |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,659 B2 | 3/2018 | Chopra |
| 9,918,681 B2 | 3/2018 | Wallace et al. |
| 9,931,025 B1 | 4/2018 | Graetzel et al. |
| 9,943,962 B2 | 4/2018 | Sattler et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 9,993,614 B2 | 6/2018 | Pacheco |
| 10,016,900 B1 | 7/2018 | Meyer et al. |
| 10,022,192 B1 | 7/2018 | Ummalaneni |
| 10,024,401 B2 * | 7/2018 | Kurematsu ............ F16H 7/08 |
| 10,029,367 B2 | 7/2018 | Hourtash |
| 10,046,140 B2 | 8/2018 | Kokish et al. |
| 10,071,479 B2 | 9/2018 | Swarup et al. |
| 10,080,576 B2 | 9/2018 | Romo et al. |
| 10,117,713 B2 | 11/2018 | Moctezuma de la Barrera |
| 10,130,427 B2 | 11/2018 | Tanner et al. |
| 10,130,429 B1 | 11/2018 | Weir |
| 10,136,949 B2 | 11/2018 | Felder et al. |
| 10,136,959 B2 | 11/2018 | Mintz et al. |
| 10,143,360 B2 | 12/2018 | Roelle et al. |
| 10,145,747 B1 | 12/2018 | Lin et al. |
| 10,149,720 B2 | 12/2018 | Romo |
| 10,154,822 B2 | 12/2018 | Henderson |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,213,264 B2 | 2/2019 | Tanner et al. |
| 10,219,868 B2 | 3/2019 | Weir |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,258,285 B2 | 4/2019 | Hauck |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,314,661 B2 | 6/2019 | Bowling |
| 10,327,855 B2 | 6/2019 | Hourtash et al. |
| 10,350,017 B2 | 7/2019 | Bowling |
| 10,350,390 B2 | 7/2019 | Moll et al. |
| 10,363,103 B2 | 7/2019 | Alvarez et al. |
| 10,376,672 B2 | 8/2019 | Yu |
| 10,383,765 B2 | 8/2019 | Alvarez et al. |
| 10,398,518 B2 | 9/2019 | Yu et al. |
| 10,405,908 B2 | 9/2019 | Redmond et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,454,347 B2 | 10/2019 | Covington et al. |
| 10,463,439 B2 | 11/2019 | Joseph et al. |
| 10,463,440 B2 | 11/2019 | Bowling |
| 10,464,209 B2 | 11/2019 | Ho et al. |
| 10,470,830 B2 | 11/2019 | Hill |
| 10,478,595 B2 | 11/2019 | Kokish |
| 10,482,599 B2 | 11/2019 | Mintz et al. |
| 10,493,239 B2 | 12/2019 | Hart et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |
| 10,524,867 B2 | 1/2020 | Kokish et al. |
| 10,539,478 B2 | 1/2020 | Lin |
| 10,543,047 B2 | 1/2020 | Yu |
| 10,543,048 B2 | 1/2020 | Noonan et al. |
| 10,555,778 B2 | 2/2020 | Ummalaneni et al. |
| 10,555,780 B2 | 2/2020 | Tanner et al. |
| 10,556,092 B2 | 2/2020 | Yu et al. |
| 10,569,052 B2 | 2/2020 | Kokish et al. |
| 10,631,949 B2 | 4/2020 | Schuh et al. |
| 10,639,108 B2 | 5/2020 | Romo et al. |
| 10,639,109 B2 | 5/2020 | Bovay et al. |
| 10,639,114 B2 | 5/2020 | Schuh |
| 10,667,720 B2 | 6/2020 | Wong et al. |
| 10,667,871 B2 | 6/2020 | Romo et al. |
| 10,667,875 B2 | 6/2020 | DeFonzo |
| 10,682,189 B2 | 6/2020 | Schuh et al. |
| 10,687,903 B2 | 6/2020 | Lewis et al. |
| 10,695,536 B2 | 6/2020 | Weitzner et al. |
| 10,702,348 B2 | 7/2020 | Moll et al. |
| 10,716,461 B2 | 7/2020 | Jenkins |
| 10,743,751 B2 | 8/2020 | Landey et al. |
| 10,744,035 B2 | 8/2020 | Alvarez et al. |
| 10,751,140 B2 | 8/2020 | Wallace et al. |
| 10,765,303 B2 | 9/2020 | Graetzel et al. |
| 10,765,487 B2 | 9/2020 | Ho |
| 10,779,898 B2 | 9/2020 | Hill |
| 10,786,329 B2 | 9/2020 | Schuh et al. |
| 10,786,432 B2 | 10/2020 | Mintz et al. |
| 10,792,112 B2 | 10/2020 | Kokish et al. |
| 10,792,464 B2 | 10/2020 | Romo et al. |
| 10,792,466 B2 | 10/2020 | Landey et al. |
| 10,813,539 B2 | 10/2020 | Graetzel et al. |
| 10,814,101 B2 | 10/2020 | Jiang |
| 10,820,947 B2 | 11/2020 | Julian |
| 10,820,952 B2 | 11/2020 | Yu |
| 10,820,954 B2 | 11/2020 | Marsot et al. |
| 10,827,913 B2 | 11/2020 | Ummalaneni et al. |
| 10,828,118 B2 | 11/2020 | Schuh et al. |
| 10,835,153 B2 | 11/2020 | Rafii-Tari et al. |
| 10,850,013 B2 | 12/2020 | Hsu |
| 10,881,280 B2 | 1/2021 | Baez |
| 2001/0004676 A1 | 6/2001 | Ouchi |
| 2001/0042643 A1 | 11/2001 | Krueger et al. |
| 2002/0019644 A1 | 2/2002 | Hastings |
| 2002/0045905 A1 | 4/2002 | Gerbi et al. |
| 2002/0098938 A1 | 7/2002 | Milbourne et al. |
| 2002/0100254 A1 | 8/2002 | Dharssi |
| 2002/0107573 A1 | 8/2002 | Steinberg |
| 2002/0111608 A1 | 8/2002 | Baerveldt |
| 2002/0111621 A1 | 8/2002 | Wallace et al. |
| 2002/0117017 A1 | 8/2002 | Bernhardt et al. |
| 2002/0161355 A1 | 10/2002 | Wollschlager |
| 2002/0161426 A1 | 10/2002 | Lancea |
| 2002/0177789 A1 | 11/2002 | Ferry et al. |
| 2003/0004455 A1 | 1/2003 | Kadziauskas |
| 2003/0036748 A1 | 2/2003 | Cooper et al. |
| 2003/0040681 A1 | 2/2003 | Ng et al. |
| 2003/0056561 A1 | 3/2003 | Butscher et al. |
| 2003/0065358 A1 | 4/2003 | Frecker |
| 2003/0100892 A1 | 5/2003 | Morley et al. |
| 2003/0109780 A1 | 6/2003 | Coste-Maniere et al. |
| 2003/0109877 A1 | 6/2003 | Morley |
| 2003/0109889 A1 | 6/2003 | Mercereau |
| 2003/0130564 A1 | 7/2003 | Martone et al. |
| 2003/0158545 A1 | 8/2003 | Hovda et al. |
| 2003/0163199 A1 | 8/2003 | Chu et al. |
| 2003/0167623 A1 | 9/2003 | Lorenz |
| 2003/0195664 A1 | 10/2003 | Nowlin et al. |
| 2003/0208189 A1 | 11/2003 | Payman |
| 2003/0212308 A1 | 11/2003 | Bendall |
| 2004/0015053 A1 | 1/2004 | Bieger |
| 2004/0015122 A1 | 1/2004 | Zhang et al. |
| 2004/0054322 A1 | 3/2004 | Vargas |

(56) References Cited

U.S. PATENT DOCUMENTS

| | | |
|---|---|---|
| 2004/0072066 A1 | 4/2004 | Cho et al. |
| 2004/0138525 A1 | 7/2004 | Saadat et al. |
| 2004/0143253 A1 | 7/2004 | Vanney |
| 2004/0152972 A1 | 8/2004 | Hunter |
| 2004/0153093 A1 | 8/2004 | Donovan |
| 2004/0158261 A1 | 8/2004 | Vu |
| 2004/0186349 A1 | 9/2004 | Ewers |
| 2004/0193013 A1 | 9/2004 | Isakawa et al. |
| 2004/0193146 A1 | 9/2004 | Lee et al. |
| 2004/0210116 A1 | 10/2004 | Nakao |
| 2004/0243147 A1 | 12/2004 | Lipow |
| 2004/0249246 A1 | 12/2004 | Campos |
| 2004/0253079 A1 | 12/2004 | Sanchez |
| 2004/0254566 A1 | 12/2004 | Plicchi |
| 2005/0004515 A1 | 1/2005 | Hart et al. |
| 2005/0004579 A1 | 1/2005 | Schneider et al. |
| 2005/0033270 A1 | 2/2005 | Ramans et al. |
| 2005/0054900 A1 | 3/2005 | Mawn |
| 2005/0125005 A1 | 6/2005 | Fujikura |
| 2005/0131279 A1 | 6/2005 | Boulais et al. |
| 2005/0154262 A1 | 7/2005 | Banik et al. |
| 2005/0159645 A1 | 7/2005 | Bertolero |
| 2005/0159646 A1 | 7/2005 | Nordstrom et al. |
| 2005/0165366 A1 | 7/2005 | Brustad |
| 2005/0177026 A1 | 8/2005 | Hoeg et al. |
| 2005/0183532 A1 | 8/2005 | Najaf et al. |
| 2005/0222554 A1 | 10/2005 | Wallace et al. |
| 2005/0222581 A1 | 10/2005 | Fischer et al. |
| 2005/0234293 A1 | 10/2005 | Yamamoto |
| 2005/0240178 A1 | 10/2005 | Morley et al. |
| 2005/0256452 A1 | 11/2005 | DeMarchi |
| 2005/0261705 A1 | 11/2005 | Gist |
| 2005/0272975 A1 | 12/2005 | McWeeney et al. |
| 2005/0273085 A1 | 12/2005 | Hinman et al. |
| 2005/0288549 A1 | 12/2005 | Mathis |
| 2006/0015133 A1 | 1/2006 | Grayzel |
| 2006/0041188 A1 | 2/2006 | Dirusso et al. |
| 2006/0041245 A1 | 2/2006 | Ferry |
| 2006/0058813 A1 | 3/2006 | Teague |
| 2006/0111692 A1 | 5/2006 | Hlavka et al. |
| 2006/0116693 A1 | 6/2006 | Weisenburgh |
| 2006/0135963 A1 | 6/2006 | Kick |
| 2006/0142657 A1 | 6/2006 | Quaid |
| 2006/0146010 A1 | 7/2006 | Schneider |
| 2006/0156875 A1 | 7/2006 | McRury et al. |
| 2006/0161137 A1 | 7/2006 | Orban et al. |
| 2006/0189891 A1 | 8/2006 | Waxman et al. |
| 2006/0201688 A1 | 9/2006 | Jenner et al. |
| 2006/0229587 A1 | 10/2006 | Beyar et al. |
| 2006/0237205 A1 | 10/2006 | Sia et al. |
| 2006/0241368 A1 | 10/2006 | Fichtinger et al. |
| 2006/0264708 A1 | 11/2006 | Horne |
| 2006/0276827 A1 | 12/2006 | Mitelberg et al. |
| 2006/0287769 A1 | 12/2006 | Yanagita et al. |
| 2007/0000498 A1 | 1/2007 | Glynn et al. |
| 2007/0013336 A1 | 1/2007 | Nowlin et al. |
| 2007/0016164 A1 | 1/2007 | Dudney et al. |
| 2007/0027443 A1 | 2/2007 | Rose |
| 2007/0027534 A1 | 2/2007 | Bergheim |
| 2007/0032906 A1 | 2/2007 | Sutherland et al. |
| 2007/0054766 A1 | 3/2007 | Shamis et al. |
| 2007/0060879 A1 | 3/2007 | Weitzner et al. |
| 2007/0100201 A1 | 5/2007 | Komiya et al. |
| 2007/0100254 A1 | 5/2007 | Murakami |
| 2007/0106304 A1 | 5/2007 | Hammack |
| 2007/0112355 A1 | 5/2007 | Salahieh |
| 2007/0117655 A1 | 5/2007 | Kasashima et al. |
| 2007/0119274 A1 | 5/2007 | Devengenzo et al. |
| 2007/0123855 A1 | 5/2007 | Morley et al. |
| 2007/0135733 A1 | 6/2007 | Soukup et al. |
| 2007/0135763 A1 | 6/2007 | Musbach et al. |
| 2007/0135803 A1 | 6/2007 | Belson |
| 2007/0149946 A1 | 6/2007 | Viswanathan |
| 2007/0156019 A1 | 7/2007 | Larkin et al. |
| 2007/0185485 A1 | 8/2007 | Hauck et al. |
| 2007/0191177 A1 | 8/2007 | Nagai et al. |
| 2007/0208375 A1 | 9/2007 | Nishizawa |
| 2007/0213668 A1 | 9/2007 | Spitz |
| 2007/0239028 A1 | 10/2007 | Houser |
| 2007/0239178 A1 | 10/2007 | Weitzner et al. |
| 2007/0245175 A1 | 10/2007 | Zheng et al. |
| 2007/0250111 A1 | 10/2007 | Lu |
| 2007/0270645 A1 | 11/2007 | Ikeda |
| 2007/0270679 A1 | 11/2007 | Nguyen et al. |
| 2007/0282167 A1 | 12/2007 | Barenboym et al. |
| 2007/0287886 A1 | 12/2007 | Saadat |
| 2007/0299427 A1 | 12/2007 | Yeung et al. |
| 2008/0015566 A1 | 1/2008 | Livneh |
| 2008/0021440 A1 | 1/2008 | Solomon |
| 2008/0033467 A1 | 2/2008 | Miyamoto et al. |
| 2008/0039255 A1 | 2/2008 | Jinno et al. |
| 2008/0045981 A1 | 2/2008 | Margolin et al. |
| 2008/0046122 A1 | 2/2008 | Manzo et al. |
| 2008/0051629 A1 | 2/2008 | Sugiyama et al. |
| 2008/0065103 A1 | 3/2008 | Cooper et al. |
| 2008/0065111 A1 | 3/2008 | Blumenkranz |
| 2008/0065112 A1 | 3/2008 | Tovey et al. |
| 2008/0097293 A1 | 4/2008 | Chin et al. |
| 2008/0108869 A1 | 5/2008 | Sanders et al. |
| 2008/0125698 A1 | 5/2008 | Greg et al. |
| 2008/0139887 A1 | 6/2008 | Fitpatrick |
| 2008/0146874 A1 | 6/2008 | Miller |
| 2008/0147011 A1 | 6/2008 | Urmey |
| 2008/0147089 A1 | 6/2008 | Loh |
| 2008/0177285 A1 | 7/2008 | Brock et al. |
| 2008/0187101 A1 | 8/2008 | Gertner |
| 2008/0196533 A1 | 8/2008 | Bergamasco |
| 2008/0208001 A1 | 8/2008 | Hadani |
| 2008/0212082 A1 | 9/2008 | Froggatt et al. |
| 2008/0214925 A1 | 9/2008 | Wilson et al. |
| 2008/0218770 A1 | 9/2008 | Moll et al. |
| 2008/0228104 A1 | 9/2008 | Uber et al. |
| 2008/0243064 A1 | 10/2008 | Stahler et al. |
| 2008/0249536 A1 | 10/2008 | Stahler et al. |
| 2008/0253108 A1 | 10/2008 | Yu et al. |
| 2008/0262301 A1 | 10/2008 | Gibbons et al. |
| 2008/0287963 A1 | 11/2008 | Rogers et al. |
| 2008/0302200 A1 | 12/2008 | Tobey |
| 2009/0005768 A1 | 1/2009 | Sharareh |
| 2009/0012507 A1 | 1/2009 | Culbertson et al. |
| 2009/0030446 A1 | 1/2009 | Measamer |
| 2009/0036900 A1 | 2/2009 | Moll |
| 2009/0043305 A1 | 2/2009 | Brodbeck |
| 2009/0082634 A1 | 3/2009 | Kathrani et al. |
| 2009/0082722 A1 | 3/2009 | Munger et al. |
| 2009/0088774 A1 | 4/2009 | Swarup et al. |
| 2009/0098971 A1 | 4/2009 | Ho et al. |
| 2009/0099420 A1 | 4/2009 | Woodley et al. |
| 2009/0105645 A1 | 4/2009 | Kidd et al. |
| 2009/0105723 A1 | 4/2009 | Dillinger |
| 2009/0131885 A1 | 5/2009 | Akahoshi |
| 2009/0137353 A1 | 5/2009 | Serkh |
| 2009/0161827 A1 | 6/2009 | Gertner et al. |
| 2009/0163851 A1 | 6/2009 | Holloway |
| 2009/0163948 A1 | 6/2009 | Sunaoshi |
| 2009/0171371 A1 | 7/2009 | Nixon |
| 2009/0192524 A1 | 7/2009 | Ltkowitz |
| 2009/0227998 A1 | 9/2009 | Aljuri |
| 2009/0247880 A1 | 10/2009 | Naruse et al. |
| 2009/0247944 A1 | 10/2009 | Kirschenman et al. |
| 2009/0248039 A1 | 10/2009 | Cooper et al. |
| 2009/0248041 A1 | 10/2009 | Williams et al. |
| 2009/0248043 A1 | 10/2009 | Tierney et al. |
| 2009/0254083 A1 | 10/2009 | Wallace et al. |
| 2009/0264878 A1 | 10/2009 | Carmel et al. |
| 2009/0270760 A1 | 10/2009 | Leimbach et al. |
| 2009/0287188 A1 | 11/2009 | Golden et al. |
| 2009/0299344 A1 | 12/2009 | Lee et al. |
| 2009/0299352 A1 | 12/2009 | Zerfas |
| 2009/0306587 A1 | 12/2009 | Milijasevic et al. |
| 2009/0312773 A1 | 12/2009 | Cabrera et al. |
| 2010/0004642 A1 | 1/2010 | Lumpkin |
| 2010/0010504 A1 | 1/2010 | Simaan et al. |
| 2010/0011900 A1 | 1/2010 | Burbank |

(56) References Cited

U.S. PATENT DOCUMENTS

| | | |
|---|---|---|
| 2010/0011901 A1 | 1/2010 | Burbank |
| 2010/0016852 A1 | 1/2010 | Manzo et al. |
| 2010/0016853 A1 | 1/2010 | Burbank |
| 2010/0030023 A1 | 2/2010 | Yoshie |
| 2010/0069833 A1 | 3/2010 | Wenderow et al. |
| 2010/0073150 A1 | 3/2010 | Olson et al. |
| 2010/0081965 A1 | 4/2010 | Mugan et al. |
| 2010/0082017 A1 | 4/2010 | Zickler |
| 2010/0082041 A1 | 4/2010 | Prisco |
| 2010/0114115 A1 | 5/2010 | Schlesinger et al. |
| 2010/0130823 A1 | 5/2010 | Ando |
| 2010/0130923 A1 | 5/2010 | Cleary et al. |
| 2010/0130987 A1 | 5/2010 | Wenderow et al. |
| 2010/0168918 A1 | 7/2010 | Zhao |
| 2010/0175701 A1 | 7/2010 | Reis et al. |
| 2010/0179632 A1 | 7/2010 | Bruszewski et al. |
| 2010/0204605 A1 | 8/2010 | Blakley |
| 2010/0204646 A1 | 8/2010 | Plicchi et al. |
| 2010/0210923 A1 | 8/2010 | Li et al. |
| 2010/0217184 A1 | 8/2010 | Koblish et al. |
| 2010/0217235 A1 | 8/2010 | Thorstenson |
| 2010/0225209 A1 | 9/2010 | Goldberg |
| 2010/0228249 A1 | 9/2010 | Mohr |
| 2010/0234831 A1 | 9/2010 | Hinman et al. |
| 2010/0248177 A1 | 9/2010 | Mangelberger et al. |
| 2010/0249497 A1 | 9/2010 | Peine et al. |
| 2010/0249506 A1 | 9/2010 | Prisco et al. |
| 2010/0268211 A1 | 10/2010 | Manwaring et al. |
| 2010/0274078 A1 | 10/2010 | Kim et al. |
| 2010/0312141 A1 | 12/2010 | Keast et al. |
| 2010/0331858 A1 | 12/2010 | Simaan et al. |
| 2010/0332033 A1 | 12/2010 | Diolaiti |
| 2011/0009863 A1 | 1/2011 | Stanislaw |
| 2011/0015483 A1 | 1/2011 | Barbagli |
| 2011/0015484 A1 | 1/2011 | Alvarez et al. |
| 2011/0015648 A1 | 1/2011 | Alvarez et al. |
| 2011/0015650 A1 | 1/2011 | Choi et al. |
| 2011/0028790 A1 | 2/2011 | Farr et al. |
| 2011/0028991 A1 | 2/2011 | Ikeda et al. |
| 2011/0046441 A1 | 2/2011 | Wiltshire et al. |
| 2011/0071541 A1 | 3/2011 | Prisco et al. |
| 2011/0071543 A1 | 3/2011 | Prisco et al. |
| 2011/0077681 A1 | 3/2011 | Nagano |
| 2011/0098533 A1 | 4/2011 | Onoda |
| 2011/0106146 A1 | 5/2011 | Jeong |
| 2011/0125165 A1 | 5/2011 | Simaan et al. |
| 2011/0130718 A1 | 6/2011 | Kidd et al. |
| 2011/0147030 A1 | 6/2011 | Blum et al. |
| 2011/0148442 A1 | 6/2011 | Berner |
| 2011/0152880 A1 | 6/2011 | Alvarez et al. |
| 2011/0160713 A1 | 6/2011 | Neuberger |
| 2011/0160745 A1 | 6/2011 | Fielding |
| 2011/0167611 A1 | 7/2011 | Williams |
| 2011/0184391 A1 | 7/2011 | Aljuri |
| 2011/0208211 A1 | 8/2011 | Whitfield et al. |
| 2011/0213362 A1 | 9/2011 | Cunningham |
| 2011/0224660 A1 | 9/2011 | Neuberger et al. |
| 2011/0238064 A1 | 9/2011 | Williams et al. |
| 2011/0238083 A1 | 9/2011 | Moll et al. |
| 2011/0245844 A1 | 10/2011 | Jinno et al. |
| 2011/0257641 A1 | 10/2011 | Hastings et al. |
| 2011/0261183 A1 | 10/2011 | Ma et al. |
| 2011/0276085 A1 | 11/2011 | Krzyzanowski |
| 2011/0277775 A1 | 11/2011 | Holop et al. |
| 2011/0288573 A1 | 11/2011 | Yates et al. |
| 2011/0306836 A1 | 12/2011 | Ohline et al. |
| 2011/0313343 A1 | 12/2011 | Milutinovic et al. |
| 2012/0004576 A1 | 1/2012 | Govari et al. |
| 2012/0048759 A1 | 3/2012 | Disch et al. |
| 2012/0069167 A1 | 3/2012 | Liu et al. |
| 2012/0071821 A1 | 3/2012 | Yu |
| 2012/0071894 A1 | 3/2012 | Tanner et al. |
| 2012/0071895 A1 | 3/2012 | Stahler et al. |
| 2012/0253277 A1 | 4/2012 | Tah et al. |
| 2012/0123327 A1 | 5/2012 | Miller |
| 2012/0132018 A1 | 5/2012 | Tang |
| 2012/0136419 A1 | 5/2012 | Zarembo et al. |
| 2012/0138586 A1 | 6/2012 | Webster et al. |
| 2012/0138660 A1 | 6/2012 | Shelton, IV et al. |
| 2012/0143226 A1 | 6/2012 | Belson et al. |
| 2012/0150154 A1 | 6/2012 | Brisson et al. |
| 2012/0186194 A1 | 7/2012 | Schlieper |
| 2012/0190976 A1 | 7/2012 | Kleinstreuer |
| 2012/0191107 A1 | 7/2012 | Tanner et al. |
| 2012/0209315 A1 | 8/2012 | Amat |
| 2012/0220832 A1 | 8/2012 | Nakade et al. |
| 2012/0232342 A1 | 9/2012 | Reydel |
| 2012/0232476 A1 | 9/2012 | Bhat et al. |
| 2012/0239012 A1 | 9/2012 | Laurent et al. |
| 2012/0253332 A1 | 10/2012 | Moll |
| 2012/0259244 A1 | 10/2012 | Roberts et al. |
| 2012/0259320 A1 | 10/2012 | Loesel et al. |
| 2012/0277730 A1 | 11/2012 | Salahieh |
| 2012/0283747 A1 | 11/2012 | Popovic |
| 2012/0289777 A1 | 11/2012 | Chopra |
| 2012/0296318 A1 | 11/2012 | Wellhofer et al. |
| 2013/0006144 A1 | 1/2013 | Clancy |
| 2013/0018400 A1 | 1/2013 | Milton et al. |
| 2013/0030519 A1 | 1/2013 | Tran et al. |
| 2013/0035537 A1 | 2/2013 | Wallace et al. |
| 2013/0053877 A1 | 2/2013 | BenMaamer |
| 2013/0066136 A1 | 3/2013 | Palese et al. |
| 2013/0066335 A1 | 3/2013 | Barwinkel |
| 2013/0085442 A1 | 4/2013 | Shtul et al. |
| 2013/0085486 A1 | 4/2013 | Boutoussov et al. |
| 2013/0090552 A1 | 4/2013 | Ramamurthy et al. |
| 2013/0096422 A1 | 4/2013 | Boctor |
| 2013/0096574 A1 | 4/2013 | Kang et al. |
| 2013/0109957 A1 | 5/2013 | Hooft et al. |
| 2013/0110042 A1 | 5/2013 | Humphreys |
| 2013/0110107 A1 | 5/2013 | Smith et al. |
| 2013/0116716 A1 | 5/2013 | Bahls et al. |
| 2013/0144116 A1 | 6/2013 | Cooper et al. |
| 2013/0144274 A1 | 6/2013 | Stefanchik et al. |
| 2013/0144395 A1 | 6/2013 | Stefanchik |
| 2013/0165854 A1 | 6/2013 | Sandhu et al. |
| 2013/0165908 A1 | 6/2013 | Purdy et al. |
| 2013/0190796 A1 | 7/2013 | Tilson et al. |
| 2013/0204124 A1 | 8/2013 | Duindam |
| 2013/0225997 A1 | 8/2013 | Dillard et al. |
| 2013/0226151 A1 | 8/2013 | Suehara |
| 2013/0226161 A1 | 8/2013 | Hickenbotham |
| 2013/0231678 A1 | 9/2013 | Wenderow |
| 2013/0233908 A1 | 9/2013 | Knodel |
| 2013/0253267 A1 | 9/2013 | Collins |
| 2013/0303876 A1 | 11/2013 | Gelfand et al. |
| 2013/0303892 A1 | 11/2013 | Zhao |
| 2013/0304084 A1 | 11/2013 | Beira et al. |
| 2013/0304091 A1 | 11/2013 | Straehnz |
| 2013/0310819 A1 | 11/2013 | Neuberger et al. |
| 2013/0317276 A1 | 11/2013 | D'Andrea |
| 2013/0317519 A1 | 11/2013 | Romo et al. |
| 2013/0334281 A1 | 12/2013 | Williams |
| 2013/0345519 A1 | 12/2013 | Piskun et al. |
| 2013/0345686 A1 | 12/2013 | Brown |
| 2014/0000411 A1 | 1/2014 | Shelton, IV et al. |
| 2014/0005681 A1 | 1/2014 | Gee et al. |
| 2014/0012288 A1 | 1/2014 | Darisse |
| 2014/0039517 A1 | 2/2014 | Bowling |
| 2014/0039681 A1 | 2/2014 | Bowling |
| 2014/0046308 A1 | 2/2014 | Bischoff |
| 2014/0046313 A1 | 2/2014 | Pederson et al. |
| 2014/0051985 A1 | 2/2014 | Fan et al. |
| 2014/0058365 A1 | 2/2014 | Bille |
| 2014/0058404 A1 | 2/2014 | Hammack |
| 2014/0058428 A1 | 2/2014 | Christopher |
| 2014/0066944 A1 | 3/2014 | Taylor et al. |
| 2014/0069437 A1 | 3/2014 | Reis et al. |
| 2014/0100445 A1 | 4/2014 | Stenzel |
| 2014/0142591 A1 | 5/2014 | Alvarez et al. |
| 2014/0163318 A1 | 6/2014 | Swanstrom |
| 2014/0163736 A1 | 6/2014 | Azizian |
| 2014/0166023 A1 | 6/2014 | Kishi |
| 2014/0171778 A1 | 6/2014 | Tsusaka |

(56) References Cited

U.S. PATENT DOCUMENTS

| | | |
|---|---|---|
| 2014/0180063 A1 | 6/2014 | Zhao |
| 2014/0194859 A1 | 7/2014 | Ianchulev |
| 2014/0194905 A1 | 7/2014 | Kappel |
| 2014/0200402 A1 | 7/2014 | Snoke et al. |
| 2014/0222019 A1 | 8/2014 | Brudnick |
| 2014/0222207 A1 | 8/2014 | Bowling et al. |
| 2014/0235943 A1 | 8/2014 | Paris |
| 2014/0243849 A1 | 8/2014 | Saglam et al. |
| 2014/0246473 A1 | 9/2014 | Auld |
| 2014/0257333 A1 | 9/2014 | Blumenkranz |
| 2014/0275956 A1 | 9/2014 | Fan |
| 2014/0276233 A1 | 9/2014 | Murphy |
| 2014/0276389 A1 | 9/2014 | Walker |
| 2014/0276394 A1 | 9/2014 | Wong et al. |
| 2014/0276594 A1 | 9/2014 | Tanner et al. |
| 2014/0276723 A1 | 9/2014 | Parihar |
| 2014/0276935 A1 | 9/2014 | Yu |
| 2014/0276936 A1 | 9/2014 | Kokish et al. |
| 2014/0276956 A1 | 9/2014 | Crainich |
| 2014/0277334 A1 | 9/2014 | Yu et al. |
| 2014/0309655 A1 | 10/2014 | Gal et al. |
| 2014/0316203 A1 | 10/2014 | Carroux et al. |
| 2014/0316397 A1 | 10/2014 | Brown |
| 2014/0343416 A1 | 11/2014 | Panescu |
| 2014/0357984 A1 | 12/2014 | Wallace et al. |
| 2014/0375784 A1 | 12/2014 | Massetti |
| 2015/0012134 A1 | 1/2015 | Robinson |
| 2015/0031950 A1 | 1/2015 | Drontle et al. |
| 2015/0073439 A1 | 3/2015 | Dannaher |
| 2015/0080879 A1 | 3/2015 | Trees |
| 2015/0090063 A1 | 4/2015 | Lantermann et al. |
| 2015/0127045 A1 | 5/2015 | Prestel |
| 2015/0133960 A1 | 5/2015 | Lohmeier |
| 2015/0133963 A1 | 5/2015 | Barbagli |
| 2015/0142013 A1 | 5/2015 | Tanner et al. |
| 2015/0144514 A1 | 5/2015 | Brennan et al. |
| 2015/0148600 A1 | 5/2015 | Ashinuma et al. |
| 2015/0150635 A1 | 6/2015 | Kilroy |
| 2015/0164522 A1 | 6/2015 | Budiman |
| 2015/0182250 A1 | 7/2015 | Conlon et al. |
| 2015/0190204 A1 | 7/2015 | Popovi |
| 2015/0201917 A1 | 7/2015 | Snow |
| 2015/0202085 A1 | 7/2015 | Lemonis |
| 2015/0231364 A1 | 8/2015 | Blanchard |
| 2015/0255782 A1 | 9/2015 | Kim et al. |
| 2015/0314110 A1 | 11/2015 | Park |
| 2015/0366629 A1 | 12/2015 | Bowling |
| 2015/0374445 A1 | 12/2015 | Gombert et al. |
| 2015/0374446 A1 | 12/2015 | Malackowski |
| 2016/0000414 A1 | 1/2016 | Brown |
| 2016/0000512 A1 | 1/2016 | Gombert et al. |
| 2016/0007881 A1 | 1/2016 | Wong et al. |
| 2016/0022289 A1 | 1/2016 | Wan |
| 2016/0022466 A1 | 1/2016 | Pedtke |
| 2016/0030014 A1 | 2/2016 | McWeeney et al. |
| 2016/0030073 A1 | 2/2016 | Isakov |
| 2016/0045208 A1 | 2/2016 | Ciulla |
| 2016/0051318 A1 | 2/2016 | Manzo et al. |
| 2016/0066935 A1 | 3/2016 | Nguyen et al. |
| 2016/0067450 A1 | 3/2016 | Kowshik |
| 2016/0128781 A1 | 5/2016 | Blohm et al. |
| 2016/0157945 A1 | 6/2016 | Madhani |
| 2016/0158490 A1 | 6/2016 | Leeflang |
| 2016/0166234 A1 | 6/2016 | Zhang |
| 2016/0183841 A1 | 6/2016 | Duindam et al. |
| 2016/0192860 A1 | 7/2016 | Allenby |
| 2016/0199984 A1 | 7/2016 | Lohmeier et al. |
| 2016/0206389 A1 | 7/2016 | Miller |
| 2016/0213435 A1 | 7/2016 | Hourtash |
| 2016/0227982 A1 | 8/2016 | Takahashi |
| 2016/0235495 A1 | 8/2016 | Wallace et al. |
| 2016/0242858 A1 | 8/2016 | Moctezuma de la Barrera et al. |
| 2016/0249932 A1 | 9/2016 | Rogers et al. |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0302871 A1 | 10/2016 | Gregerson et al. |
| 2016/0303743 A1 | 10/2016 | Rockrohr |
| 2016/0310146 A1 | 10/2016 | Levy et al. |
| 2016/0331358 A1 | 11/2016 | Gordon |
| 2016/0338783 A1 | 11/2016 | Romo et al. |
| 2016/0346049 A1 | 12/2016 | Allen et al. |
| 2016/0367324 A1 | 12/2016 | Sato et al. |
| 2016/0372743 A1 | 12/2016 | Cho et al. |
| 2017/0000577 A1 | 1/2017 | Bowling |
| 2017/0007337 A1 | 1/2017 | Dan |
| 2017/0020615 A1 | 1/2017 | Koenig et al. |
| 2017/0049471 A1 | 2/2017 | Gaffney et al. |
| 2017/0055995 A1 | 3/2017 | Weier |
| 2017/0065227 A1 | 3/2017 | Marrs |
| 2017/0071584 A1 | 3/2017 | Suigetsu et al. |
| 2017/0086934 A1 | 3/2017 | Devengenzo et al. |
| 2017/0095234 A1 | 4/2017 | Prisco et al. |
| 2017/0095295 A1 | 4/2017 | Overmyer |
| 2017/0135706 A1 | 5/2017 | Frey |
| 2017/0151028 A1 | 6/2017 | Ogawa et al. |
| 2017/0151416 A1 | 6/2017 | Kutikov |
| 2017/0165009 A1 | 6/2017 | Chaplin et al. |
| 2017/0172553 A1 | 6/2017 | Chaplin |
| 2017/0172680 A1 | 6/2017 | Bowling |
| 2017/0202627 A1 | 7/2017 | Sramek et al. |
| 2017/0209073 A1 | 7/2017 | Sramek et al. |
| 2017/0252096 A1 | 9/2017 | Felder |
| 2017/0258534 A1 | 9/2017 | Hourtash et al. |
| 2017/0265923 A1 | 9/2017 | Privitera |
| 2017/0265954 A1 | 9/2017 | Burbank |
| 2017/0281049 A1 | 10/2017 | Yamamoto |
| 2017/0281218 A1 | 10/2017 | Timm |
| 2017/0290631 A1 | 10/2017 | Lee et al. |
| 2017/0319289 A1 | 11/2017 | Neff et al. |
| 2017/0325932 A1 | 11/2017 | Hoelzle |
| 2017/0333147 A1 | 11/2017 | Bernstein |
| 2018/0000563 A1 | 1/2018 | Shanjani et al. |
| 2018/0025666 A1 | 1/2018 | Ho et al. |
| 2018/0042464 A1 | 2/2018 | Arai |
| 2018/0042686 A1 | 2/2018 | Peine |
| 2018/0049792 A1 | 2/2018 | Eckert |
| 2018/0049824 A1 | 2/2018 | Harris |
| 2018/0056044 A1 | 3/2018 | Choi et al. |
| 2018/0079090 A1 | 3/2018 | Koenig et al. |
| 2018/0080841 A1 | 3/2018 | Cordoba |
| 2018/0104820 A1 | 4/2018 | Troy et al. |
| 2018/0116735 A1 | 5/2018 | Tierney et al. |
| 2018/0140371 A1 | 5/2018 | Hares et al. |
| 2018/0193049 A1 | 7/2018 | Heck et al. |
| 2018/0206927 A1 | 7/2018 | Prisco et al. |
| 2018/0206931 A1 | 7/2018 | Scheib |
| 2018/0221038 A1 | 8/2018 | Noonan et al. |
| 2018/0221039 A1 | 8/2018 | Shah |
| 2018/0243048 A1 | 8/2018 | Shan |
| 2018/0250085 A1 | 9/2018 | Simi |
| 2018/0279852 A1 | 10/2018 | Rafii-Tari et al. |
| 2018/0289431 A1 | 10/2018 | Draper et al. |
| 2018/0296285 A1 | 10/2018 | Simi et al. |
| 2018/0296299 A1 | 10/2018 | Iceman |
| 2018/0303566 A1 | 10/2018 | Soundararajan |
| 2018/0325499 A1 | 11/2018 | Landey et al. |
| 2018/0326181 A1 | 11/2018 | Kokish et al. |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0015166 A1 | 1/2019 | Mahoney |
| 2019/0069962 A1 | 3/2019 | Tabandeh et al. |
| 2019/0099231 A1 | 4/2019 | Bruehwiler |
| 2019/0099232 A1 | 4/2019 | Soto et al. |
| 2019/0110839 A1 | 4/2019 | Rafii-Tari et al. |
| 2019/0117320 A1 | 4/2019 | Shoham et al. |
| 2019/0117324 A1 | 4/2019 | Hibner |
| 2019/0151148 A1 | 4/2019 | Alvarez et al. |
| 2019/0142537 A1 | 5/2019 | Covington et al. |
| 2019/0167366 A1 | 6/2019 | Ummalaneni |
| 2019/0175009 A1 | 6/2019 | Mintz |
| 2019/0183585 A1 | 6/2019 | Rafii-Tari et al. |

(56) References Cited

U.S. PATENT DOCUMENTS

| | | |
|---|---|---|
| 2019/0183587 A1 | 6/2019 | Rafii-Tari et al. |
| 2019/0192249 A1 | 6/2019 | Bowling |
| 2019/0216548 A1 | 7/2019 | Ummalaneni |
| 2019/0216576 A1 | 7/2019 | Eyre |
| 2019/0223967 A1 | 7/2019 | Abbott |
| 2019/0223974 A1 | 7/2019 | Romo |
| 2019/0231458 A1 | 8/2019 | DiMaio |
| 2019/0231460 A1 | 8/2019 | DiMaio |
| 2019/0239890 A1 | 8/2019 | Stokes |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298460 A1 | 10/2019 | Al-Jadda |
| 2019/0298464 A1 | 10/2019 | Abbott |
| 2019/0298465 A1 | 10/2019 | Chin |
| 2019/0298469 A1 | 10/2019 | Ramstad et al. |
| 2019/0307987 A1 | 10/2019 | Yu |
| 2019/0314616 A1 | 10/2019 | Moll et al. |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0375383 A1 | 12/2019 | Alvarez |
| 2019/0380787 A1 | 12/2019 | Ye |
| 2019/0380797 A1 | 12/2019 | Yu |
| 2020/0000533 A1 | 1/2020 | Schuh |
| 2020/0008874 A1 | 1/2020 | Barbagli et al. |
| 2020/0030046 A1 | 1/2020 | Bowling |
| 2020/0038123 A1 | 2/2020 | Graetzel |
| 2020/0038128 A1 | 2/2020 | Joseph |
| 2020/0039086 A1 | 2/2020 | Meyer |
| 2020/0046434 A1 | 2/2020 | Graetzel |
| 2020/0046942 A1 | 2/2020 | Alvarez |
| 2020/0085516 A1 | 3/2020 | DeFonzo |
| 2020/0086087 A1 | 3/2020 | Hart et al. |
| 2020/0091799 A1 | 3/2020 | Covington et al. |
| 2020/0093549 A1 | 3/2020 | Chin |
| 2020/0093554 A1 | 3/2020 | Schuh |
| 2020/0100855 A1 | 4/2020 | Leparmentier |
| 2020/0107894 A1 | 4/2020 | Wallace |
| 2020/0121502 A1 | 4/2020 | Kintz |
| 2020/0129252 A1 | 4/2020 | Kokish |
| 2020/0138531 A1 | 5/2020 | Chaplin |
| 2020/0146769 A1 | 5/2020 | Eyre |
| 2020/0155245 A1 | 5/2020 | Yu |
| 2020/0155801 A1 | 5/2020 | Kokish |
| 2020/0163726 A1 | 5/2020 | Tanner |
| 2020/0170720 A1 | 6/2020 | Ummalaneni |
| 2020/0171660 A1 | 6/2020 | Ho |
| 2020/0188043 A1 | 6/2020 | Yu |
| 2020/0197109 A1 | 6/2020 | Chaplin |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0230360 A1 | 7/2020 | Yu |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |
| 2020/0281787 A1 | 9/2020 | Ruiz |
| 2020/0297437 A1 | 9/2020 | Schuh |
| 2020/0297444 A1 | 9/2020 | Camarillo |
| 2020/0305983 A1 | 10/2020 | Yampolsky |
| 2020/0305989 A1 | 10/2020 | Schuh |
| 2020/0305992 A1 | 10/2020 | Schuh |
| 2020/0315717 A1 | 10/2020 | Bovay |
| 2020/0315723 A1 | 10/2020 | Hassan |
| 2020/0323596 A1 | 10/2020 | Moll |
| 2020/0330167 A1 | 10/2020 | Romo |
| 2020/0337593 A1 | 10/2020 | Wong |
| 2020/0345216 A1 | 11/2020 | Jenkins |
| 2020/0352420 A1 | 11/2020 | Graetzel |
| 2020/0360183 A1 | 11/2020 | Alvarez |
| 2020/0367726 A1 | 11/2020 | Landey et al. |
| 2020/0367981 A1 | 11/2020 | Ho et al. |
| 2020/0375678 A1 | 12/2020 | Wallace |
| 2020/0383735 A1 | 12/2020 | Lewis et al. |
| 2020/0405317 A1 | 12/2020 | Wallace |
| 2020/0405411 A1 | 12/2020 | Draper et al. |
| 2020/0405413 A1 | 12/2020 | Kokish |
| 2020/0405419 A1 | 12/2020 | Mao |
| 2020/0405420 A1 | 12/2020 | Purohit |
| 2020/0405423 A1 | 12/2020 | Schuh |
| 2020/0405424 A1 | 12/2020 | Schuh |
| 2020/0405434 A1 | 12/2020 | Schuh |
| 2020/0406002 A1 | 12/2020 | Romo |

FOREIGN PATENT DOCUMENTS

| | | |
|---|---|---|
| CN | 101161426 | 4/2008 |
| CN | 101443069 | 5/2009 |
| CN | 100515347 | 7/2009 |
| CN | 103037799 | 4/2011 |
| CN | 201884596 U | 6/2011 |
| CN | 102316817 | 1/2012 |
| CN | 102327118 | 1/2012 |
| CN | 102458295 | 5/2012 |
| CN | 102665590 | 9/2012 |
| CN | 102711586 | 10/2012 |
| CN | 102834043 | 12/2012 |
| CN | 102973317 | 3/2013 |
| CN | 102015759 | 4/2013 |
| CN | 103298414 | 9/2013 |
| CN | 103735313 | 4/2014 |
| CN | 103767659 | 5/2014 |
| CN | 103930063 | 7/2014 |
| CN | 104619281 | 5/2015 |
| CN | 105147393 | 12/2015 |
| CN | 105559850 | 5/2016 |
| CN | 105559886 | 5/2016 |
| CN | 205729413 | 11/2016 |
| DE | 19649082 | 1/1998 |
| DE | 102004020465 | 9/2005 |
| EP | 0 543 539 | 5/1993 |
| EP | 0 776 739 | 6/1997 |
| EP | 1 321 106 | 6/2003 |
| EP | 1 442 720 | 8/2004 |
| EP | 0 904 796 | 11/2004 |
| EP | 1 849 423 | 10/2007 |
| EP | 2 567 670 | 3/2013 |
| EP | 3 025 630 | 6/2016 |
| JP | 07-136173 | 5/1995 |
| JP | 2005-270464 | 10/2005 |
| JP | 2006-525087 | 11/2006 |
| JP | 2007-511247 | 5/2007 |
| JP | 2009-139187 | 6/2009 |
| JP | 2010-046384 | 3/2010 |
| JP | 2011-015992 | 1/2011 |
| JP | 2011143029 A | 7/2011 |
| JP | 2012-105793 | 6/2012 |
| JP | 2014-159071 | 9/2014 |
| JP | 2015-181495 | 10/2015 |
| JP | 2018515299 A | 6/2018 |
| WO | WO 94/14494 | 7/1994 |
| WO | 9823216 A1 | 6/1998 |
| WO | WO 00/67640 | 11/2000 |
| WO | WO 02/74178 | 9/2002 |
| WO | WO 04/039273 | 5/2004 |
| WO | 2004096015 A2 | 11/2004 |
| WO | 2004103430 A2 | 12/2004 |
| WO | WO 04/105849 | 12/2004 |
| WO | WO 05/032637 | 4/2005 |
| WO | 2004114037 A3 | 9/2005 |
| WO | WO 05/081202 | 9/2005 |
| WO | WO 09/097461 | 6/2007 |
| WO | 2007136984 A2 | 11/2007 |
| WO | WO 07/146987 | 12/2007 |
| WO | WO 08/097540 | 8/2008 |
| WO | WO 09/092059 | 7/2009 |
| WO | 2009109532 A9 | 3/2010 |
| WO | WO 10/081187 | 7/2010 |

(56) References Cited

FOREIGN PATENT DOCUMENTS

| WO | 2010093153 A2 | 8/2010 | | |
|----|----|----|----|----|
| WO | 2010133733 A1 | 11/2010 | | |
| WO | WO 10/133982 | 11/2010 | | |
| WO | WO 11/005335 | 1/2011 | | |
| WO | 2011058530 A1 | 5/2011 | | |
| WO | 2011100110 A1 | 8/2011 | | |
| WO | WO 11/161218 | 12/2011 | | |
| WO | 2012018816 A2 | 2/2012 | | |
| WO | 2012035923 A1 | 3/2012 | | |
| WO | 2012040233 A2 | 3/2012 | | |
| WO | WO 12/037506 | 3/2012 | | |
| WO | 2013071071 A1 | 5/2013 | | |
| WO | WO 13/107468 | 7/2013 | | |
| WO | 2013154708 A1 | 10/2013 | | |
| WO | WO 13/179600 | 12/2013 | | |
| WO | WO 15/093602 | 12/2013 | | |
| WO | WO-2015016499 A1 * | 2/2015 | ............... | F16H 9/10 |
| WO | WO 15/127231 | 8/2015 | | |
| WO | WO 15/153174 | 10/2015 | | |
| WO | WO 16/003052 | 1/2016 | | |
| WO | WO 16/137612 | 9/2016 | | |
| WO | 2016161449 A1 | 10/2016 | | |
| WO | WO 17/059412 | 4/2017 | | |
| WO | WO 17/114855 | 7/2017 | | |
| WO | WO 17/151993 | 9/2017 | | |
| WO | WO 18/069679 | 4/2018 | | |
| WO | WO 18/189722 | 10/2018 | | |

OTHER PUBLICATIONS

Hernansanz et al, 2015, A multi-robot cooperation strategy for dexterous task oriented teleoperation, 2015, Elsevier, Robotics and Autonomous Systems, 68(205):156-172.

Ramezanifard et al, 2007, A Novel Modeling Approach for Collision Avoidance in Robotic Surgery, 2007 Science Publications, American Journal of Applied Sciences 4(9):693-699.

Mayo Clinic, Robotic Surgery, https://www.mayoclinic.org/tests-procedures/robotic-surgery/about/pac-20394974?p=1, downloaded from the internet on Jul. 12. 2018, 2 pp.

International search report for PCT/IB2020/062353, dated Apr. 5, 2021, 4 pages.

Written opinion of the International Search Report for PCT/IB2020/062353, dated Apr. 5, 2021, 6 pages.

Search Report and Written Opinion for Appl. No. 20909838.3, dated Jan. 12, 2024, 10 pages.

* cited by examiner

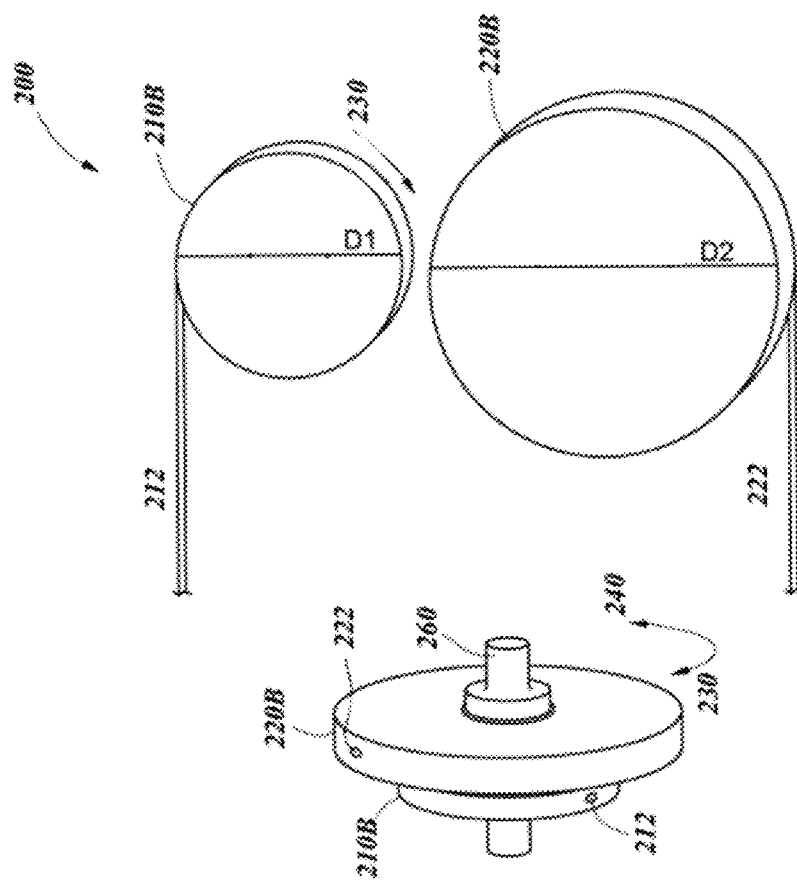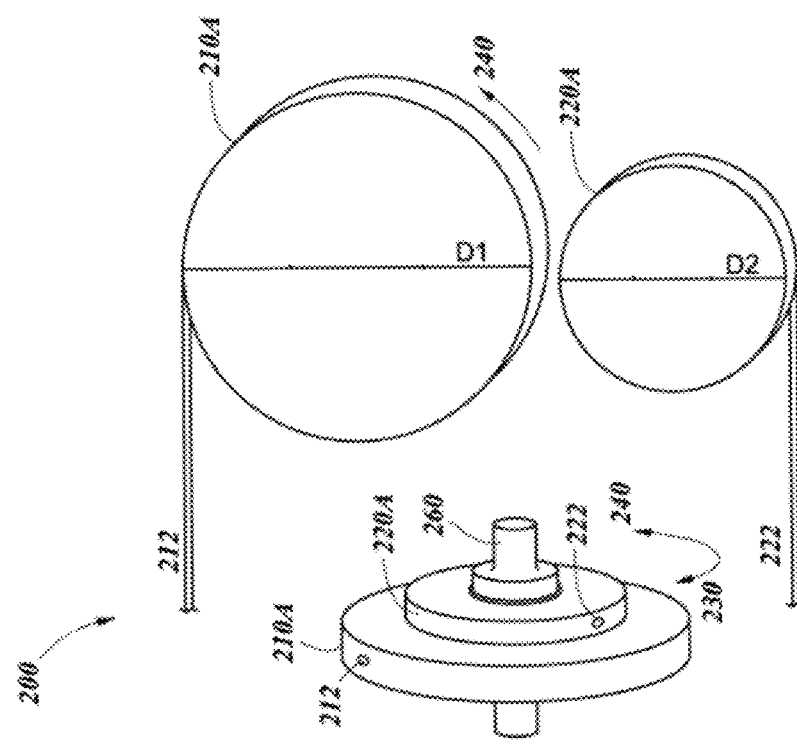

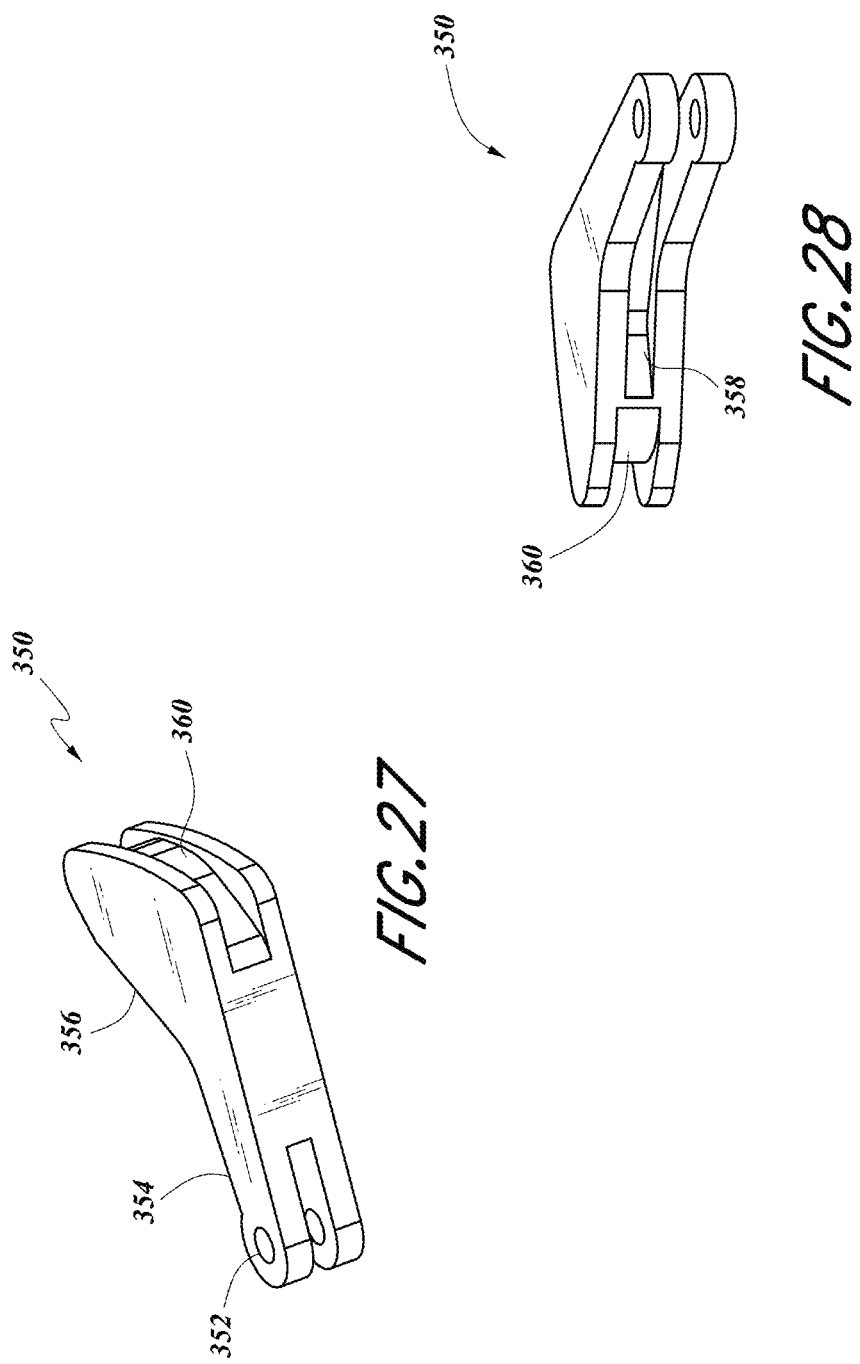

DYNAMIC PULLEY SYSTEM

CROSS-REFERENCE TO RELATED APPLICATION(S)

This application claims the benefit of U.S. Provisional Application No. 62/956,001, filed Dec. 31, 2019, which is hereby incorporated by reference in its entirety.

TECHNICAL FIELD

Systems and methods disclosed herein are directed to medical instrument systems, and more particularly, to a dynamic pulley system for robotic medical procedures.

BACKGROUND

Medical procedures, such as endoscopy, may involve accessing and visualizing the inside of a patient's anatomy for diagnostic and/or therapeutic purposes. For example, gastroenterology, urology, and bronchology involve medical procedures that allow a physician to examine patient lumens, such as the ureter, gastrointestinal tract, and airways (bronchi and bronchioles). During these procedures, a thin, flexible tubular tool or instrument, such as an endoscope or catheter, is inserted into the patient through an orifice (such as a natural orifice) and advanced towards a tissue site identified for subsequent diagnosis and/or treatment. The medical instrument can be controllable and articulable to facilitate navigation through the anatomy.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 21A illustrates a dynamic pulley system with two pulleys coupled together in a first configuration.

FIG. 21B illustrates the two pulleys of the dynamic pulley system of FIG. 21A positioned side by side in the first configuration.

FIG. 22A illustrates two expandable pulleys of the dynamic pulley system of FIG. 21A coupled together in a second configuration.

FIG. 22B illustrates the dynamic pulley system of FIGS. 21A-22A positioned side by side in the second configuration.

FIG. 27 illustrates a perspective top view of a leaf of the dynamic pulley system of FIGS. 23-26.

FIG. 28 illustrate a perspective side view of the leaf of FIG. 27.

DETAILED DESCRIPTION

1. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart

Figure 1:
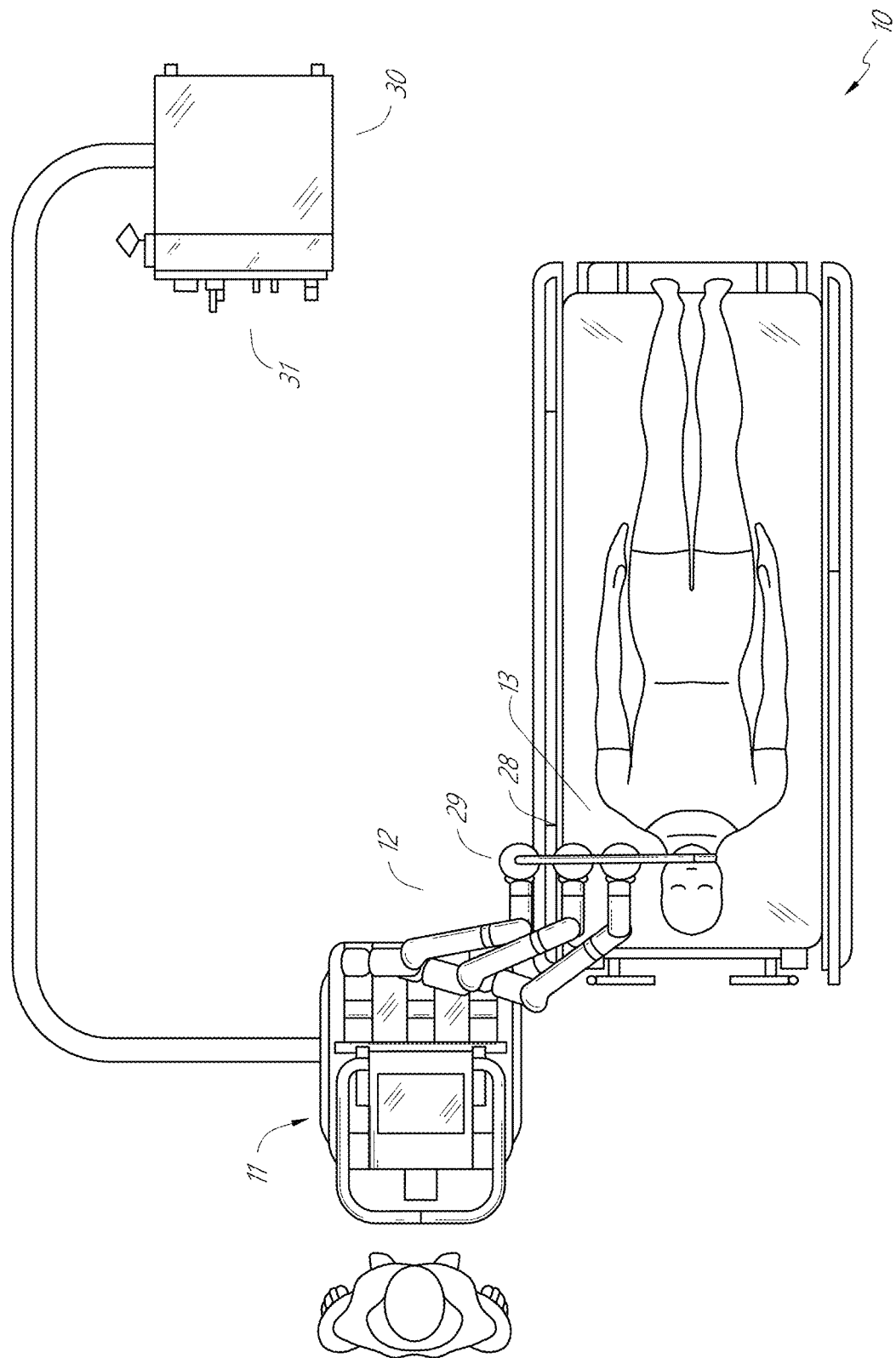
FIG. 1 illustrates an embodiment of a cart-based robotic system arranged for diagnostic and/or therapeutic bronchoscopy.
Figure 2:
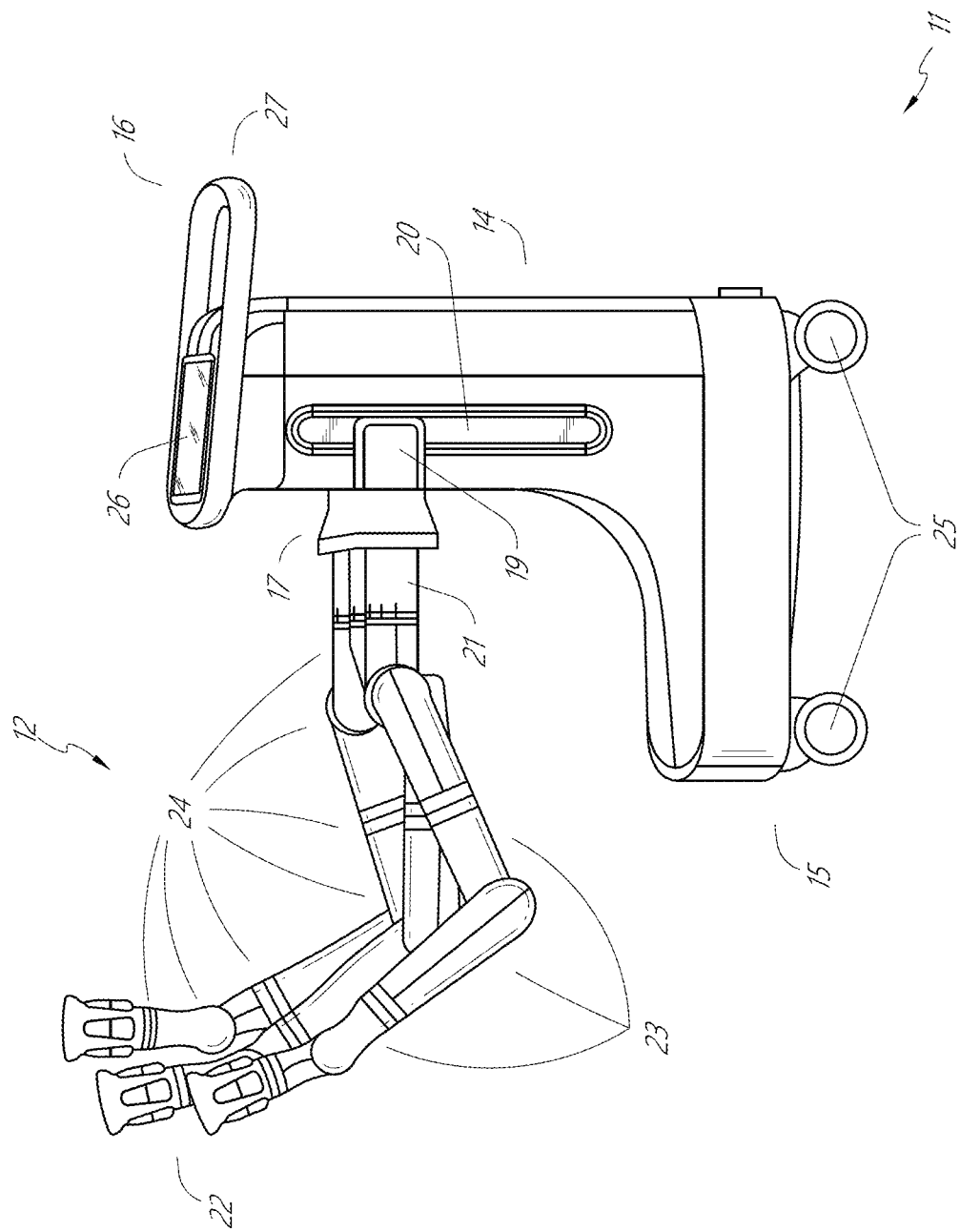
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
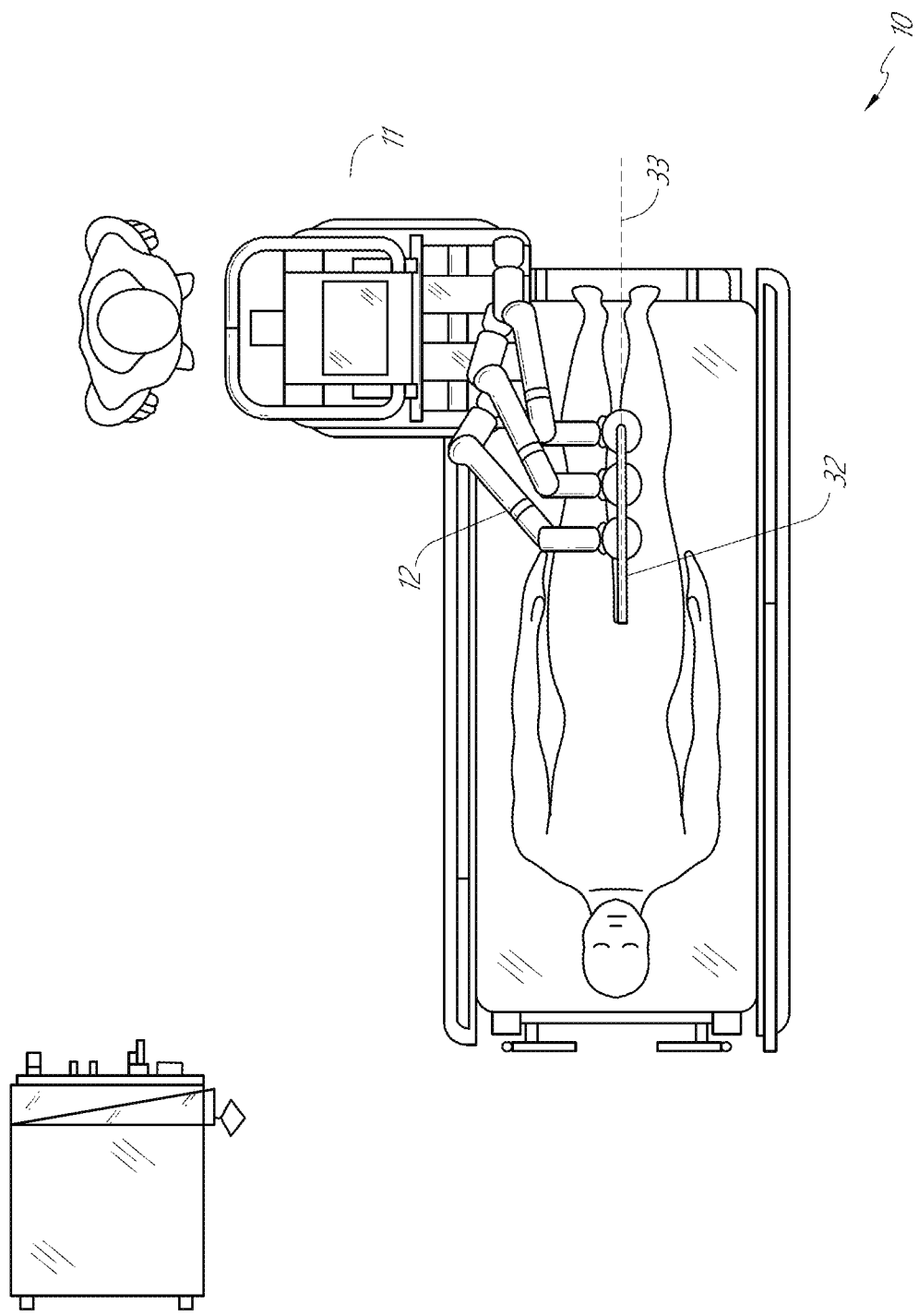
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
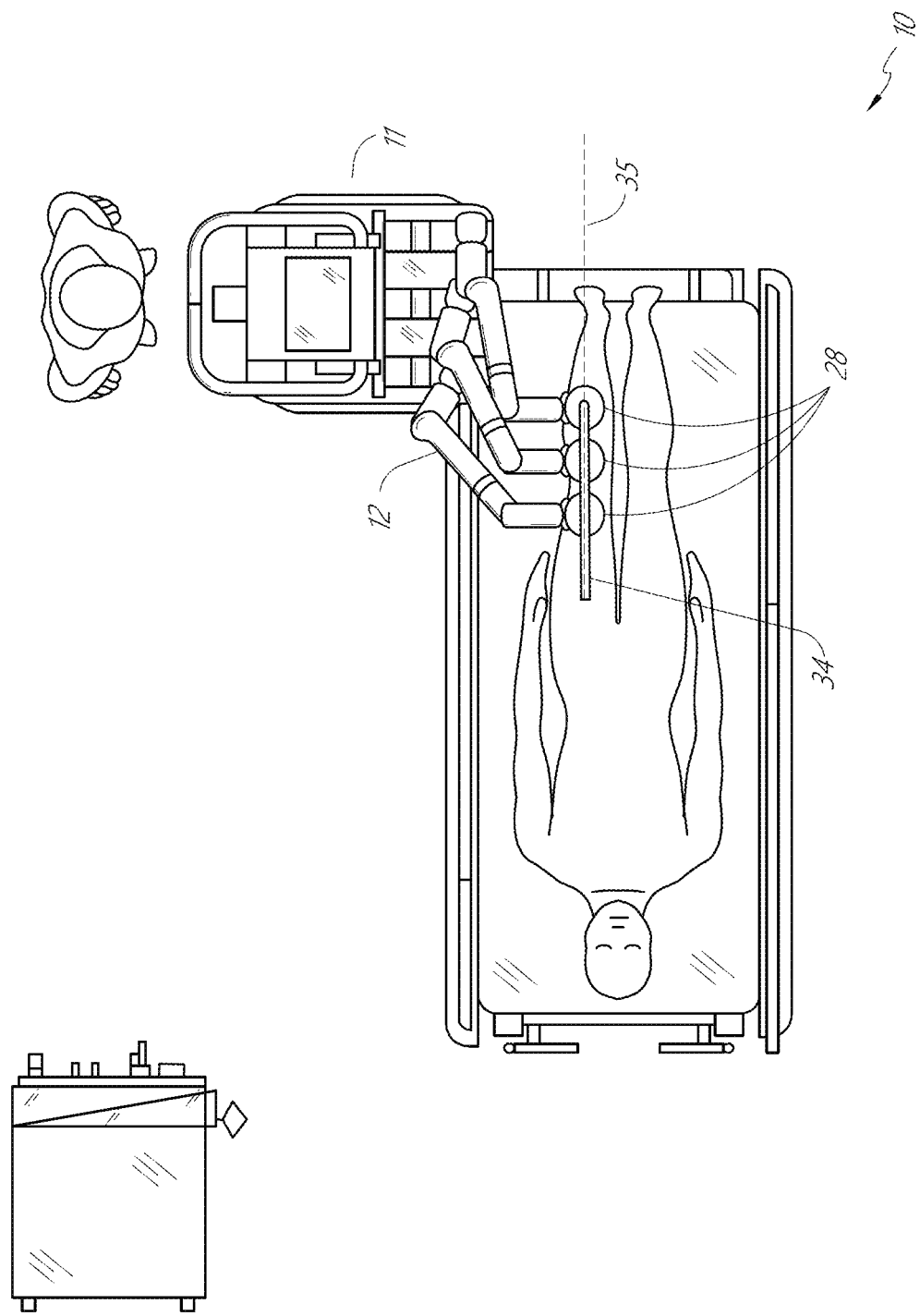
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table

Figure 5:
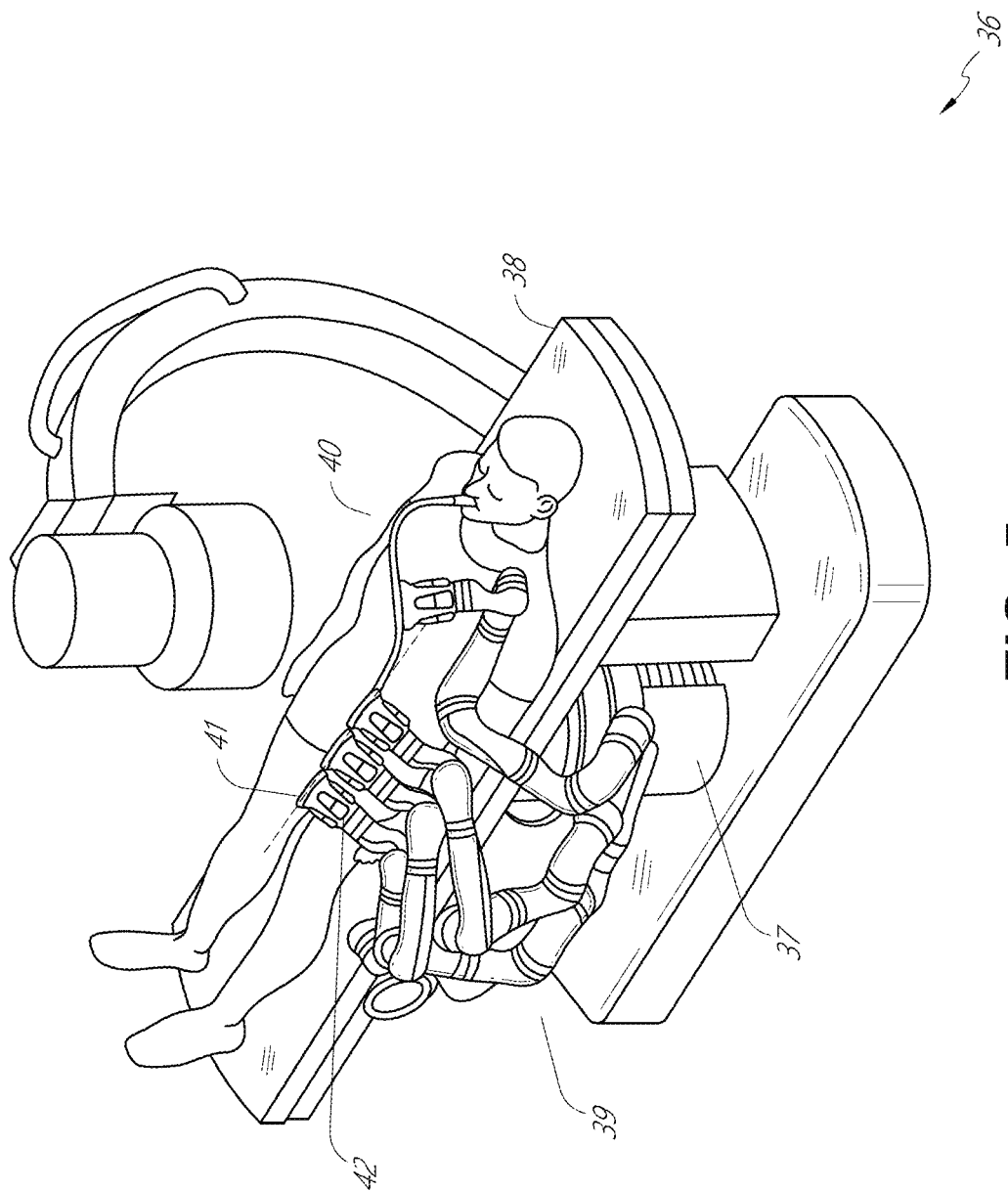
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
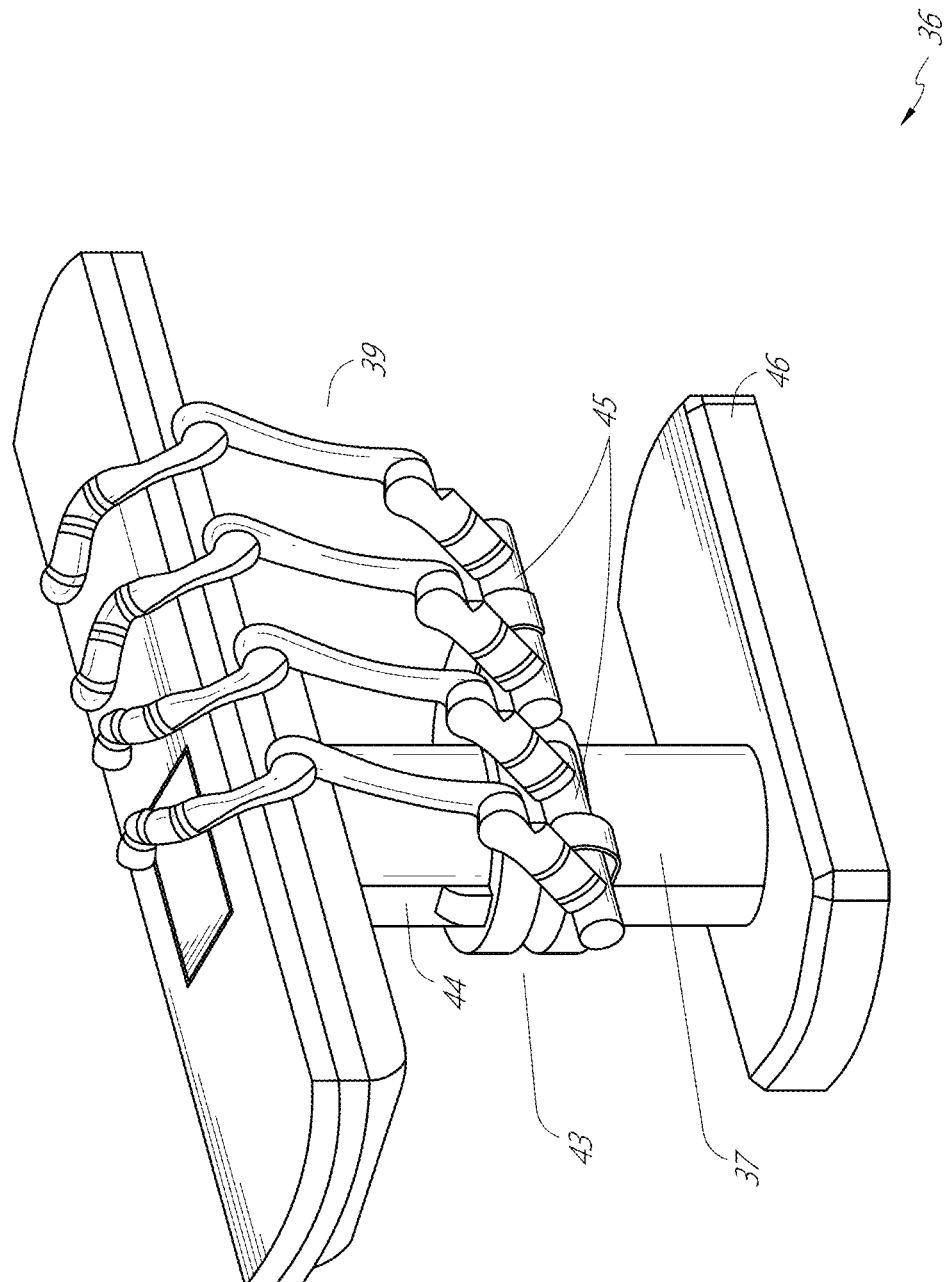
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
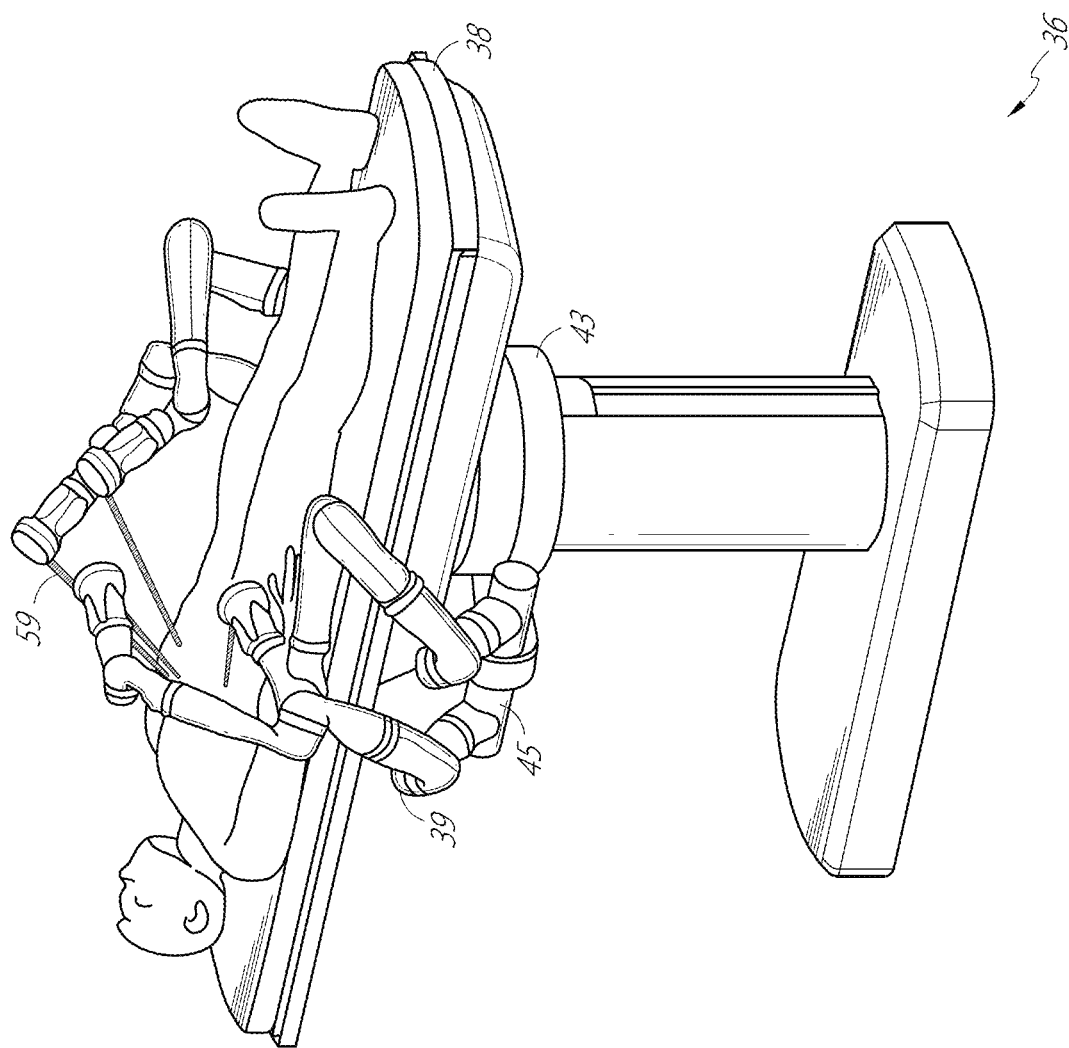
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intra-operative information, such as real-time imaging, navigation, and tracking information. In some embodiments, the tower may also contain holders for gas tanks to be used for insufflation.

Figure 7:
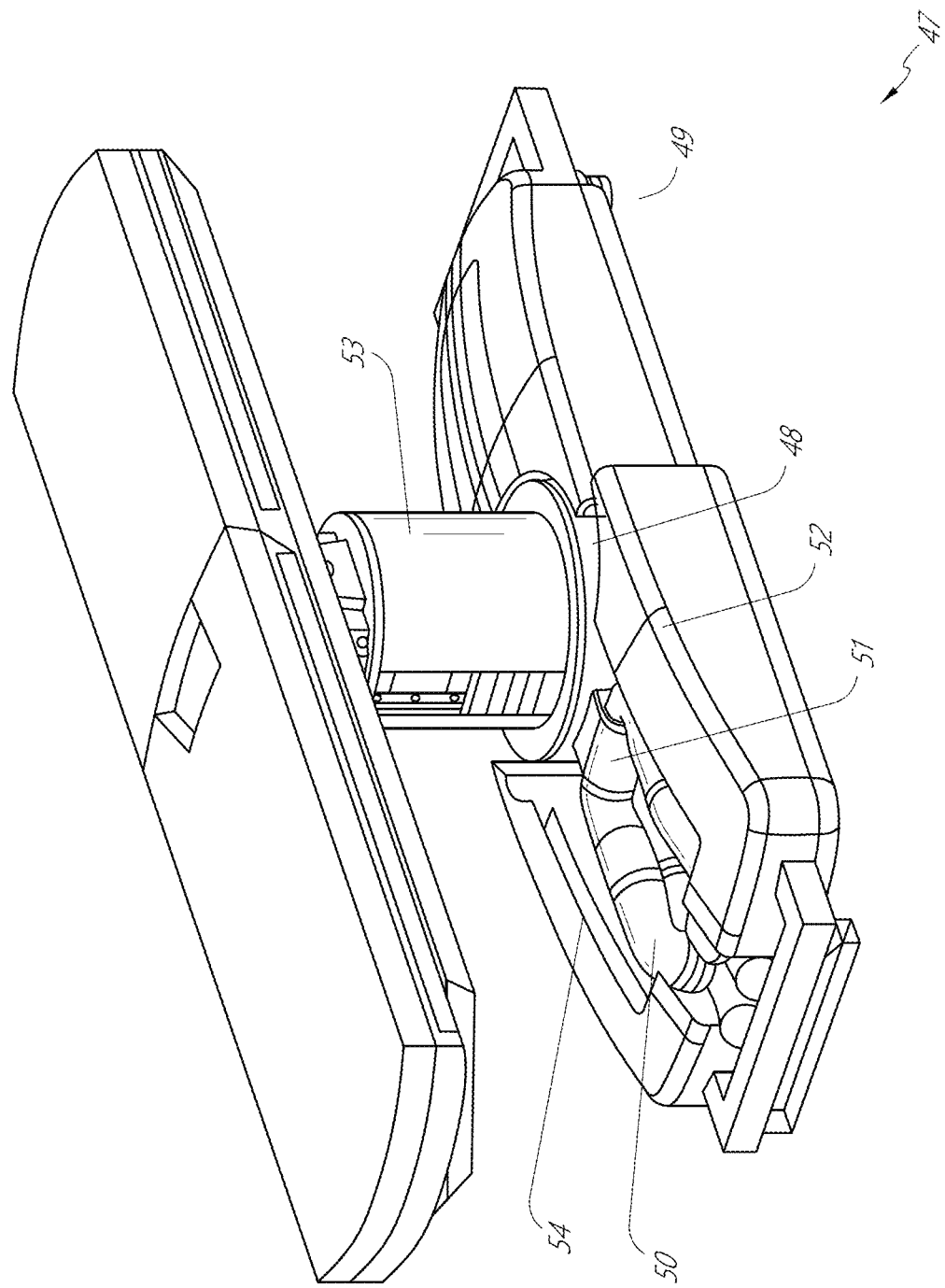
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
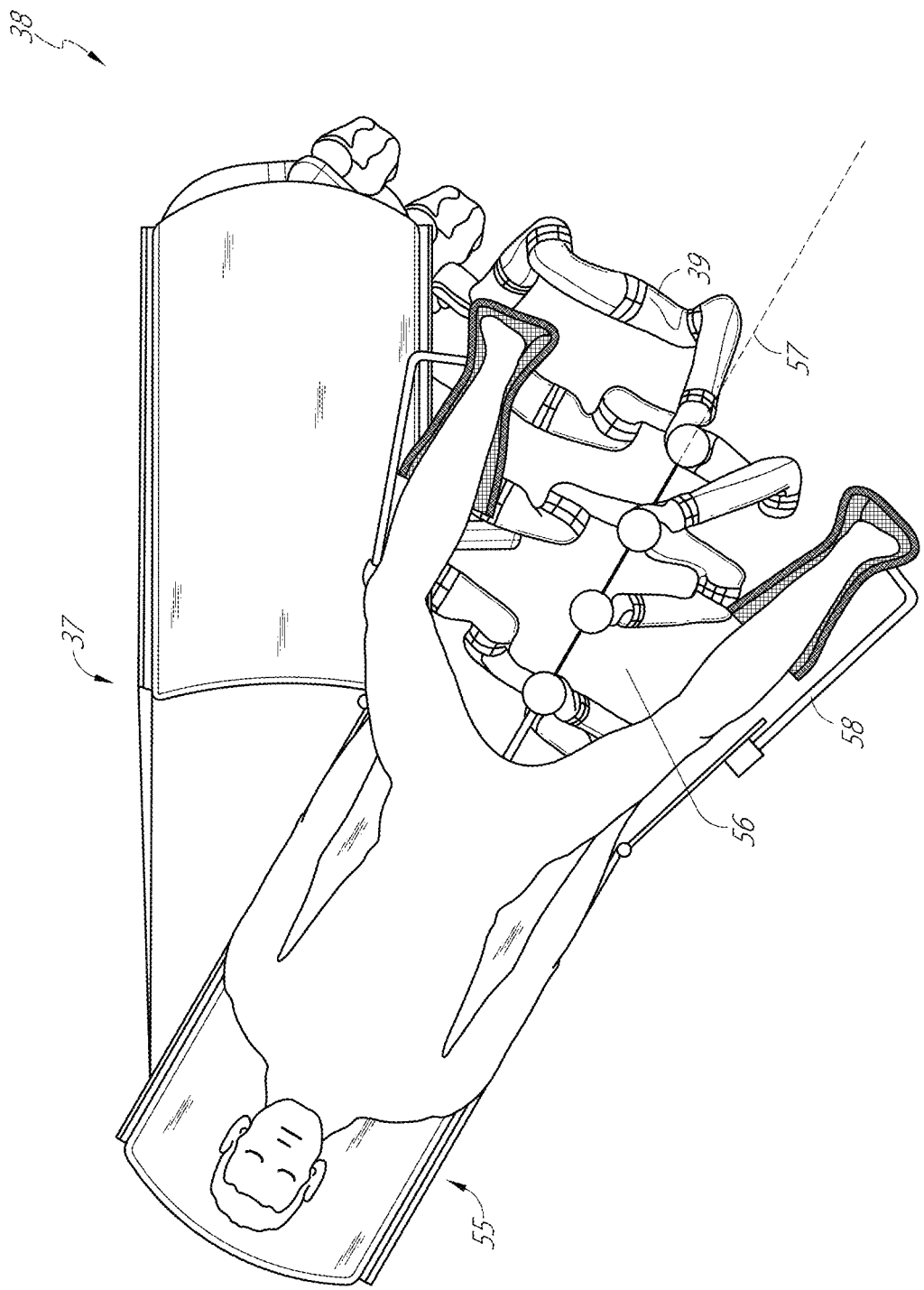
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
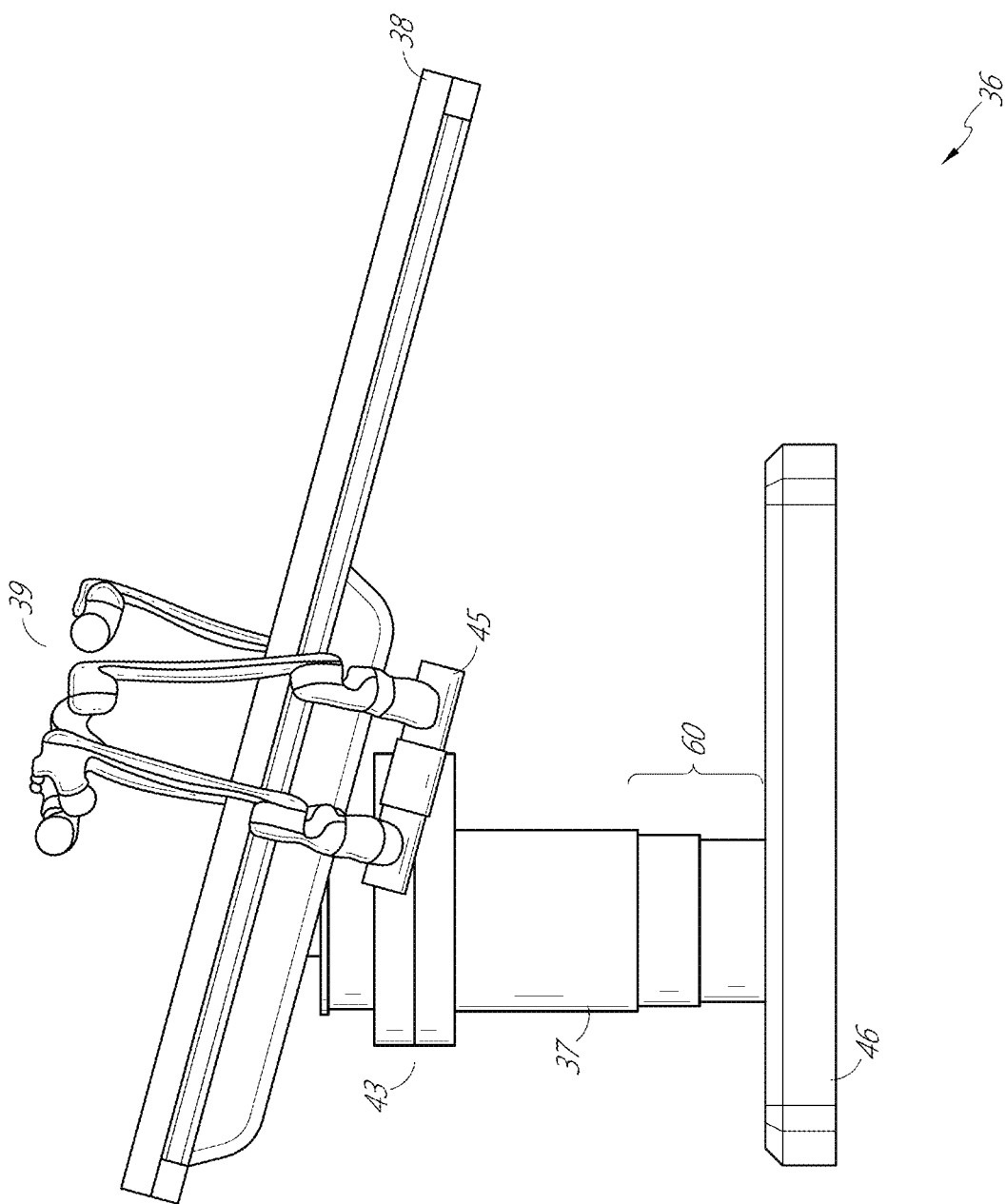
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
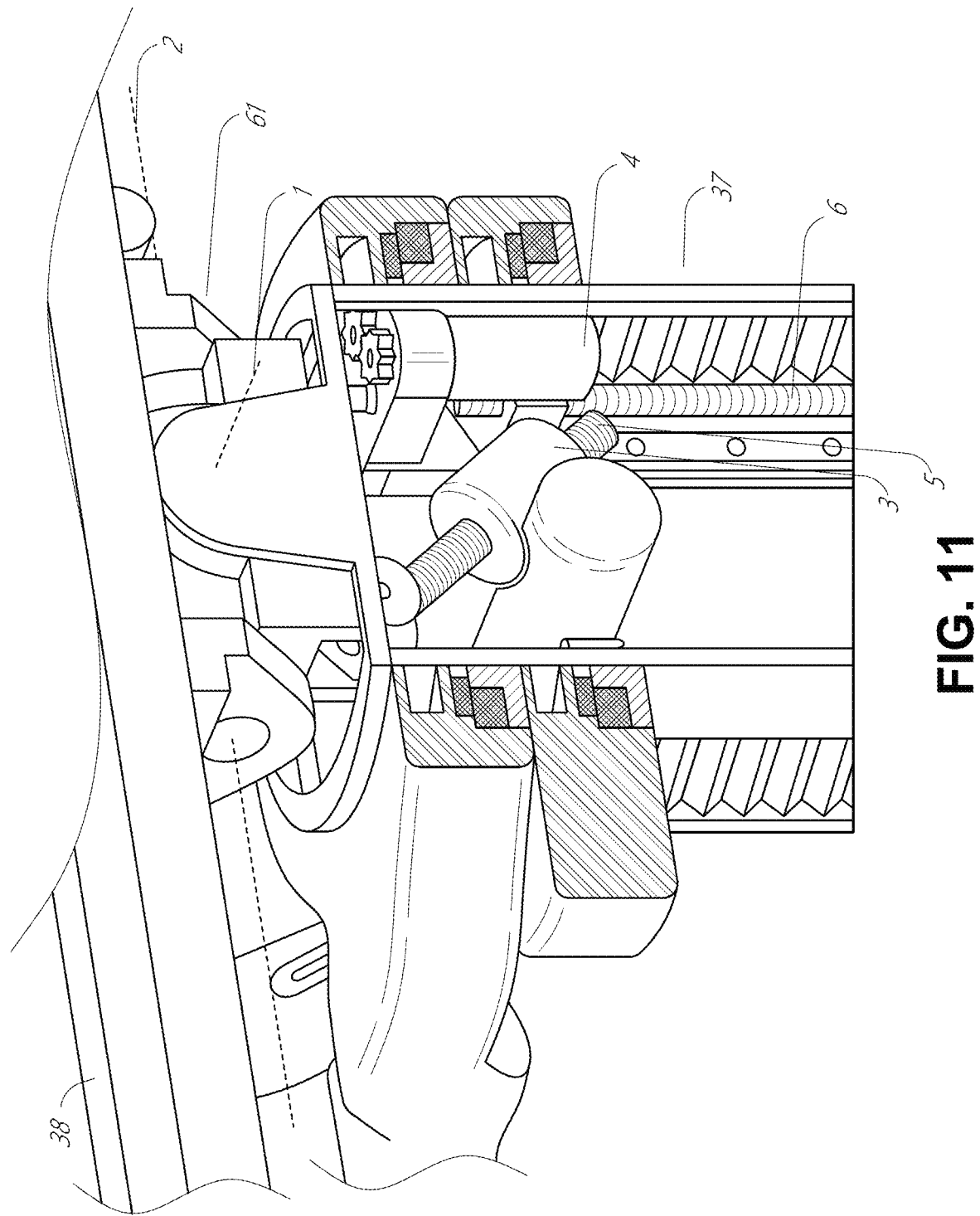
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
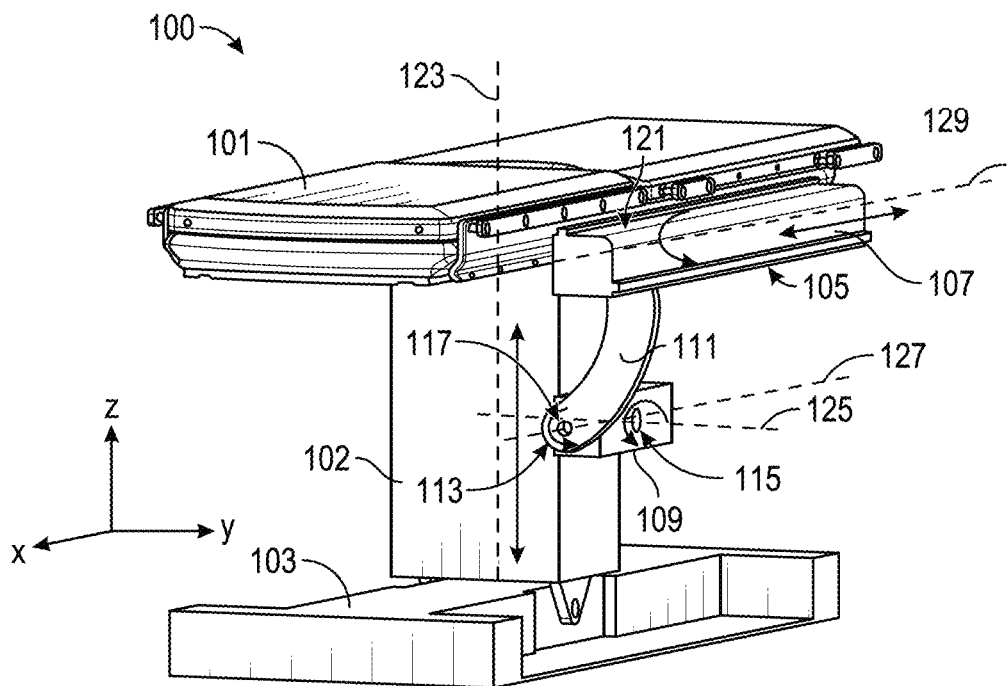
FIG. 12 illustrates an alternative embodiment of a table-based robotic system.
Figure 13:
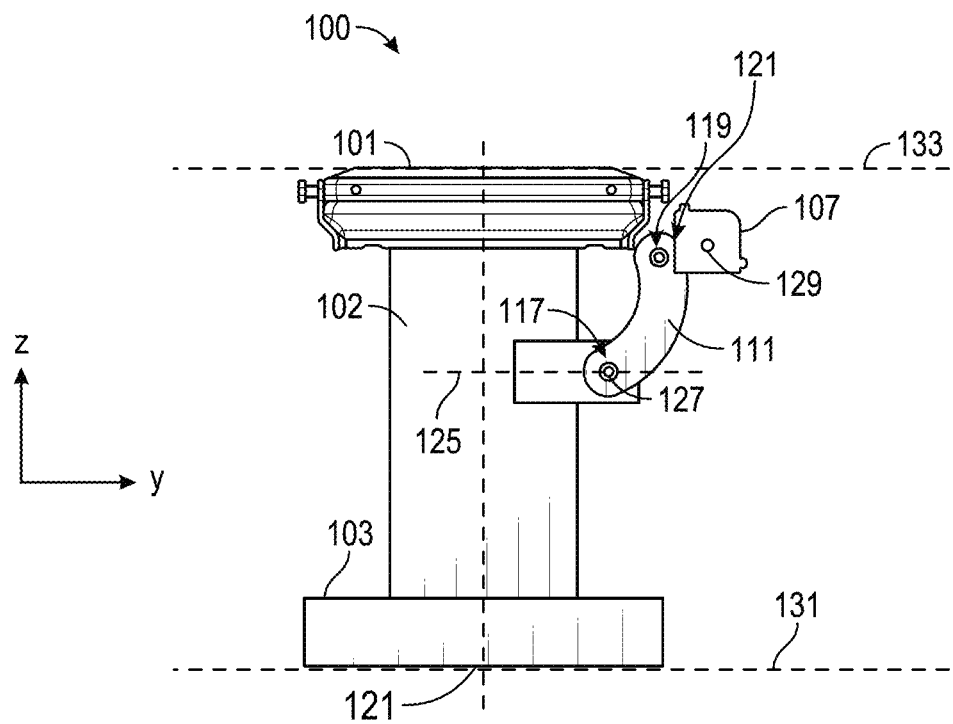
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105.

A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
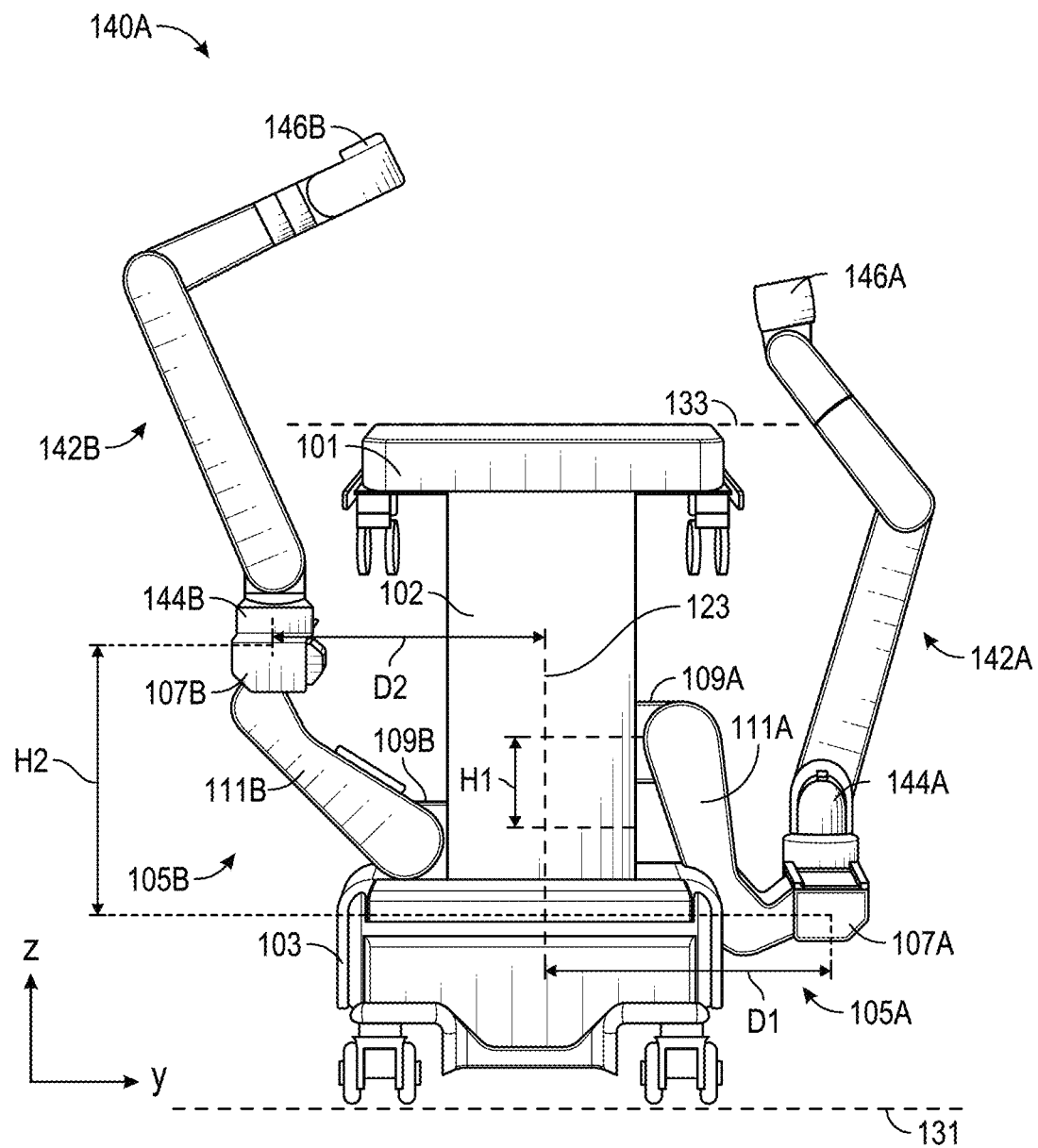
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
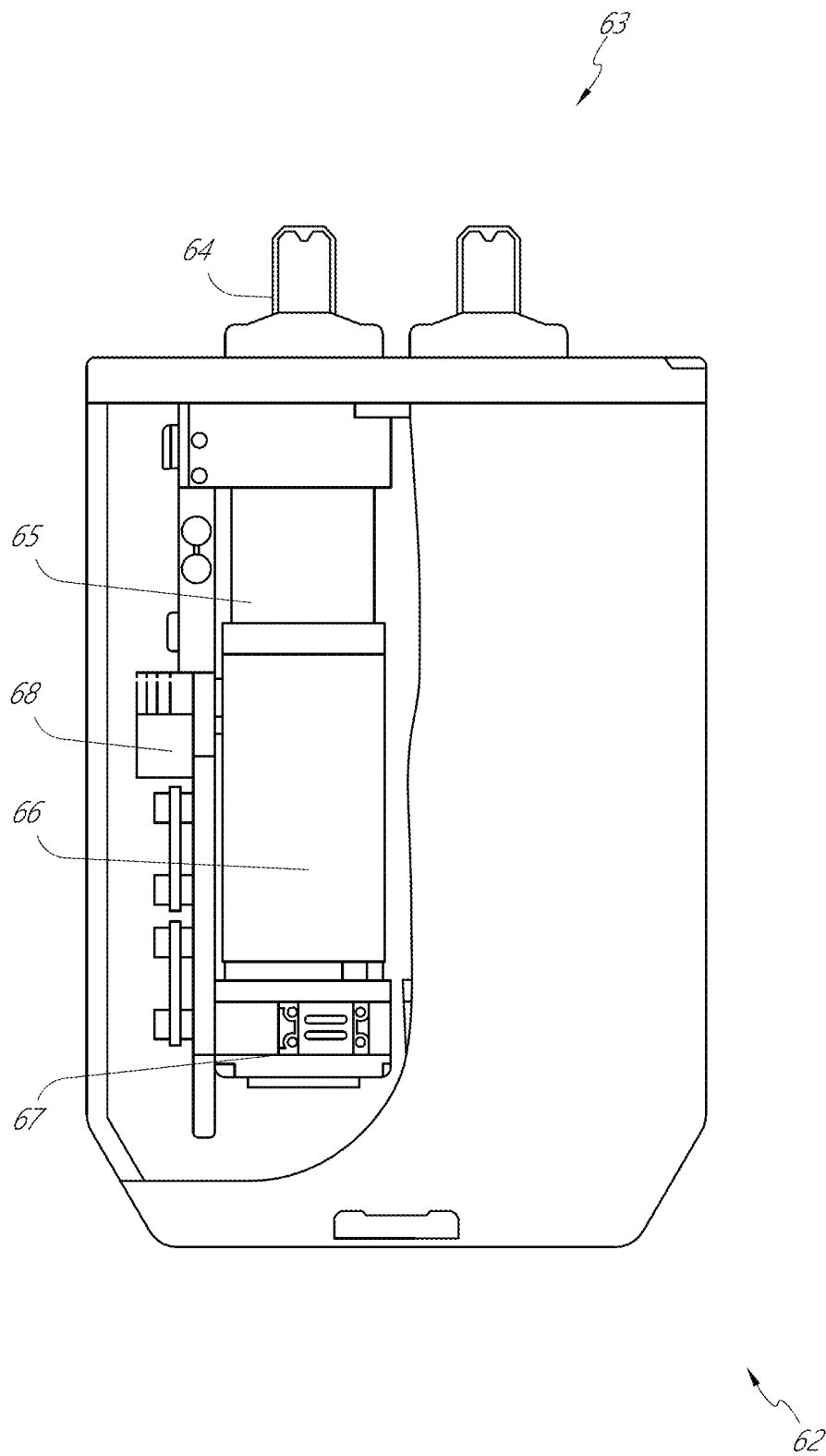
FIG. 15 illustrates an exemplary instrument driver.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuity 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument

Figure 16:
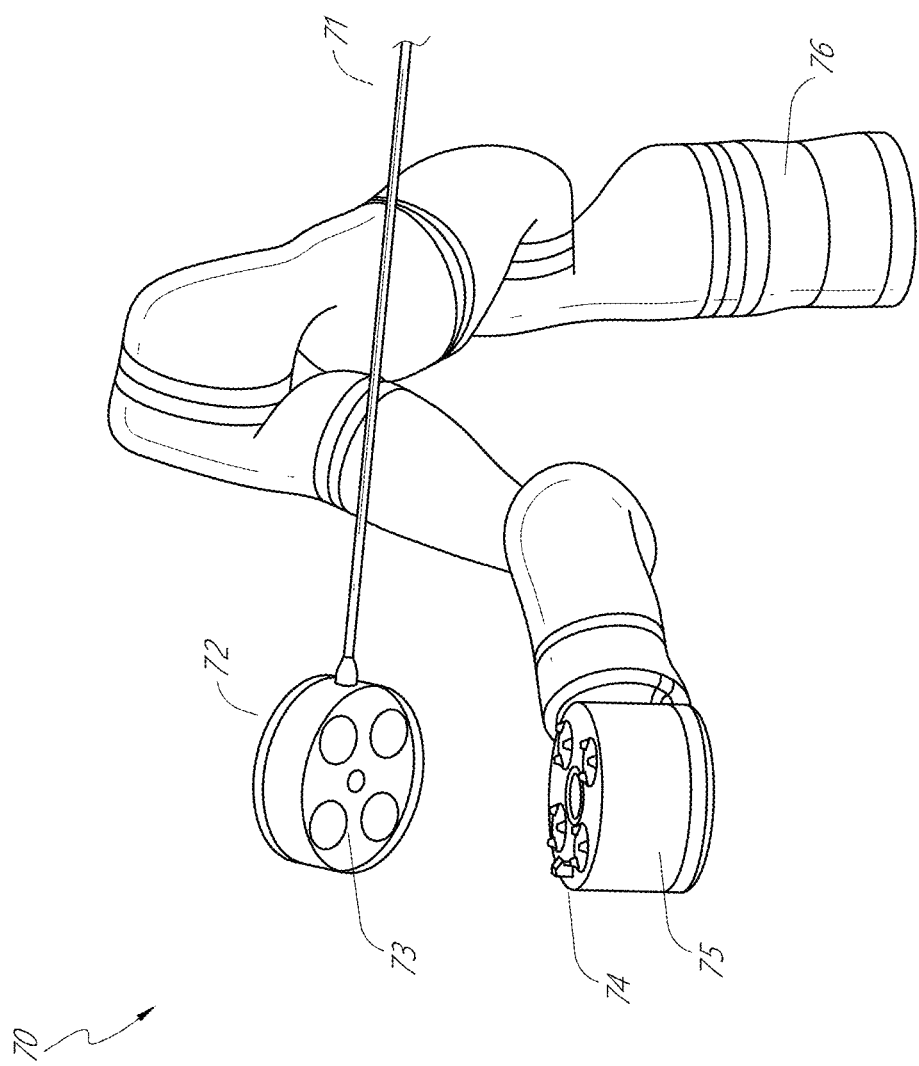
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
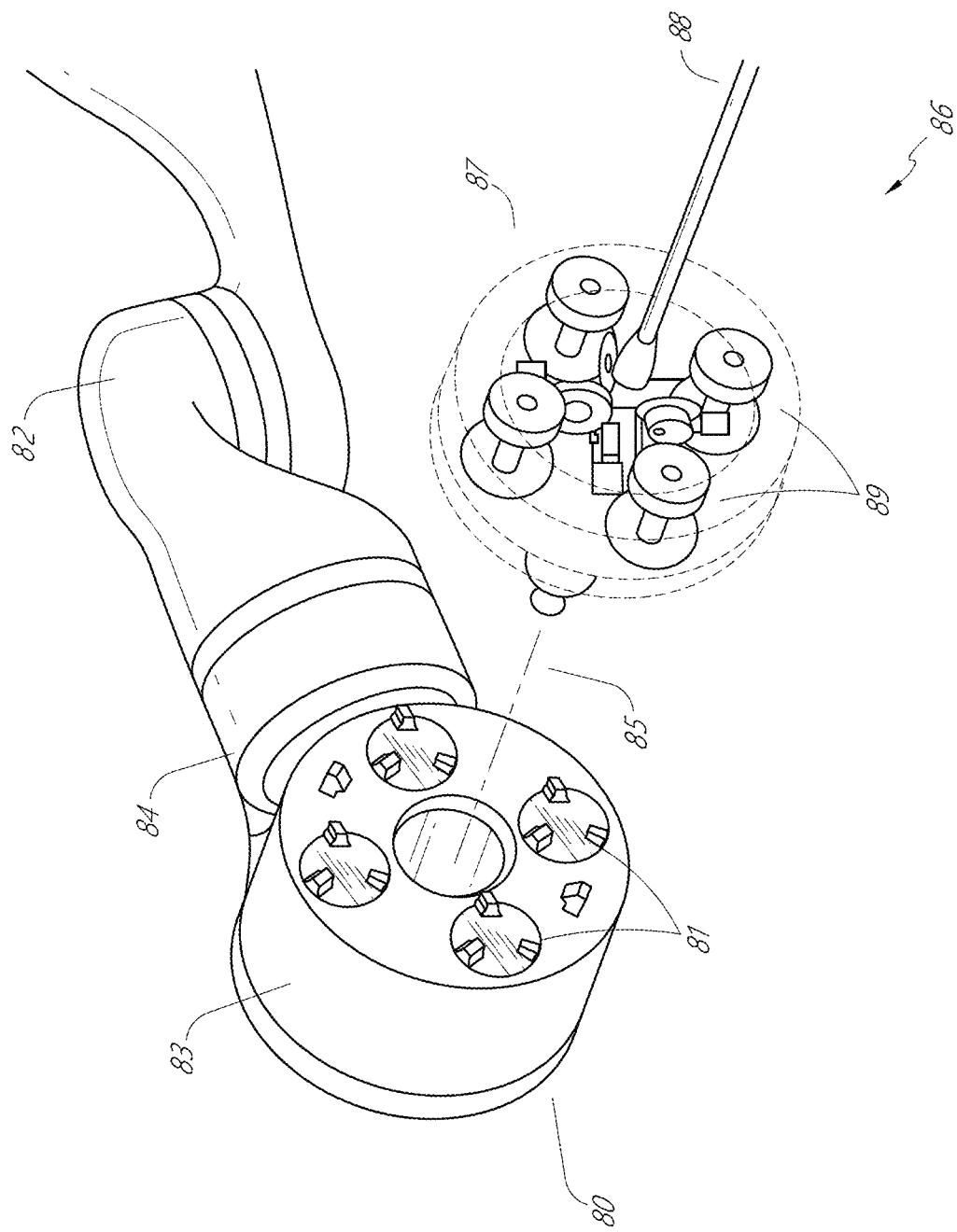
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
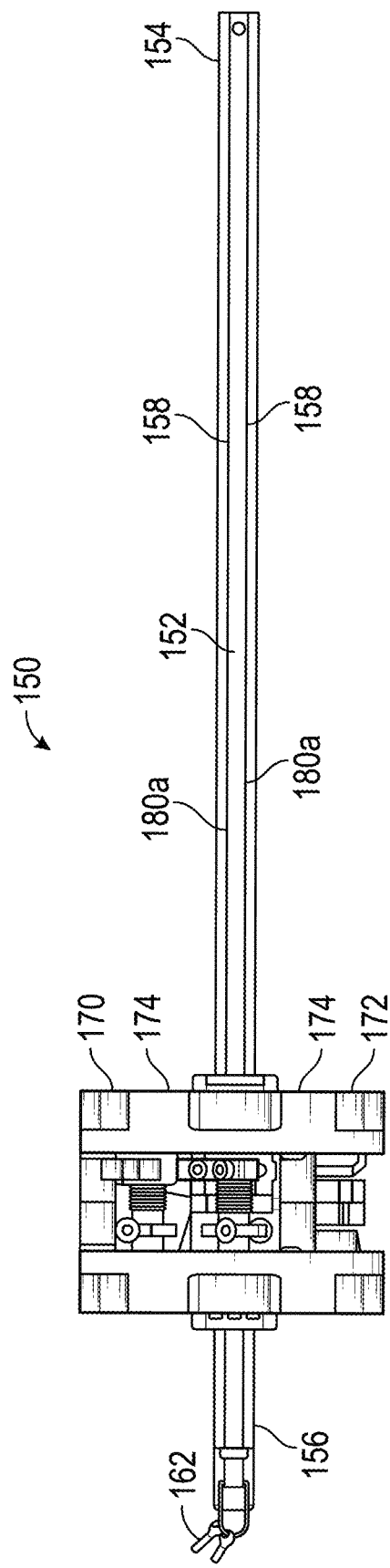
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
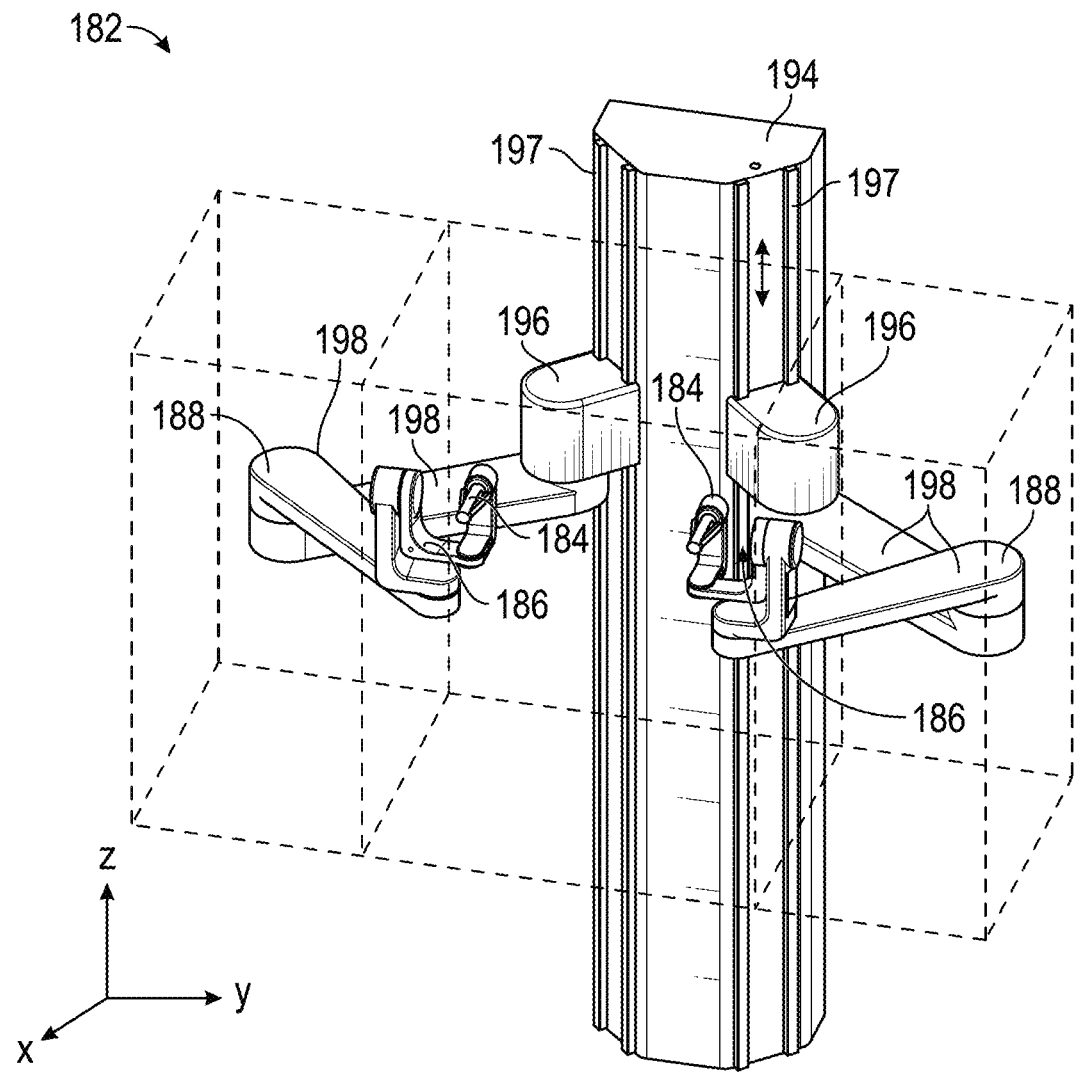
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
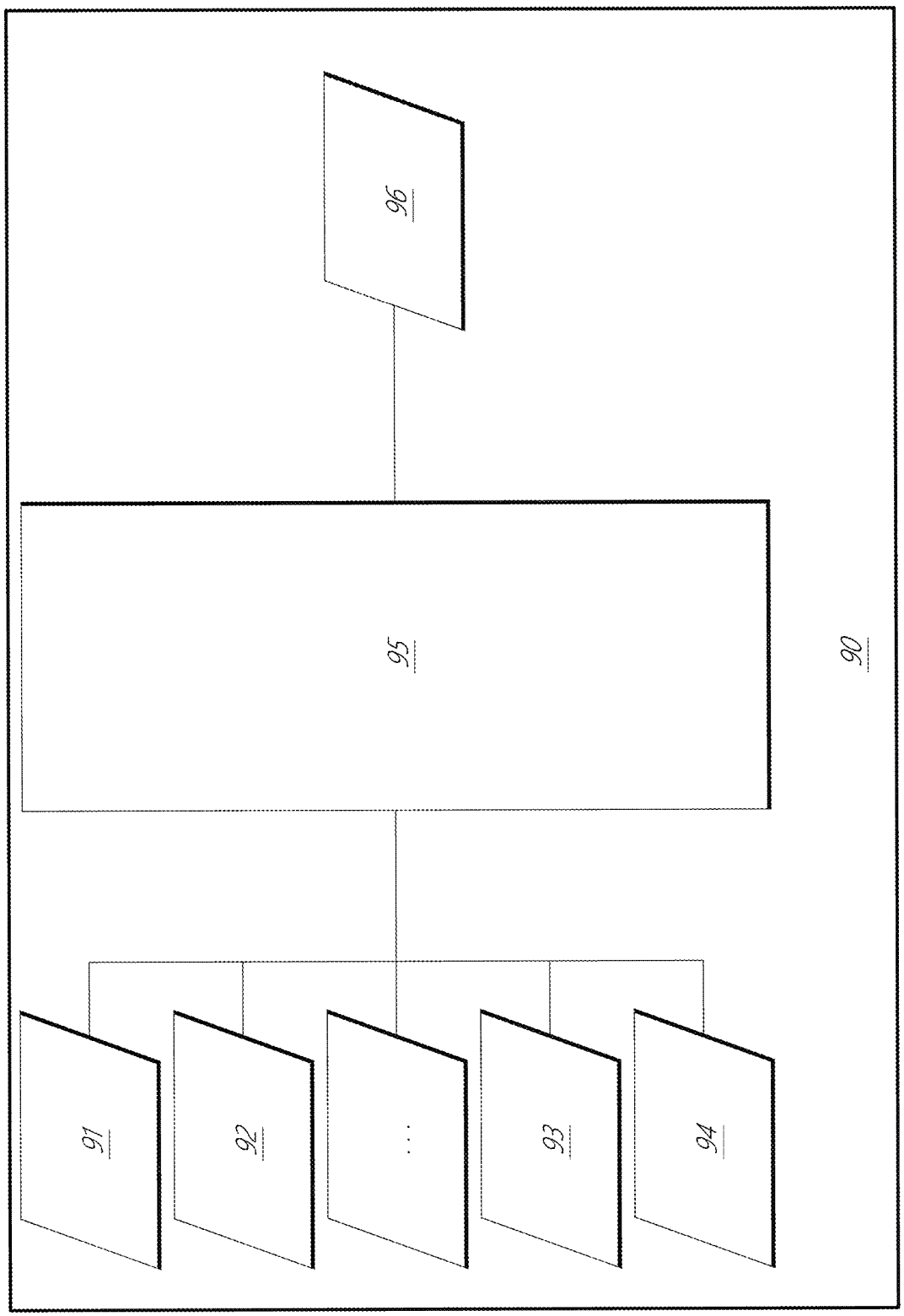
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Dynamic Tensioning of a Multi-Wire Input

Examples of the disclosure relate to systems and techniques for robotic medical instruments. The robotic medical instruments can be used, in some aspects, with robotically-enabled medical systems, such as those described above with reference to FIGS. 1-20. Examples of medical instruments can include an instrument configured to be controlled by a robotic arm, such as a flexible endoscope or catheter. In some aspects, the medical instrument can include a medical tool actuated with a wrist, a camera (e.g., with an optical fiber), a gripper tool, a basketing tool, a blade tool, a laser tool (e.g., with an optical fiber), and/or other instruments described herein. In some aspects, the medical instruments can be configured for endoscopic procedures. For example, the medical instruments can be configured for ureteroscopy, gastroscopy, bronchoscopy, or other endoscopic procedures. In some examples, the medical instruments can be configured for laparoscopic procedures or other types of medical procedures (e.g., open procedures).

The medical instrument may be articulated to navigate through the patient's anatomy to access, visualize, and diagnose and/or treat pathologies in various organs via orifices and lumens of various organs, such as a kidney for ureteroscopy. To navigate through the orifices and lumens of various organs, such as a kidney, the medical instrument should be flexible and deflectable in one or more directions. The medical instrument can also be elongate such that it can reach the desired target area in the patient's anatomy.

The medical instrument can be attached to an instrument drive mechanism that is positioned on the end of a robotic arm or other instrument positioning device. The instrument drive mechanism can include one or more robotic drive outputs that engage one or more robotic drive inputs or drive shafts to robotically control the medical instrument. The physician may use a controller (for example, as shown in FIG. 19) to control the robotically-enabled system.

In some aspects, the medical instrument can include a tool with a wrist and the wrist can be actuated to control and manipulate the tool. In some aspects, the medical instrument can include an instrument handle, which can include one or more rotational drive inputs or drive shafts. The drive shafts may actuate one or more pullwires with one or more expanding pulleys. The one or more pullwires may be actuated to articulate an elongated shaft or the wrist of the tool.

The medical instruments can include an elongated shaft and an instrument handle (or instrument base). The elongated shaft can be configured for insertion into a patient's anatomy during a medical procedure. In some aspects, the elongated shaft is inserted into the patient's anatomy through a natural orifice. In some aspects, the elongated shaft is inserted into the patient's anatomy through an incision or other surgical opening. The elongated shaft can be flexible. The elongated shaft can be articulable and controllable. This can allow an operator, such as a physician, to control the articulation of the elongated shaft so as to navigate and steer the medical instrument through the patient's anatomy. Controlling the articulation of the elongated shaft can include deflecting or bending an articulable portion of the elongated shaft and in certain embodiments the roll or rotation of the elongated shaft about a longitudinal axis of the shaft.

In some aspects, the articulable portion can be a distal portion of the elongated shaft. The articulable portion may be articulable in one or more degrees of freedom. Degrees of freedom may be linear or rotational. For example, a first degree of freedom may be translation along a first axis, a second degree of freedom may be translation along a second axis perpendicular to the first axis, and a third degree of freedom may be along a third axis perpendicular to both the first and second axes. Additional or alternative degrees of freedom may exist, such as rotation about one or more of the first, second, and/or third axes, and/or swiveling within first, second, and/or third planes. Actuation of the elongated shaft may be controlled at the instrument base.

An instrument base or handle can be connected to the elongate shaft, such as at the proximal portion or distal portion of the shaft. The instrument base can include one or more rotational drive inputs or drive shafts. The elongate shaft can be coupled to the drive input to control articulation of one or more portions of the elongate shaft. The elongated shaft can include one or more pull wires which extend along the length of the elongate shaft. The one or more pull wires can be actuatable to articulate the elongated shaft. The one or more drive inputs, coupled to one or more pull wires with one or more expandable pulleys, can be configured to bend the shaft, such as at the distal end, in various directions. The medical instrument can include drive inputs, which may also be called rotational drive inputs, inputs, drive shafts, rotational drive shafts, or shafts. The drive inputs may be located in a handle of the medical instrument.

In some aspects, one of the drive inputs is configured to provide two-way deflection control for the elongated shaft of the medical instrument. Two-way deflection control can allow deflection of the elongated shaft in two directions. In some embodiments, the two directions can be opposite directions, such as up and down or left and right. This can also referred to as two-way deflection control in a single plane, such as an up-down plane or a left-right plane. Directional terms (e.g., up, down, left, right, etc.) are used broadly to indicate different directions relative to an orientation of the medical instrument. Because the medical instrument can be constantly repositioned in a wide variety of orientations, the directional terms should not be interpreted as limiting. For example, the directions referred to as up, down, left, and right can change depending on the orientation of the instrument. In some aspects, controlling or operating the manual or robotic drive input in a first direction causes deflection of the elongated shaft in a first direction (e.g., up) and manipulating the manual or robotic drive input in a second direction causes deflection of the elongated shaft in a second direction (e.g., down). In some aspects, the medical instrument may include an additional drive input configured to allow an additional two-way deflection control. For example, the first drive input can allow two-way deflection control in opposing directions such as up and down directions, and the second drive input can allow two-way deflection control in left and right directions. In another example, the first drive input can allow two-way deflection in any two directions, such as up and left, and the second drive input can allow two-way deflection in the other two directions, such as down and right. This would permit four-way deflection control for the elongated shaft using two drive inputs.

In some aspects, the drive inputs are configured to allow four-way deflection control. In some aspects, four-way deflection control allows articulation of the elongated shaft in four different directions. In some aspects, the directions can be four orthogonal directions, such as up, down, left, and right. In some aspects, the drive inputs configured for four-way deflection control can include two robotic drive inputs. The two drive inputs can be configured to engage to with two corresponding drive outputs on the instrument drive mechanism. Each drive input can be rotatable in two opposite directions, for example, clockwise and counter-clockwise. Rotation of a first of the two drive inputs in one direction (e.g., the clockwise direction) can allow articulation in one of the four direction (e.g., up). Rotation of the first of the two drive inputs in the opposite direction (e.g., the counterclockwise direction) can allow articulation in another of the four directions (e.g., down). Rotation of a second of the two drive inputs in one direction (e.g., the clockwise direction) can allow articulation in another of the four directions (e.g., right). And rotation of the second of the two drive inputs in the opposite direction (e.g., the counterclockwise direction) can allow articulation in another of the four direction (e.g., down). Thus, four-way deflection control can be achieved using two drive inputs. In some aspects, the drive inputs are configured to provide other numbers of directional deflection control, such as two-way deflection control, three-way deflection control, etc.

As described above (for example, with reference to FIGS. 15-18), in some aspects, the medical instrument can include one or more pull wires extending along the elongated shaft (e.g., extending on or through at least a portion of the elongated shaft). The pull wires can be attached to actuation mechanisms, such as one or more expandable pulleys, within the instrument handle. The actuation mechanism can, in turn, be connected to the drive inputs such that actuation of the drive inputs operates the actuation mechanisms to pull on the pull wires to cause articulation of the elongated shaft. In some aspects, one or more of the drive inputs are each connected to the same actuation mechanism (e.g., pulley, capstan, and/or pulley assembly) within the instrument handle such that the drive input can be used to actuate the same actuation mechanism.

The physician may control the medical instrument by controlling or operating drive inputs or drive shafts of the medical device. It can be advantageous to route and control two wires or cables on a single drive shaft, which can then drive bi-directional control. This can be advantageous as it is more efficient and frees up other drive shafts for other purposes (e.g., to control other types of articulation or functions). One of the challenges with articulating a medical instrument is the management of slack in the pull wires or control wires about the pulley or capstan. Each of the two pull wires can each be attached to a pulley. The two pulleys can each couple to the same single drive shaft. The two pulleys can be driven by the single drive shaft, allowing the single drive shaft to control two directions of articulation or deflection. However, the challenge with two wires routed on a single drive shaft (via two pulleys) can lead to excessive slack which can lead to excessive articulation response lag that creates a subpar robotic driving experience as a user attempts to navigate internal anatomical structures. For example, as a pulley is rotated one of the wires is placed in tension while the other un-tensioned wire becomes slack. When rotation of the pulley is reversed, the slack in the un-tensioned wire can create the undesirable lag described above.

The control wires can be used for instruments or for articulating an elongate shaft (such as a catheter). In either of these uses, it is desirable to use a single pulley to control two control wires on a single drive shaft, but this can lead to undesirable lag. Therefore, it is even more desirable to drive two pulleys on a single drive shaft, each pulley coupled to one of two control wires, that can reduce slack and minimize response lag.

FIGS. 21A-21B and 22A-22B illustrate an example embodiment of a dynamic pulley system 200 with two expandable pulleys 210, 220. FIG. 21A illustrates the dynamic pulley system 200 with two expandable pulleys 210, 220 coupled together in a first configuration. FIG. 21B illustrates the two expandable pulleys 210, 220 of the dynamic pulley system 200 separated and positioned side by side in the first configuration. FIG. 22A illustrates two expandable pulleys 210, 220 of the dynamic pulley system 200 of FIGS. 22A-22B coupled together in a second configuration. FIG. 22B illustrates the two expandable pulleys 210, 220 of the dynamic pulley system 200 of FIG. 22A positioned side by side in the second configuration. The dynamic pulley system 200 can also be considered a single pulley with two sides 210, 220 with each side of the pulley engaging a separate pull wire 212, 222, respectively. The dynamic pulley system 200 of FIGS. 21A-22B can be used to control the pull wires 212, 222 which can be connected to and actuate a catheter or tool, as described above. The two expandable pulleys 210, 220 of the dynamic pulley system 200 of FIGS. 21A-22B can actuate pull wires 212, 222 connected to a catheter or tool.

During bi-directional driving actuated by a drive shaft, each attached pulley 210, 220 can expand and contract to maintain a minimum tension on each of the pullwires 212, 222, thereby managing and preventing any excessive slack along the path along each pulley 210, 220. The first and second pulleys 210, 220 are configured to expand or collapse to address the issue of response lag which can occur with multiple wires driven by a single drive shaft. The first and second pulleys 210, 220 can expand to dynamically tension and maintain minimum tension on each respective pull wire 212, 222 and take up any slack, such as when the drive shaft changes directions.

The first expanding pulley 210 may include a first pull wire 212 wrapped around the first expanding pulley 210 in one direction, such as the counterclockwise direction 240. The second expanding pulley 220 may include a second pull wire 222 wrapped around the second expanding pulley 220 in another direction, such as the clockwise direction 230.

The first expanding pulley 210 is configured to expand when the first expanding pulley 210 is rotated in the first direction (e.g. counterclockwise 240) and to collapse when the first expanding pulley 210 is rotated in the second direction (e.g. clockwise 230). The second expanding pulley 220 is configured to collapse when the second expanding pulley 220 is rotated in the first direction (e.g. counterclockwise 240) and to expand when the second expanding pulley 220 is rotated in the second direction (e.g. clockwise 230). The first direction corresponds to a direction at which the first expanding pulley 210 pushes on or releases tension on the first pull wire 212, and the second direction corresponds to a direction at which the first expanding pulley 210 pulls on or increases tension on the first pull wire 212. With respect to the second expanding pulley 220, the first direction corresponds to a direction at which the second expanding pulley 220 pulls on or increases tension on the second pull wire 222, and the second direction corresponds to a direction at which the second expanding pulley 220 pushes on or releases tension on the second pull wire 222. The first expanding pulley 210 can, from the expanded configuration, rotate in the second direction (e.g., clockwise 230) to increase tension in the first pull wire 212. As the first expanding pulley 210 is rotated and tension on the first pull wire 212 is applied, the first expanding pulley 210 collapses. In parallel, the second expanding pulley 220 can, from the collapsed configuration, decrease tension in the second pull wire 222. As the second expanding pulley 220 is rotated and tension on the second pull wire 222 is released, the second expanding pulley 220 can expand to take up slack in the second pull wire 222.

FIG. 21A-21B illustrate the dynamic pulley system 200 rotated in the first direction, such as the counterclockwise direction 240. FIG. 22A-22B illustrate the dynamic pulley system 200 rotated in the second direction, such as the clockwise direction 230. The second direction (e.g. clockwise 230) can be opposite of the first direction (e.g. counterclockwise 240).

As shown in FIGS. 21A and 22A, the first and second pulleys 210, 220 can be positioned with the center of the pulleys aligned, through the center of the pulleys. A drive shaft 260 (as shown in FIGS. 21A and 22A) may be coupled to the first and second pulleys 210, 220. The drive shaft 260 can be similar to the one or more drive shafts 64 as shown in FIG. 15. As shown in FIG. 15, the drive unit 63 can include one or more drive shafts 64, which can be arranged with parallel axes. The one or more drive shafts 64 can be connected to the one or more pulleys to provide controlled torque to a medical instrument via the drive shafts 64. The drive shaft 64 can then simultaneously rotate the first and second pulley 210, 220. As shown in FIG. 21A-21B, as the drive shaft 260 rotates in the first direction 240, the first pulley 210 expands and the second pulley 220 collapses. As shown in FIG. 22A-22B, as the drive shaft 260 rotates in the second direction 230, the first pulley 210 collapses and the second pulley 220 expands.

FIG. 21A-21B illustrate the pulley system 200 in a first configuration, with the first pulley 210 in an expanded configuration 210A, where the diameter of the expanded first pulley ("D1") is expanded or extended. The first pulley 210 is configured to expand when the first pulley 210 is rotated in the first direction, such as counterclockwise 240. FIG. 21A-21B illustrate the pulley system 200 in the first configuration, with the second pulley 220 in a collapsed configuration 220A, where the diameter of the collapsed second pulley ("D2") is contracted or collapsed. The second pulley 220 is configured to contract when the second pulley 220 is rotated in the first direction, such as counterclockwise 240. The first expanding pulley 210 can, from the expanded configuration 210A as shown in FIG. 21A, increase or apply tension in the first pull wire 212 by rotating in the second direction 230. As the first expanding pulley 210 is rotated and tension on the first pull wire 212 is applied, the first expanding pulley 210 collapses as shown in FIG. 22A-22B. The second expanding pulley 220 can, from the collapsed configuration 220A as shown in FIG. 21A, decrease or release tension in the second pull wire 222 by rotating in the second direction 230. As the second expanding pulley 220 is rotated and tension on the second pull wire 222 is released, the second expanding pulley 220 can expand as shown in FIG. 22A-22B to take up slack in the second pull wire 222.

FIG. 22A-22B illustrate the pulley system 200 in a second configuration, with the first pulley 210 in the collapsed configuration 210B, where the diameter of the collapsed first pulley ("D1") is collapsed or contracted. The first pulley 210 is configured to collapse when the first pulley 210 is rotated in the second direction, such as clockwise 230. FIG. 22A-22B illustrate the pulley system 200 in the second configuration, with the second pulley 220 in an expanded configuration 220B, where the diameter of the expanded second pulley 220B ("D2") is expanded. The second pulley 220 is configured to expand when the second pulley 220 is rotated in the second direction, such as clockwise 230. The first expanding pulley 210, from the collapsed configuration 210B as shown in FIG. 22A-22B, can decrease or release tension in the first pull wire 212 by rotating in the first direction 240. The second expanding pulley 220, from the expanded configuration 220B as shown in 22A-22B, can increase or apply tension in the second pull wire 222 by rotating in the first direction 240.

In some aspects, the first pull wire 212 and second pull wire 222 can extend along the elongate shaft (not shown), such as from a distal end to a proximal end of the elongate shaft. The first and second pull wires 212, 222 can be configured to bend the shaft in two opposing directions. The two opposing directions can be left and right or anterior and posterior. The two opposing directions can also be up and down or inferior and superior. In some aspects, the first and second pull wires 212, 222 can bend the shaft in any two directions, such as up and right or down and left. The one or more drive inputs can also be configured to rotate the elongate shaft about its longitudinal axis or linearly translate. The instrument base can include two drive inputs. Each drive input can receive a dynamic tension pulley system including two expanding pulleys. Each dynamic pulley can be coupled to a pull wire. Each of the drive inputs can control and articulate the elongate shaft in two directions. Therefore, two drive inputs can control four pull wires, thereby controlling four-way articulation of the elongate shaft. For example, a first and second pulley can be coupled to a first drive input, while a third and fourth pulley can be coupled to the second drive input. The first pull wire 212 and second pull wire 222 can also be actuated in other environments, such as tools coupled to a wrist (e.g. jaws, grippers, cutter, or any other tool).

Figure 23:
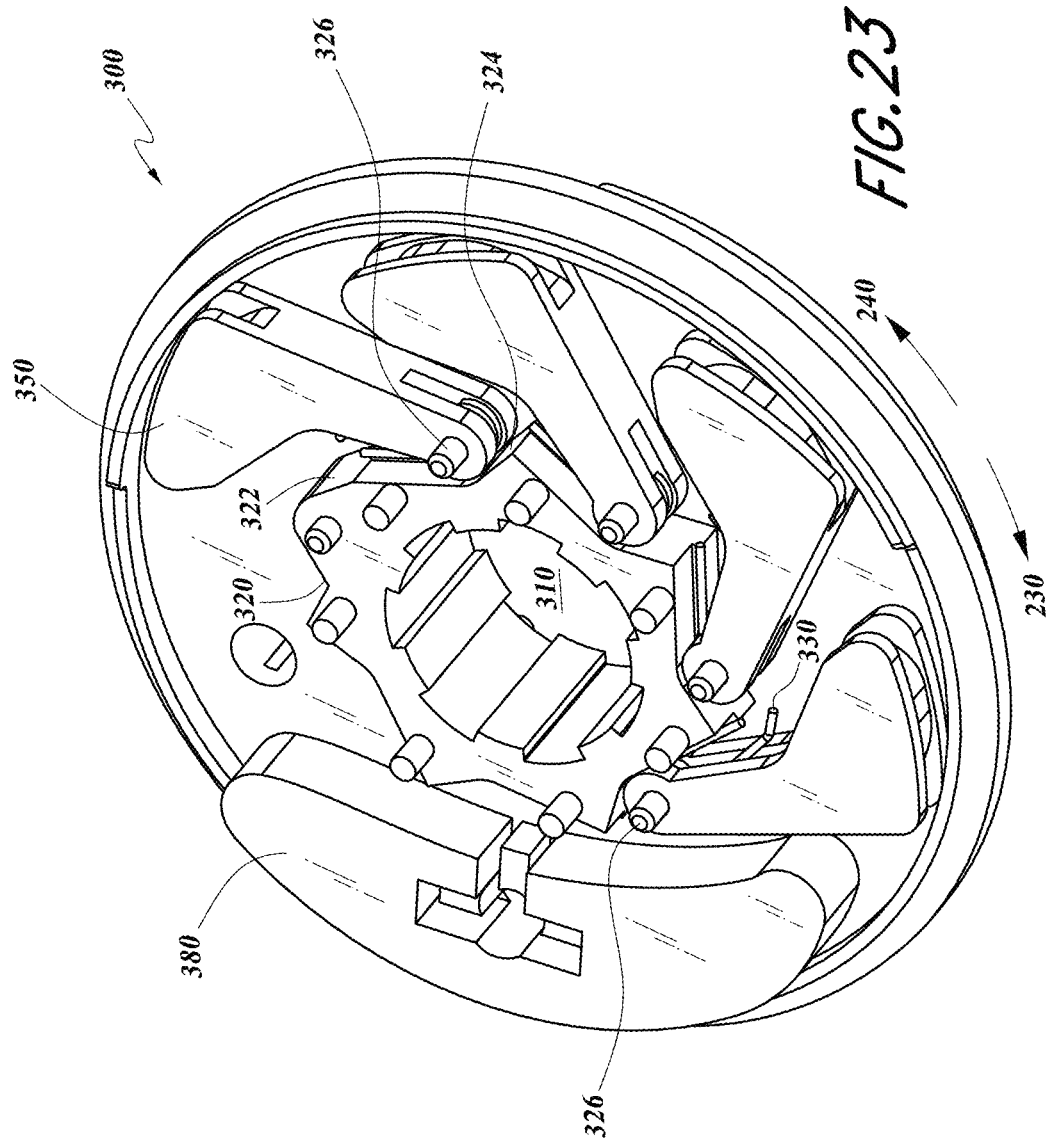
FIG. 23 illustrates a perspective front view of a dynamic pulley system.

As noted above, the dynamic pulley system can include one or more pulleys that are configured to expand or contract. Various mechanisms can be used to expand and contract the diameters of the pulleys. For example, in certain aspects, the one or more pulleys can be made of compressible or deformable material. In some examples, the outer surface of the pulley is supported by one or more springs. FIG. 23 illustrates an example of the dynamic pulley system that utilizes deformable leaves to change the diameter of at least a portion of the dynamic pulley system. As described, the dynamic pulley can dynamically tension one or more pull wires as the dynamic pulley is configured to collapse or expand against the pull wires. The dynamic tensioning of the expanding pulley can be created by deformable leaves, which may also be called wings or tabs, radially positioned about the expanding pulley.

Figure 25:
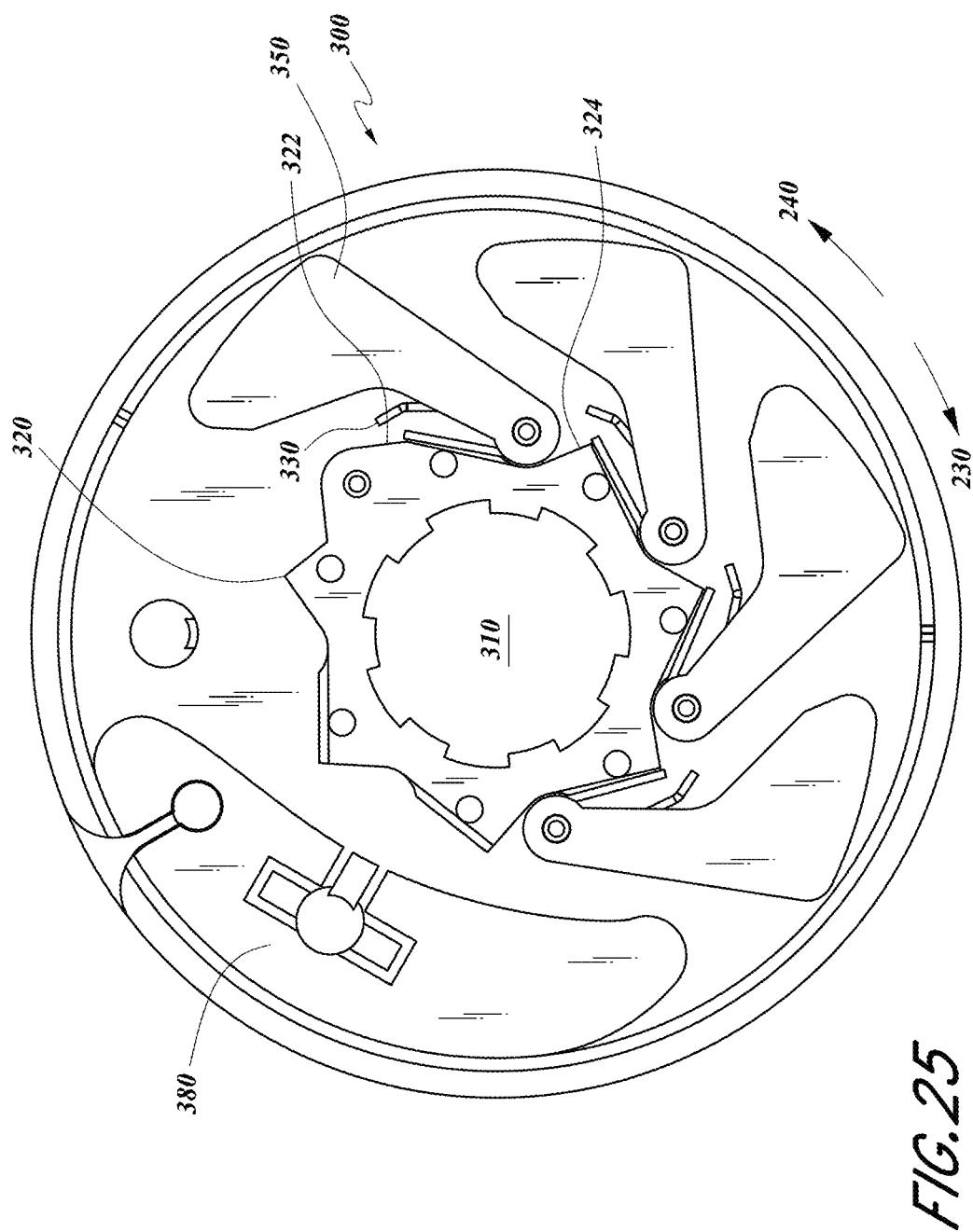
FIG. 25 illustrates a front view of the dynamic pulley system of FIGS. 23-24.

FIG. 23 illustrates a perspective front view of a dynamic pulley system. FIG. 25 illustrates a front view of the dynamic pulley system of FIG. 23. The front side of the dynamic pulley system may be considered a first pulley 300. In some aspects, the front side of the dynamic pulley system may be considered a first side 300 of a single pulley. The first pulley or first side 300 includes a central hub 320 with a central or center hole 310. The central hole 310 may be shaped and configured to receive the drive shaft (not shown). In some aspects, the central hole 310 may include a series of grooves or recesses that correspond to the shape of the drive shaft, such that the drive shaft can actuate rotation of the first pulley 300 when placed in the central hole 310.

The first pulley 300 includes a series of leaves 350, which may also be called tabs or wings. Each leaf 350 can extend outward from the hub 320. Although the first pulley 300 includes four leaves 350 as shown in FIGS. 23 and 25, the first pulley 300 includes any number of leaves 350, such as 1, 2, 3, 4, 5, 6, or more. Each of the series of leaves 350 can attach to various points of the hub 320 or to points immediately adjacent to the hub 320.

The hub 320 may include a series of projecting surfaces 322, 324 that act as a stop to limit the range of rotation for each tab 350. For example, the first projecting surface 322 acts to stop to limit rotation for the tab 350 in a first direction 240 and the second projecting surface 324 acts to stop limit rotation for the tab 350 in a second direction 230.

Although FIGS. 23 and 25 illustrate the series of leaves 350 positioned on one side of the first pulley 300, the leaves 350 may be positioned anywhere on the first pulley 300, such as on the opposite side of the first pulley 300 than shown or positioned all around the first pulley 300. The first pulley 300 can also include a fixed portion 380. The outer or distal surface of the fixed portion 380 may be curved to match the outer circumference of the first pulley 300 and to engage with a wire wrapped around the first pulley 300.

The attachment 326 where the leaf 350 attaches to or adjacent the hub 320 defines an axis of rotation or pivot point of the leaf 350. The leaf 350 may attach to the hub 320 or adjacent to the hub 320 a variety of ways, such as with a pin. The leaf 350 rotates about this axis of rotation or pivot point defined by the point of attachment 326. Each leaf 350 has a length from the point 326 where the leaf 350 attaches to the hub 320 to an outermost portion of the leaf 350.

Each leaf 350 can move between an expanded position and a collapsed position. The leaf 350 can form a hinge with the hub 320. In some aspects, the leaf 350 can rotate as a hinge as the leaf 350 rotates about the point of attachment 326. The leaf 350 can receive a spring 330 to bias the leaf 350 in the expanded position. The spring 330 may be a torsion spring 330. One portion of the spring 330 can be positioned against the first projecting surface 322. The other portion of the spring 330 can be received within a recess of the leaf 350.

Figure 24:
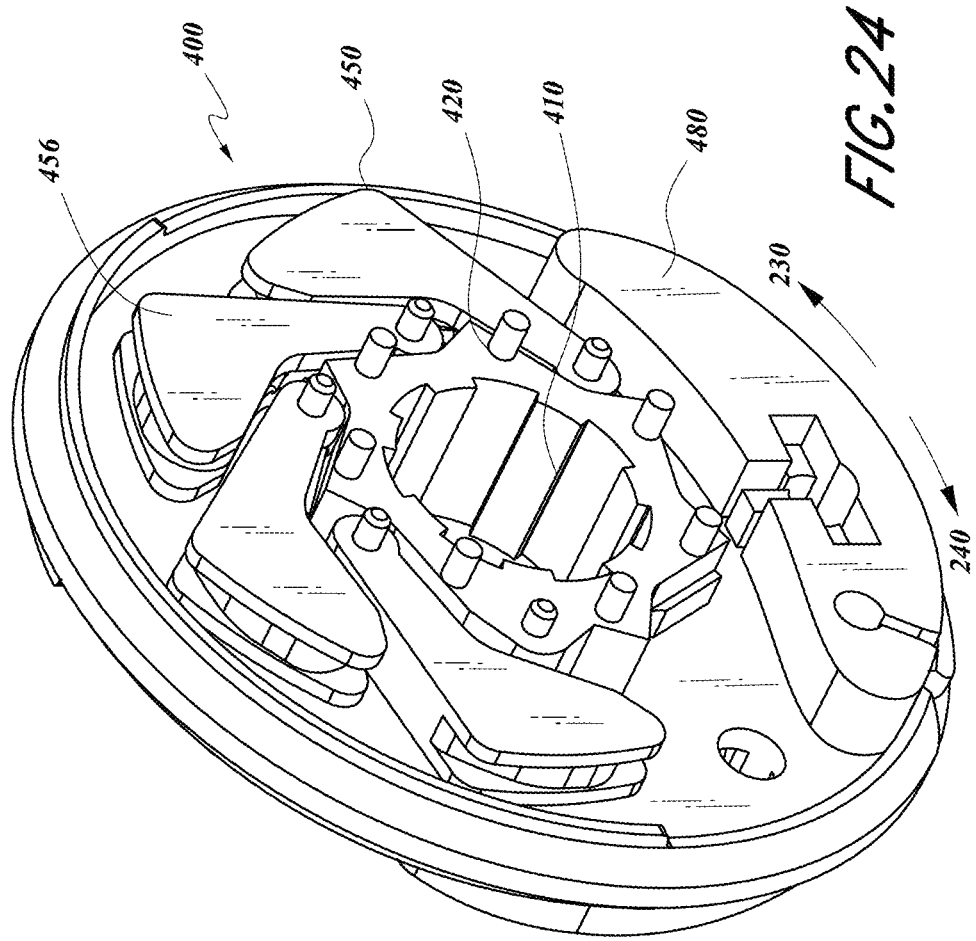
FIG. 24 illustrates a perspective back view of the dynamic pulley system of FIG. 23.
Figure 26:
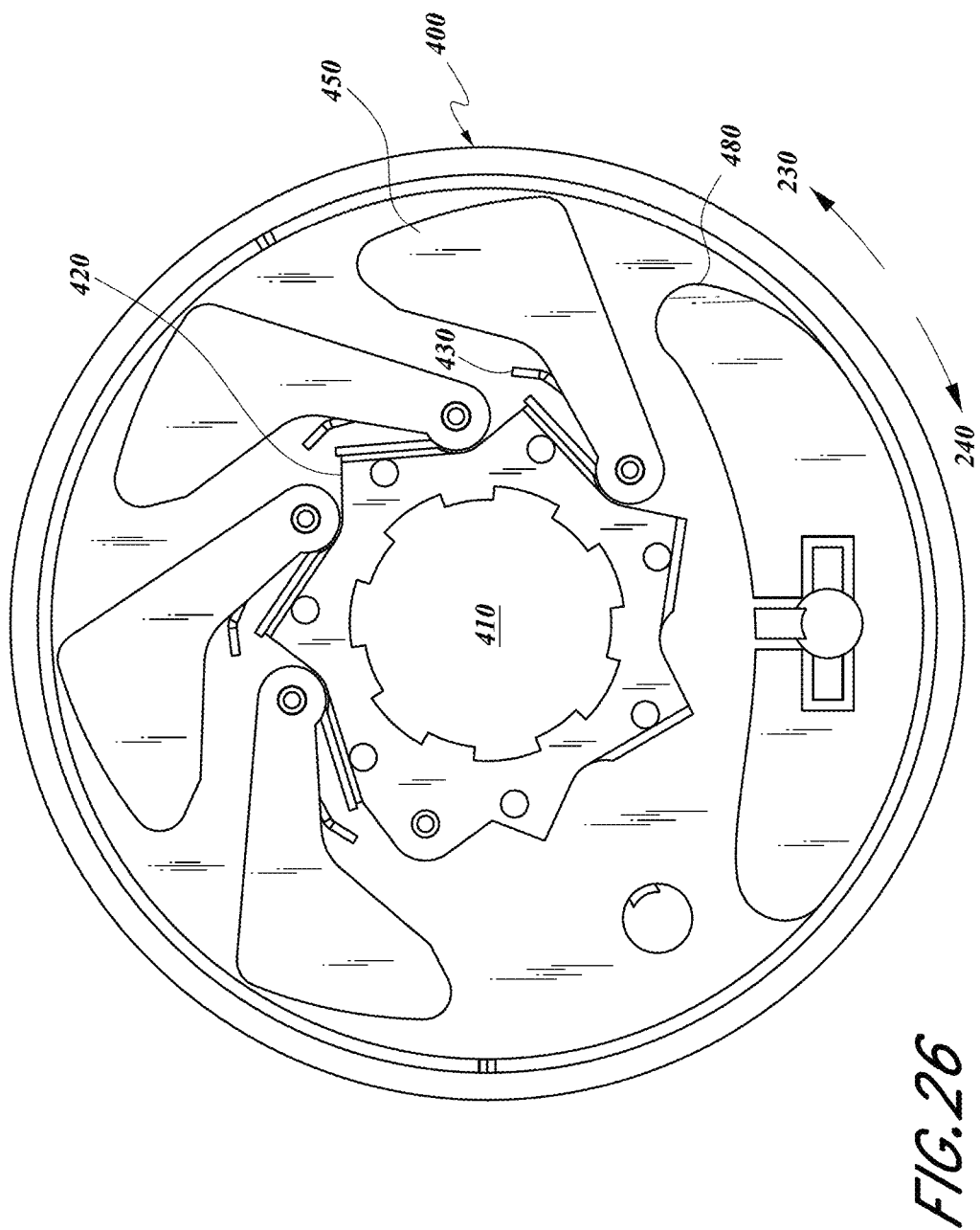
FIG. 26 illustrates a back view of the dynamic pulley system of FIGS. 23-25.

FIG. 24 illustrates a perspective back view of the dynamic tension pulley system. FIG. 26 illustrates a back view of the dynamic pulley system. The back side of the dynamic pulley system may be considered a second pulley 400. In some aspects, the second pulley 400 may be fixed or coupled to the first pulley 300. In some aspects, the second pulley 400 may be integral with the first pulley 300. In some aspects, the first pulley 300 and the second pulley 400 may be positioned back to back. In some aspects, the first pulley 300 and the second pulley 400 may be positioned back to back and positioned on the same drive input. In some aspects, the back side of the dynamic pulley system may be considered a second side 400 of a single pulley, positioned opposite from the first side 300 of a single pulley.

The second pulley 400, similar to the first pulley 300, includes a central hub 420 with a central hole 410. The second pulley 400 includes a series of leaves 450 extending outward from the hub 420. The second pulley 400 can include a fixed portion 480, similar to the first pulley 300. The leaves 450 may form a hinge with the central hub 420. The leaf 450 can receive a spring 430 to bias the leaf 450 in the expanded position. The second pulley 400 may be a substantial mirror of the first pulley 300, as described herein. The central hole 410 of the second pulley 400 may be aligned with the central hole 310 of the first pulley 300 when the first and second pulleys 300, 400 are positioned back to back.

FIGS. 27-28 illustrate the leaf 350 of the first pulley 300. The leaf 350 can include a proximal portion or radially inner portion 354 and a distal portion or radially outer portion 356. The leaf 350 can increase in diameter from the proximal portion 354 to the distal portion 356. The proximal portion 354 can be considered an innermost portion and the distal portion 356 can be considered the outermost portion. The proximal portion 354 can be narrow and the distal portion 356 can be wide. The distal portion 356 can extend on one side, such that the leaf 350 is asymmetrical and has an overall "L" shape. The distal portion 356 can include a sloped or inclined exterior edge. The distal exterior of the leaf 350 may be sloped radially inward in a first direction, such as a first rotational direction 240.

The sloped exterior edge can include a distal recess or groove 360, which can receive a portion of a pull wire (which may also be called a wire or a cable). In this manner, the wire can be engaged with the outermost portion 356 of the leaf 350. The proximal portion 354 can include a hole 352 to attach or anchor the leaf 350 to the pulley 300 at the point of attachment 326, such as adjacent to the central hub 320 (as shown in FIGS. 23 and 25). The proximal portion 354 can include a proximal recess or groove 358, which can receive at least a portion of the spring 330 (as shown in FIGS. 23 and 25). The proximal groove 358 can be on a first side of the leaf 350. The distal groove 360 can be positioned on a second side of the leaf 350, opposite from the first side. The distal groove 360 can extend from the second side of the leaf 350 (as shown in FIG. 27) to a distal end of the leaf 350 (as shown in FIG. 28).

As described herein, the second pulley 400 may be a mirror of the first pulley 300. The leaves 450 of the second pulley 400 (as shown in FIGS. 24 and 26) can be substantially similar but mirror images of the leaves 350 (as shown in FIGS. 23, 25, 27, and 28). As such, the exterior of the leaves 450 may be sloped radially inward in a second direction, such as a second rotational direction 230 of the pulley 300.

Figure 29:
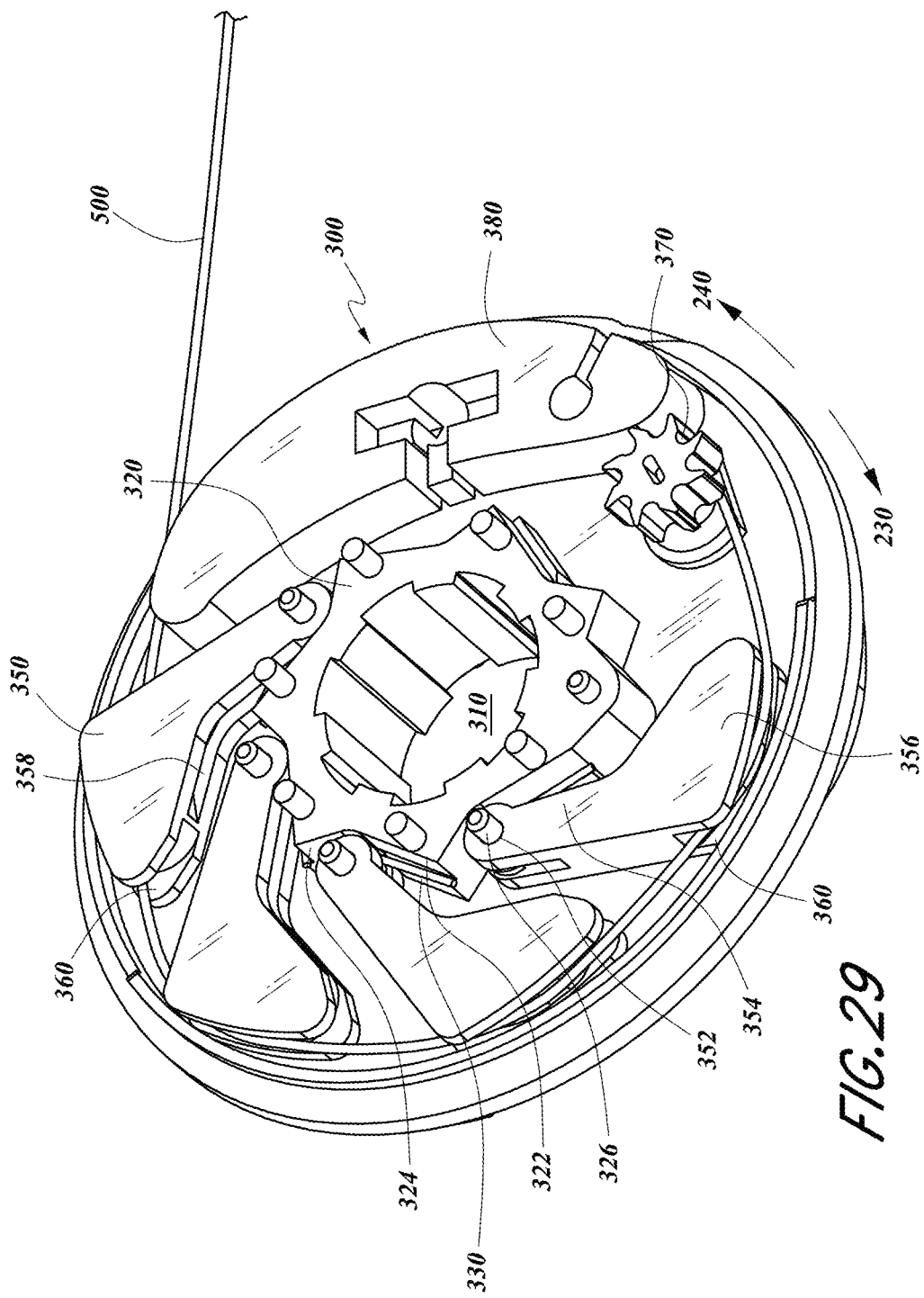
FIG. 29 illustrates a perspective front view of the dynamic pulley system of FIG. 23 with a wire extended over the leaves and the leaves in an expanded configuration.
Figure 30:
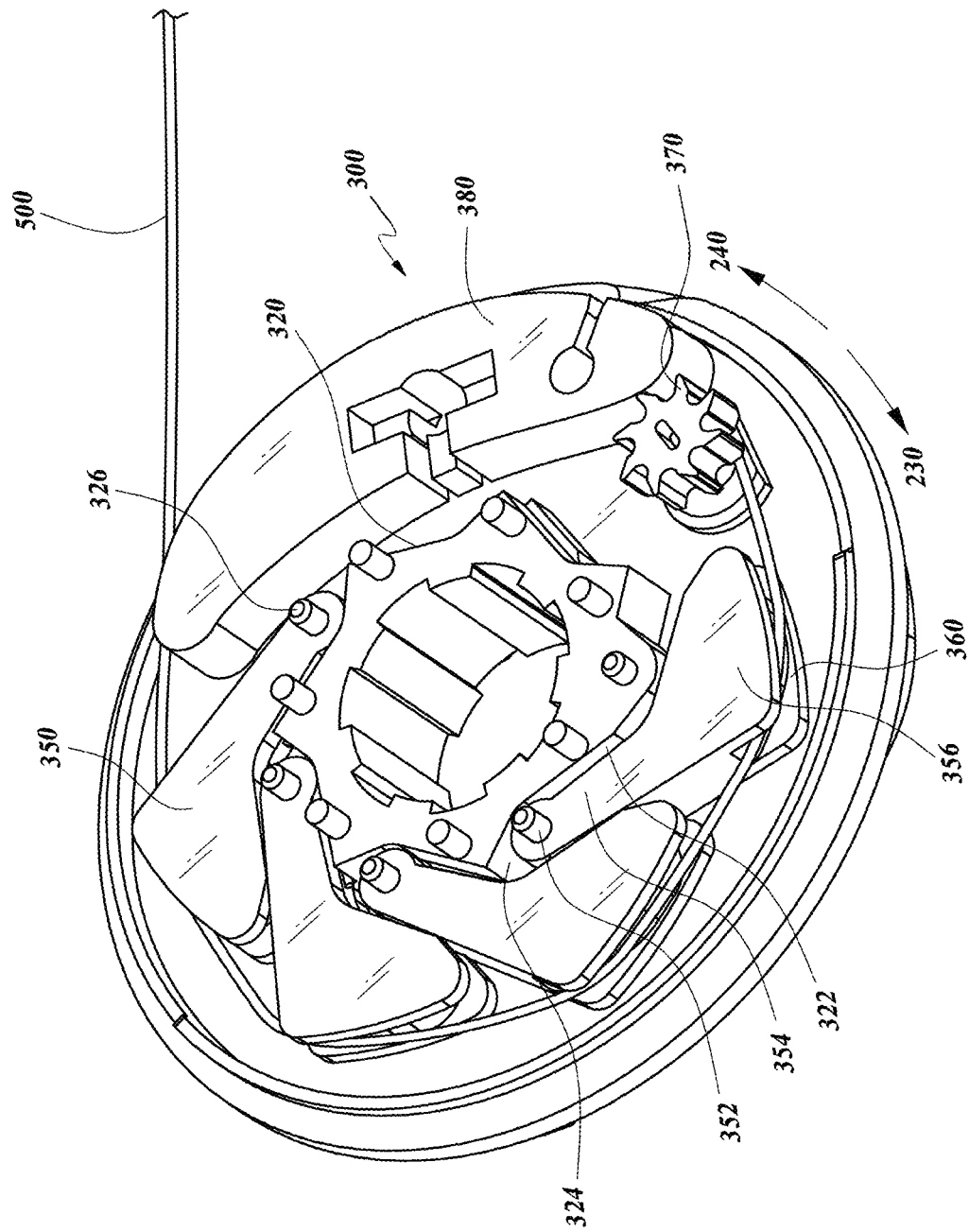
FIG. 30 illustrates a perspective front view of the dynamic pulley system of FIG. 29 with the wire extended over the leaves and the leaves in a collapsed configuration.

FIG. 29 illustrates a perspective front view of a dynamic pulley system with a wire 500 coupled to the leaves 350 in an expanded configuration. FIG. 30 illustrates a perspective front view of the dynamic pulley system with the wire 500 coupled to the leaves 350 in a collapsed configuration. As the dynamic pulley system is rotated and the pulley increases tension on the wire, the leaves 350 will then collapse. As the dynamic pulley system is rotated in a different direction, the pulley decreases tension on the wire 500 and the leaves 350 will then expand to take up slack in the wire 500.

A wire 500 can be coupled to the pulley 300 and extend around the one or more leaves 350. One end of the wire 500 can be attached to the pulley 300 at a termination point. The pulley 300 can further include a ratchet 370, which can be configured to pretension the wire 500. The ratchet 370 can receive one end of the wire 500. The one end of the wire 500 can terminate at the ratchet 370, such that the ratchet 370 can be considered the termination point. The wire 500 extends from the termination point around outermost portions 356 of the series of leaves 350. The wire 500 can then extend along an elongated shaft or wrist coupled to a tool of a medical instrument, as described previously. The wire 500 can then be actuatable to articulate the elongated shaft or wrist of a tool of the medical instrument.

As described herein, the series of leaves 350 can each have the distal groove 360 to receive the wire 500. When the wire 500 is received in the distal grooves 360 of the leaves 350, the wire 500 is configured to press an edge of the leaf 350 to collapse the leaf 350. The leaf will collapse under tension of the wire 500, where the tension is increased as the pulley 300 is rotated. The leaf 350 can be biased in an expanded configuration (e.g. with a spring) such that as tension is decreased or released as the pulley 300 is rotated, the leaf 350 will expand. With a series of leaves 350 positioned radially around a central hub 320, the directionality of the extended portion of the distal portions 356 can be aligned with one another and may each point in one rotational direction, such as the counterclockwise direction 240. The wire 500 can be wrapped can be around the series of leaves 350 in a second rotational direction, such as a clockwise direction 230.

As shown in FIG. 15, the drive unit 63 can include one or more drive shafts 64, which can be arranged with parallel axes. The one or more drive shafts 64 can be connected to the one or more pulleys to provide controlled torque to a medical instrument via the drive shafts 64. As described herein, the drive shaft 64 can be inserted into the central hole 310 of the first pulley 300. The drive shaft 64 can then drive the rotation of the pulley 300 to rotate in the first and second directions, such as counterclockwise 240 and clockwise 230. In various other configurations, a gear train or any other mechanical coupling can be used between the drive shaft 64 and the pulley so that the drive shaft can drive rotation of the pulley. As described herein, each leaf 350 can extend outward from the hub 320 and can be moveable from an expanded position and a collapsed position. The leaf 350 can be rotatable between the expanded position and the collapsed position. As described herein, the leaf 350 can pivot about an attachment point 326 of where the leaf 350 attaches to the pulley 300. The series of leaves 350 are configured to collapse during rotation in a first direction and to expand during rotation in a second direction, the second direction opposite from the first direction. For example, the first direction can be counterclockwise 240 and the second direction can be clockwise 230.

As shown in the expanded position in FIG. 29, the outermost portion 356 of the leaf 350 is positioned farthest from the central hub 320. As shown in the collapsed position in FIG. 30, the outermost position 356 of the leaf 350 is positioned closest to the central hub 320.

The leaf 350 can be configured to expand radially outward towards the expanded position as the pulley is rotated. The leaf 350 can be configured to collapse radially inward towards the collapsed position as the pulley is rotated in a different direction. Where the leaf 350 connects to the point 326 on the hub 320, the leaf 350 rotates as the hinge as the leaf 350 rotates about the point 326 on the hub 320 between the expanded and collapsed positions. In this manner, as the series of leaves 350 can be positioned around the pulley 300 and the series of leaves 350 are moveable between the expanded and collapsed position, the pulley 300 can be considered expanding and collapsing.

As the leaf 350 is coupled to the wire 500, the leaf 350 is configured to expand against the wire 500 as the pulley 300 is rotated. Each of the series of leaves 350 are configured to expand against the wire 500 as the pulley 300 is rotated. Each leaf 350 is configured to expand to push the wire away from the hub 320 to take up slack in the wire 500.

The leaves 350 of the pulley 300 may be biased in the expanded configuration (such as with the spring 330). As the pulley 300 rotates, one or more leaves 350 can come into contact with the wire 500. The leaves 350 will subsequently and sequentially collapse as the pulley 300 is rotated to pull and actuate the wire 500. Therefore, while one or more of the leaves 350 are in an expanded position, one or more of the leaves 350 may be in a fully or partially collapsed position. In some embodiments, the pulley may be configured to "handoff" the wire 500 to one or more of the leaves. In such embodiments, at a given time at least one leaf 350 is in contact with the wire 500 and at least one leaf 350 is not in contact with the wire 500. As the pulley rotates, the pulley can bring the non-contacting leaf into contact with the wire as the already contacting leaf rotates further with the pulley and may begin to collapse. Such a handoff sequence may be useful to provide a smooth response in the actuation of the wire 500 as the pulley is rotated. As the pulley 300 rotates in a direction (e.g. counterclockwise 240) that pulls on the wire 500, at least one of the series of leaves 350 collapses and at least another one of the series of leaves 350 is brought into contact with the wire 500.

The fixed portion 380 can be considered a fixed leaf or a crescent shaped contour. The fixed portion 380 can increase the diameter of the first pulley 300. The increased diameter can cause less slack generation and reduce the required rotation of the pulley 300. The fixed portion 380 can come in contact with the wire 500 when the series of leaves 350 have collapsed. The leaves 350 can then handoff or transfer the wire 500 to the fixed portion 380 of the pulley 300, as the pulley 300 continues to rotate, such that the outer edge of the fixed portion 380 now comes into contact with the wire 500. In some embodiments, the pulley 300 can be configured such that the handoff from the leaves 350 to the fixed portion 380 occurs when the leaves 350 are not fully collapsed. The handoff of the wire 500 from the series of leaves 350 to the fixed portion 380 mitigates premature collapsing of the leaves 350 under higher tension under the wire 500. As each leaf 350 collapses, the remaining leaves 350 that remain expanded and that are in contact with the wire 500 experience an increase in tension under the wire 500. When the pulley 300 is rotated such that the fixed portion 380 comes into contact with the wire 500, tension from the wire 500 can then be distributed to the fixed portion 380 and reduce or mitigate premature collapsing of the leaves 350.

In some embodiments, during rotation of the pulley 300, the handoff of the wire 500 can occur between the leaves 350 and the fixed portion 380 as described. In other embodiments, during rotation of the pulley 300, the handoff of the wire 500 can also occur between leaves 350, as some leaves 350 come in contact with the wire 500 and some leaves 350 do not contact the wire 500. For example, the wire 500 can be passed from one leaf 350 to another leaf 350 as each leaf 350 collapses under tension from the wire 500 and the next leaf 350 in the biased expanded configuration comes into contact with the wire 500. As the pulley 300 is rotated in the direction that pulls on the wire 500, the expanded leaves 350 will be brought into contact with the wire 500 as the other leaves 350 start to collapse. In some embodiments, there is no handoff of the wire 500.

Figure 31:
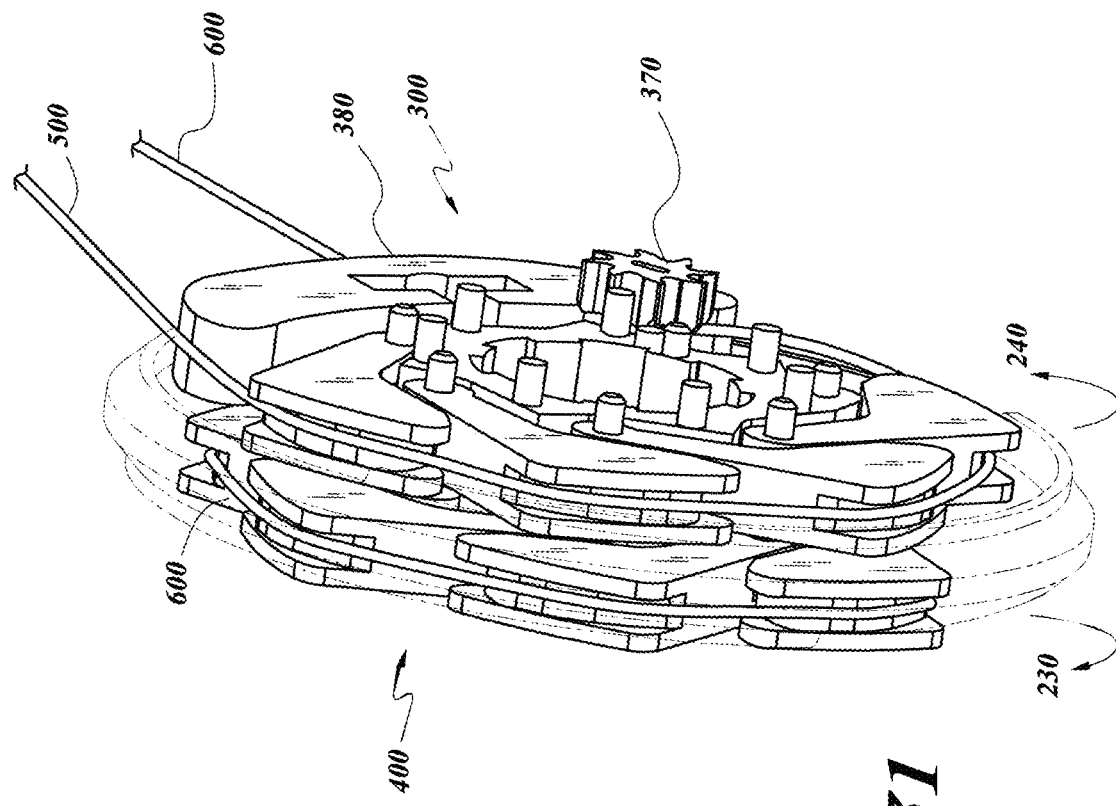
FIG. 31 illustrates a perspective side view of the dynamic pulley system of FIG. 23 with a pair of wires extending over the leaves.

The second pulley 400 may be a mirror of the first pulley 300. The second pulley 400 can be configured to operate in a similar manner as the pulley 300, but in opposite directions. FIG. 31 illustrates a perspective side view of the dynamic pulley system with certain components being shown as transparent, to show the first series of leaves 350 and the second series of leaves 450. The first pulley 300 can be coupled to or stacked on top of the second pulley 400. The first pulley 300 can be back to back with the second pulley 400. When the first and second pulleys 300, 400 are positioned back to back, the respective central holes 310, 410 can be aligned. A single rotational drive input (such as the same drive shaft 64 as described above) can pass through the aligned central holes 310, 410 of the first and second pulley 300, 400. The rotational drive input can be coupled to the pulley 300 and second 400 to simultaneously drive the first pulley 300 and the second pulley 400 together. As described herein, the rotational drive input can drive the first pulley 300 and second pulley 400 in the first and second directions 240, 230.

As described herein, the system may also be considered a single pulley with two sides 300, 400. The first series of leaves 350 are attached to a first side 300 of the pulley, further comprising a second series of leaves 450 fixed to a second side 400 of the pulley. The exterior of each of the first series of leaves 350 is sloped in a first rotational direction 240. The wire 500 can terminate on the pulley 300 and wrap around the outermost portions 356 of the leaves 350 in a second rotational direction 230. The exterior of each of the second series of tabs 450 is sloped in a second rotational direction 230, opposite from the first rotational direction 240. The second wire 600 can terminate on the second pulley 400 and wrap around the outermost portions 456 of the second series of leaves 450 in a first rotational direction 240.

The first pulley 300 can be rotated in a first rotational direction 240 to pull on a first wire 500 coupled to the first pulley 300. The first pulley 300 can be rotated in a second rotational direction 230 opposite the first rotational direction. While the first pulley 300 is rotated in the second rotational direction 230, the first pulley 300 can expand. The expansion of the first pulley 300 takes up slack in the wire 500 as the first pulley 300 is rotated in the second 230. The first pulley 300 can include a first series of leaves or wings 350. The first series of wings 350 can move in the expanded position when the first pulley 300 is expanding. The first series of wings 350 can move in the collapsed position when the pulley 300 is rotated in the first rotational direction 240.

The second pulley 400 can be coupled to the first pulley 300. Since the second pulley 400 is a mirror image of the first pulley 300, the second pulley 400 can operate in a similar manner in expanding and collapsing but in opposite directions from the first pulley 300.

The second pulley 400 can be rotated in the second rotational direction 230 to pull on a second wire 600 coupled to the second pulley 400. The second pulley 400 can be rotated in the first rotational direction 240, opposite the second rotational direction. While the second pulley 400 is rotated in the first direction 240, the second pulley 400 can expand. The expansion of the second pulley 400 takes up slack in the second wire 600 as the second pulley 400 is rotated in the first direction 240. The second pulley 400 can include a second series of leaves or wings 450. The second series of wings 450 can move in the expanded position when the second pulley 400 is expanding. The second series of wings 450 can move in the collapsed position when the pulley 400 is rotated in the second rotational direction 230.

Figure 32:
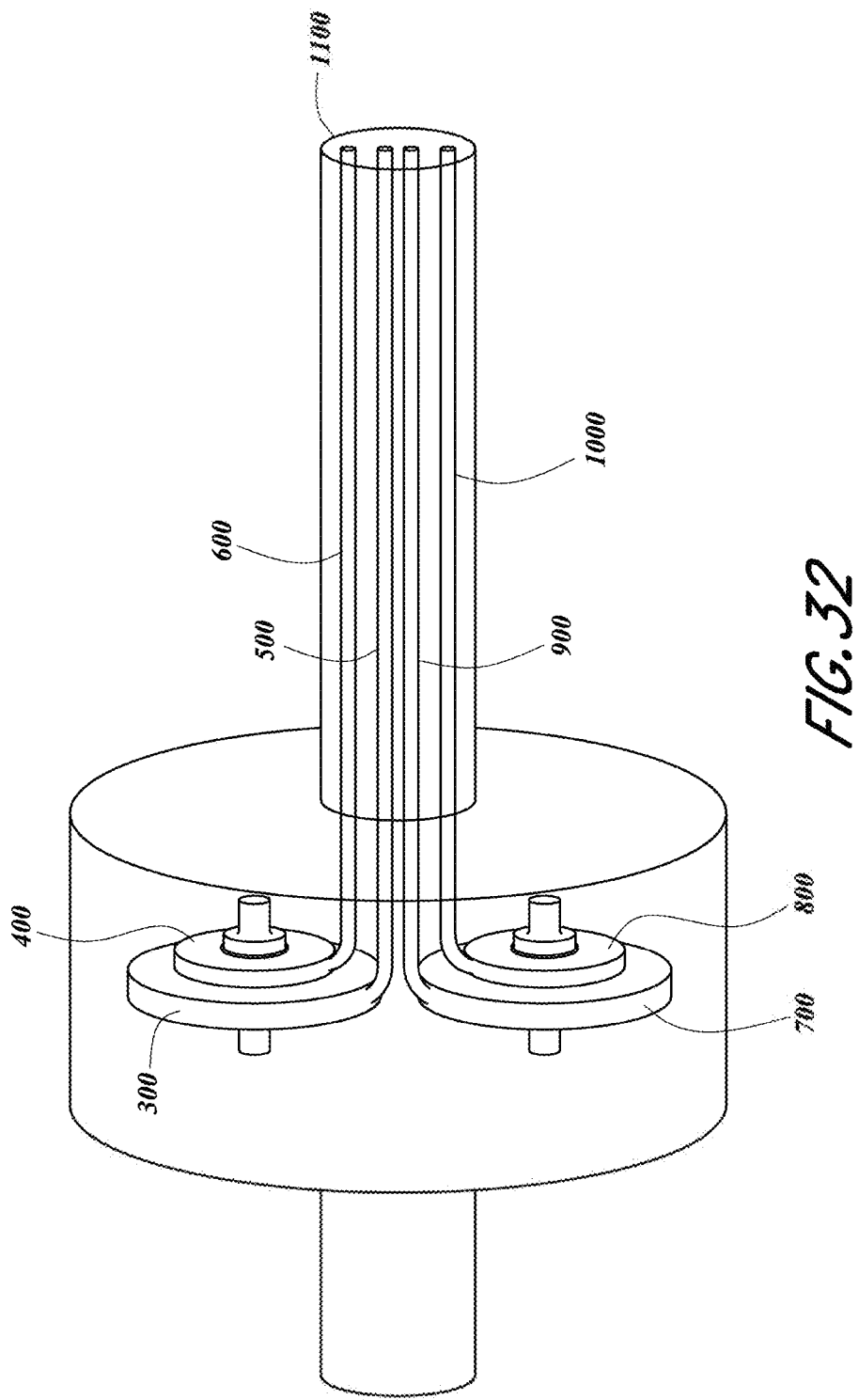
FIG. 32 illustrates a medical instrument with a dynamic pulley system with four pulleys.

FIG. 32 illustrates multiple dynamic pulleys connected to pull wires connected to an instrument or an articulating member 1100. The instrument or articulating member 1100 can be actuated by four pull wires 500, 600, 900, 1000. The four pull wires 500, 600, 900, 1000 can be actuated to articulate the instrument 1100. Two pull wires 500, 600 can be controlled and actuated by the first pulley 300 and second pulley 400 as described and shown in FIG. 31. The other two pull wires 900, 1000 can be controlled and actuated by a third pulley 700 and fourth pulley 800. The third and fourth pulleys 700, 800 can have a the same structure as the first and second pulleys 300, 400 and operate in the same way. Although not necessarily depicted in the schematic illustration of FIG. 32, each pair of pull wires coupled to a common pulley stack may exit the pulley stack from opposing sides of the pulley stack in a similar manner to that shown in FIG. 31. Accordingly, the pair of pull wires 500, 600 may exit the first pulley 300 and the second pulley 400 from opposing sides or opposing directions of the first and second pulleys (e.g., one pull wire exiting clockwise and the other pull wire exiting counter clockwise), while the pair of pull wires 900, 1000 may exit third pulley 700 and the fourth pulley 800 from opposing sides or opposing directions of the third and fourth pulleys (e.g., one pull wire exiting clockwise and the other pull wire exiting counter clockwise). As described above in FIG. 15, the drive unit 63 can include multiple drive shafts 64 which are arranged in parallel. While one drive shaft 64 can drive the first and second pulleys 300, 400 as described above, the third and fourth pulleys 700, 800 can be rotated by a second drive shaft 64 parallel to the first drive shaft 64.

3. Implementing Systems and Terminology

Implementations disclosed herein provide systems, methods and apparatus for related to dynamic pulleys for robotically controllable medical instruments.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The specific computer-implemented functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic medical system comprising:
an elongated shaft configured for insertion into a patient;
a pull wire extending along the elongated shaft, the pull wire actuatable to articulate the elongated shaft; and
a dynamic pulley coupled to the pull wire, the dynamic pulley configured to collapse during rotation in a first direction and to expand during rotation in a second direction opposite the first direction,
wherein one end of the pull wire is fixedly coupled to the pulley at a termination point.

2. The robotic medical system of claim 1, further comprising:
an instrument base connected to a proximal end of the elongated shaft, the instrument base including:
a rotational drive input,
wherein the rotational drive input is coupled to the pulley and drives rotation of the pulley in the first and second directions.

3. The robotic medical system of claim 1, further comprising:
a second pull wire extending along the elongated shaft, the second pull wire actuatable to articulate the elongated shaft; and
a second dynamic pulley coupled to the second pull wire, the second dynamic pulley configured to collapse during rotation in the second direction and to expand during rotation in the first direction,
wherein the dynamic pulley and the second dynamic pulley are controlled by a single rotational drive input, and
wherein the pull wire and second pull wire are configured to bend the elongated shaft in two directions.

4. The robotic medical system of claim 3, wherein the two directions are opposing directions.

5. A robotic medical pulley system comprising:
a pulley comprising a hub and a tab extending outward from the hub, the tab being moveable between an expanded position and a collapsed position; and
one end of a wire fixedly coupled to the pulley at a termination point and the wire extending around the tab, wherein the tab is configured to expand radially outward towards the expanded position as the pulley is rotated.

6. The robotic medical pulley system of claim 5, further comprising a series of tabs, wherein the tab is one of the series of tabs, and wherein each of the series of tabs are configured to expand against the wire as the pulley is rotated.

7. The robotic medical pulley system of claim 6, wherein the wire extends from the termination point around outermost portions of the series of tabs.

8. The robotic medical pulley system of claim 6, wherein an exterior of each of the series of tabs is sloped radially inward in a first rotational direction.

9. The robotic medical pulley system of claim 8, wherein the series of tabs are attached to a first side of the pulley, wherein the pulley system further comprises a second series of tabs attached to a second side of the pulley, and wherein an exterior of each of the second series of tabs is sloped in a second rotational direction opposite from the first rotational direction.

10. The robotic medical pulley system of claim 6, wherein each of the series of tabs is configured to expand to push the wire away from the hub to take up slack in the wire.

11. The robotic medical pulley system of claim 6, wherein at least one of the series of tabs is configured to contact the wire to provide tension to the wire while at least another one of the series of tabs is not in contact with the wire.

12. The robotic medical pulley system of claim 6, wherein as the pulley rotates in a direction that pulls on the wire, at least one of the series of tabs collapses and at least another one of the series of tabs is brought into contact with the wire.

13. The robotic medical pulley system of claim 5, wherein the tab has a length from a point where the tab attaches to the hub to an outermost portion of the tab, wherein the wire is engaged with the outermost portion of the tab, and wherein the point where the tab attaches to the hub defines an axis of rotation of the tab.

14. The robotic medical pulley system of claim 5, wherein the wire is configured to press an edge of the tab to collapse the tab.

15. The robotic medical pulley system of claim 5, wherein the tab forms a hinge with the hub, wherein the tab includes a spring to bias the tab to the expanded position.

16. The robotic medical pulley system of claim 5, wherein the tab connects to a point on the hub, wherein the tab rotates about the point on the hub between the expanded and collapsed positions.

17. The robotic medical pulley system of claim 5, wherein the hub is configured to be driven by a drive shaft in a first rotational direction or a second rotational direction.

18. The robotic medical pulley system of claim 5, wherein the pulley further comprises a ratchet configured to pretension the wire.

19. A method for controlling a robotic medical system, the method comprising:
rotating a pulley in a first rotational direction to pull on a wire coupled to the pulley, one end of the wire fixedly coupled to the pulley at a termination point;
rotating the pulley in a second rotational direction opposite the first rotational direction; and
expanding the pulley while rotating the pulley in the second rotational direction, wherein expansion of the pulley takes up slack in the wire as the pulley is rotated in the second rotational direction.

20. The method of claim 19, wherein the pulley comprises a series of wings, the method further comprising: moving the series of wings to an expanded position when expanding the pulley.

21. The method of claim 20, further comprising moving the series of wings to a collapsed position when the pulley is rotated in the first rotational direction.

* * * * *